United States Patent
Soleymani et al.

(10) Patent No.: US 10,319,390 B2
(45) Date of Patent: Jun. 11, 2019

(54) METHOD AND SYSTEM FOR MULTI-TALKER BABBLE NOISE REDUCTION

(71) Applicant: New York University, New York, NY (US)

(72) Inventors: Roozbeh Soleymani, New York, NY (US); Ivan W. Selesnick, Maplewood, NJ (US); David M. Landsberger, Forest Hills, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 15/703,721

(22) Filed: Sep. 13, 2017

(65) Prior Publication Data

US 2018/0012614 A1  Jan. 11, 2018

Related U.S. Application Data

(63) Continuation-in-part of application No. PCT/US2017/018696, filed on Feb. 21, 2017.
(Continued)

(51) Int. Cl.
*G10L 19/00* (2013.01)
*G10L 21/02* (2013.01)
(Continued)

(52) U.S. Cl.
CPC ...... *G10L 21/0205* (2013.01); *G10L 19/0216* (2013.01); *G10L 21/0208* (2013.01); *G10L 2021/02087* (2013.01)

(58) Field of Classification Search
USPC ................. 704/200–232, 500–504
See application file for complete search history.

(56) References Cited

U.S. PATENT DOCUMENTS

| | | | |
|---|---|---|---|
| 2003/0023430 A1* | 1/2003 | Wang | G10L 19/26 704/226 |
| 2005/0149325 A1* | 7/2005 | Deng | G10L 21/0208 704/226 |
| 2011/0305345 A1* | 12/2011 | Bouchard | G10L 21/0208 381/23.1 |

OTHER PUBLICATIONS

Selesnick, Ivan. "Wavelet Transform With Tunable Q-Factor". IEEE Transactions on Signal Processing, vol. 59, No. 8, Aug. 2011. (Year: 2011).*

* cited by examiner

*Primary Examiner* — Jesse S Pullias
(74) *Attorney, Agent, or Firm* — Fay Kaplun & Marcin, LLP

(57) ABSTRACT

A system and method for improving intelligibility of speech is provided. The system and method may include obtaining an input audio signal frame, classifying the input audio signal frame into a first category or a second category, wherein the first category corresponds to the noise being stronger than the speech signal, and the second category corresponds to the speech signal being stronger than the noise, decomposing the input audio signal frame into a plurality of sub-band components; de-noising each sub-band component of the input audio signal frame in parallel by applying a first wavelet de-noising method including a first wavelet transform and a predetermined threshold for the sub-band component, and a second wavelet de-noising method including a second wavelet transform and the predetermined threshold for the sub-band component, wherein the predetermined threshold for each sub-band component is based on at least one previous noise-dominant signal frame received by the receiving arrangement.

18 Claims, 29 Drawing Sheets

Related U.S. Application Data

(60) Provisional application No. 62/394,520, filed on Sep. 14, 2016, provisional application No. 62/297,536, filed on Feb. 19, 2016.

(51) Int. Cl.
*G10L 19/02* (2013.01)
*G10L 21/0208* (2013.01)

METHOD AND SYSTEM FOR MULTI-TALKER BABBLE NOISE REDUCTION

PRIORITY CLAIM

This application claims priority to U.S. Provisional Patent Application Ser. No. 62/394,520 filed Sep. 14, 2016, and is a Continuation-in-Part Application of PCT Application Serial No. PCT/US2017/018696 filed on Feb. 21, 2017, which claims priority to U.S. Provisional Patent Application Ser. No. 62/297,536 filed Feb. 19, 2016, the entire contents of all of the above-referenced applications are hereby incorporated by reference herein.

GOVERNMENT FUNDING

This invention was made with the U.S. Government support under Grant Nos. NIH Grant R01-DC12152. The U.S. Government has certain rights in the invention.

FIELD OF INVENTION

The present invention relates generally to a method and a system for noise reduction, such as, for example, in a cochlear implant, a telephone, an electronic communication, etc.

BACKGROUND

Cochlear implants ("CI"s) may restore the ability to hear to deaf or partially deaf individuals by providing electrical stimulation to the auditory nerve via a series of electrodes placed in the cochlea. CIs may successfully provide the ability of almost all post-lingually deaf users (i.e., those who lost their hearing after learning speech and language) to gain an auditory understanding of an environment and/or restore hearing to a level suitable for an individual to understand speech without the aid of lipreading.

One of the key challenges for CI users is to be able to clearly and/or intelligibly understand speech in the context of background noise. Conventional CI devices have been able to aid patients to hear and ascertain speech in a quiet environment, but the performance of such devices quickly degrades in noisy environments. There have been a number of attempts to isolate speech from background noise, e.g., single-channel noise reduction algorithms. Typical single-channel noise reduction algorithms have included applying a gain to the noisy envelopes, pause detection and spectral subtraction, feature extraction and splitting the spectrogram into noise and speech dominated tiles. However, even with these algorithms, speech understanding in the presence of competing talkers (i.e., speech babble noise) remains difficult and additional artifacts are often introduced. Furthermore, mobile communications have created an ever-rising need to be able to clearly and/or intelligibly understand speech while one user may be in a noisy environment. In particular, there is a need for improving speech understanding in telephonic communications, even in the presence of competing talkers (i.e., background speech babble noise).

Despite good progress in improving speech quality and listening ease, little progress has been made in designing algorithms that can improve speech intelligibility. Conventional methods that have been found to perform well in steady background noise generally do not perform well in non-stationary noise (e.g., multi-talker babble). For example, it is often difficult to accurately estimate the background noise spectrum. Moreover, applying noise removal methods to already noisy signals usually introduces distortion and artifacts (e.g., musical noise) to the original signal, which in many cases lead to almost no significant intelligibility improvement. All these reasons make the improvement of speech intelligibility in the presence of competing talkers a difficult problem.

Therefore, there is a need to provide a method or system for noise reduction, particularly for use in or with a cochlear implant, telephone or electronic communications device, that provides speech quality and/or intelligibility.

SUMMARY OF THE INVENTION

In accordance with the foregoing objectives and others, one embodiment of the present invention provides systems and methods for reducing noise and/or improving intelligibility of an audio signal.

In one aspect, a method for reduction of noise is provided or a method for improving intelligibility of speech is provided. The method comprises a first step for receiving from a receiving arrangement an input audio signal frame comprising a speech signal and a noise. In certain embodiments, the input audio signal frame may be less than 100 ms in duration. In some embodiments, the noise comprises a multi-talker babble noise. The method also comprises a step for classifying the input audio signal frame into a first category or a second category. The first category corresponds to the noise being stronger than the speech signal, and the second category corresponds to the speech signal being stronger than the noise. As discussed herein, the term "stronger" may refer to having more of one component over another, e.g., the first category may correspond to an input signal being comprised more of noise as compared to speech signal. Similarly, the second category may correspond to an input signal being comprised more of speech signal than noise. In certain embodiments, the classifying step may comprise applying a principle component analysis using a plurality of features, wherein the plurality of features includes at least one of: (1) an envelope variance feature of the input audio signal frame; (2) an envelope mean crossing feature of the input audio signal frame; (3) a root mean square feature of the input audio signal frame as compared to a predetermined threshold value; and (4) an entropy feature of a histogram of the input audio signal frame, and classifying the input audio signal frame into the first category when the applying step identifies predominantly noise from the input audio signal frame, and into the second category when the principle component analysis identifies predominantly speech signal from the input audio signal frame. In one exemplary embodiment, each of the plurality of features may each be weighted differently in the principle component analysis. In another exemplary embodiment, the predetermined threshold value for the root mean square feature is based on a previous audio signal frame received by the receiving arrangement. In particular, the previous audio signal frame may include predominantly noise. The method further comprises a step for decomposing the input audio signal frame into a plurality of sub-band components. In addition, the method comprises a step for de-noising each sub-band component of the input audio signal frame in parallel by applying a first wavelet de-noising method including a first wavelet transform and a predetermined threshold for the sub-band component, and a second wavelet de-noising method including a second wavelet transform and the predetermined threshold for the sub-band component. The predetermined threshold for each sub-band component is based on at least one previous noise-dominant signal frame received by the receiving arrangement. In addition, the first and second wavelets are configured to more aggressively de-noise the input audio signal frame when the input audio signal frame is classified in the first category as compared to when the input audio signal frame is classified in the second category. In one embodiment, the first and second wavelet transforms are Tunable Q-Factor Wavelet Transforms (TQWTs). The first and second wavelet transforms may be selected based whether the input audio signal is classified into the first category or the second category. In another embodiment, each sub-band component may comprise a plurality of wavelet coefficients corresponding to an amplitude of the sub-band component of the input audio signal frame. In addition, the predetermined threshold for each sub-band component may be selected based on an amount of noise present in the sub-band component, and an energy level represented by the plurality of wavelet coefficients. In a further embodiment, the method may further comprise a step for adjusting the plurality of features based on the input audio signal by an iterative method using a Gaussian mixture model for a plurality of sub-categories, wherein the first and second categories are each further divided into the plurality of sub-categories.

In another aspect, an alternative method for reduction of noise is provided or a method for improving intelligibility of speech is provided. The method comprises a first step for obtaining, from a receiving arrangement, an input audio signal frame comprising a speech signal and a noise. The method also comprises a step for classifying the input audio signal frame into a first category or a second category. The first category corresponds to the noise being stronger than the speech signal, and the second category corresponds to the speech signal being stronger than the noise. The method further comprises a step for decomposing the input audio signal frame into a plurality of sub-band components. In addition, the method comprises a de-noising each sub-band component of the input audio signal frame in parallel by applying a plurality of wavelet de-noising methods, each wavelet de-noising method including a wavelet transform and a predetermined threshold for the sub-band component. The predetermined threshold for each sub-band component is based on at least one previous noise-dominant signal frame received by the receiving arrangement. In addition, each of the wavelet transforms may be different from other wavelet transforms, and may each be configured to more aggressively de-noise the input audio signal frame when the input audio signal frame is classified in the first category as compared to when the input audio signal frame is classified in the second category.

In another aspect, a non-transitory computer readable medium storing a computer program that is executable by at least one processing unit is provided. The computer program comprise sets of instructions for: receiving from a receiving arrangement an input audio signal frame comprising a speech signal and a noise; classifying the input audio signal frame into a first category or a second category, wherein the first category corresponds to the noise being stronger than the speech signal, and the second category corresponds to the speech signal being stronger than the noise; decomposing the input audio signal frame into a plurality of sub-band components; and de-noising each sub-band component of the input audio signal frame in parallel by applying a first wavelet de-noising method including a first wavelet transform and a predetermined threshold for the sub-band component, and a second wavelet de-noising method including a second wavelet transform and the predetermined threshold for the sub-band component, wherein the predetermined threshold for each sub-band component is based on at least one previous noise-dominant signal frame received by the receiving arrangement, wherein the first and second wavelets are configured to more aggressively de-noise the input audio signal frame when the input audio signal frame is classified in the first category as compared to when the input audio signal frame is classified in the second category.

In a further aspect, a system for improving intelligibility for a user is provided. The system may comprise a receiving arrangement configured to receive an input audio signal frame comprising a speech signal and a noise. The system may also comprise a processing arrangement configured to receive the input audio signal frame from the receiving arrangement, classify the input audio signal frame into a first category or a second category, wherein the first category corresponds to the noise being stronger than the speech signal, and the second category corresponds to the speech signal being stronger than the noise, decompose the input audio signal frame into a plurality of sub-band components, and de-noise each sub-band component of the input audio signal frame in parallel by applying a first wavelet de-noising method including a first wavelet transform and a predetermined threshold for the sub-band component, and a second wavelet de-noising method including a second wavelet transform and the predetermined threshold for the sub-band component, wherein the predetermined threshold for each sub-band component is based on at least one previous noise-dominant signal frame received by the receiving arrangement, wherein the first and second wavelets are configured to more aggressively de-noises the input audio signal frame when the input audio signal frame is classified in the first category as compared to when the input audio signal frame is classified in the second category.

These and other aspects of the invention will become apparent to those skilled in the art after a reading of the following detailed description of the invention, including the figures and appended claims.

BRIEF DESCRIPTION OF THE FIGURES

FIG. 6a shows data corresponding to percentages of words correct in normal patients for input signals that are unprocessed and processed using the exemplary method of FIG. 2a.

FIG. 6b shows data corresponding to MUSHRA scores in normal patients for input signals that are unprocessed and processed using the exemplary method of FIG. 2a.

FIG. 7 shows data corresponding to percentages of words correct in CI patients for input signals that are unprocessed and processed using the exemplary method of FIG. 2a.

FIG. 8 shows data corresponding to MUSHRA scores in CI patients for input signals that are unprocessed and processed using the exemplary method of FIG. 2a.

DETAILED DESCRIPTION

Figure 1:
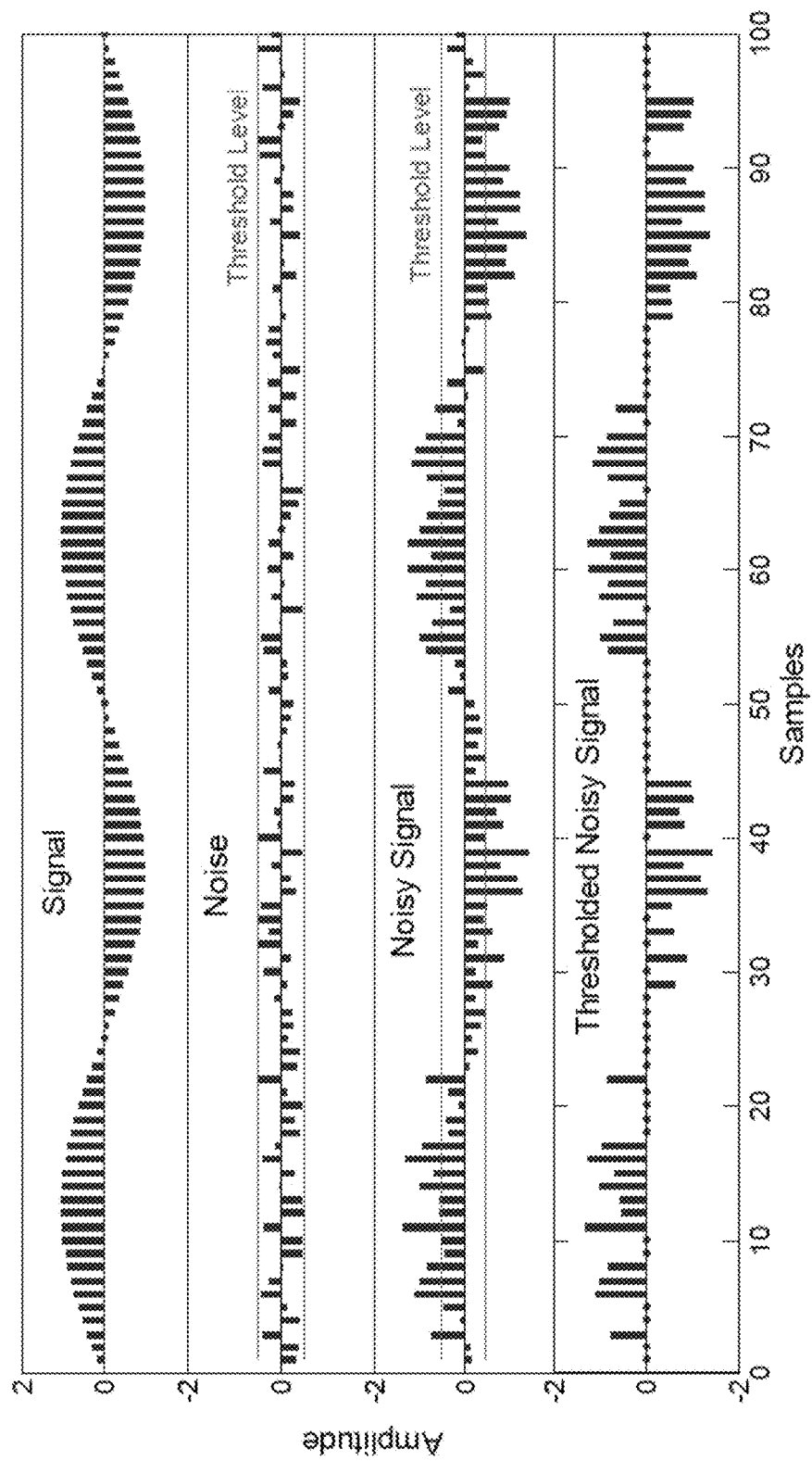
FIG. 1 shows exemplary representations of signal and noise amplitudes over a time domain, combination of the signal and noise forming a noisy signal, and the noisy signal de-noised by simple time-domain thresholding.

The present invention is directed to a method and system for multi-talker babble noise reduction. The system may be used with an audio processing device, a cochlear implant, a mobile computing device, a smart phone, a computing tablet, a computing device to improve intelligibility of input audio signals, particularly that of speech. For example, the system may be used in a cochlear implant to improve recognition and intelligibility of speech to patients in need of hearing assistance. In one particular embodiment, the method and system for multi-talker babble noise reduction may utilize Q-factor based signal decomposition, which is further described below. In another embodiment, the method and system for real-time multi-talker babble noise reduction may utilize a novel classifier, a method for parallel de-noising, a new method for de-noising using adaptive thresholding, and/or a new method for de-noising by decomposing the signal into a plurality of sub-bands, all of which are further described below.

Cochlear implants (CIs) may restore the ability to hear to deaf or partially deaf individuals. However, conventional cochlear implants are often ineffective in noisy environments, because it is difficult for a user to intelligibly understand speech in the context of background noise. Specifically, original signals having a background of multi-talker babble noise, is particularly difficult to filter and/or process to improve intelligibility to the user, because it often includes background noise that does not adhere to any predictable prior pattern. Rather, multi-talker babble noise tends to reflect the spontaneous speech patterns of having multiple speakers within one room, and it is therefore difficult for the user to intelligibly understand the desired speech while it is competing to simultaneous multi-talker babble noise.

In the exemplary methods for noise reduction described herein, in particular, multi-talker babble noise reduction in a cochlear implant, the methods may be used to improve recognition and intelligibility of speech to patients in need of hearing assistance. Any suitable cochlear implant may be used with the exemplary methods described herein. In particular, the cochlear implant may detect an audio signal and restore a deaf or partially deaf individual's ability to hear by providing an electrical stimulation to the auditory nerve corresponding to the audio signal. However, often the input audio signal may be noisy and cannot be recognized or discerned by the user. Therefore, the input signal may be further processed, e.g., filtered, to improve clarity and/or intelligibility of speech to the patient.

The input audio signal may be a continuous audio signal and may be broken down into predetermined segments and/or frames for processing by the exemplary methods. In particular, in a real-time application, such as an application for improving hearing for a CI user or for improving intelligibility of audio communications on a communications device (such as mobile communications device, a telephone, a smart phone, etc.), the input signal may include non-steady noise where the level of noise, e.g., signal to noise ratio, may change over time. To adapt to the changing levels of noise intensity in an input signal, the signal may be separated into a plurality of frames of input signal, where each frame may be individually analyzed and/or de-noised, such as for example, processing each individual frame using the exemplary methods. The input signal may be divided into the plurality of frames by any suitable means. The exemplary methods may be continuously applied to each successive frame of the input signal for analysis and/or de-noising. In some embodiments, the input audio signal may be obtained and each frame of the input audio signal may be processing by the exemplary methods in real-time or substantially real-time, meaning within a time frame that is negligible or imperceptible to a user, for example, within less than 100 milliseconds, less than 90 milliseconds, less than 70 milliseconds, or less than 40 milliseconds.

There are a number of different approaches to filtering and/or reducing noise in a noisy audio signal to a cochlear implant. For example, modulating based methods may differentiate speech from noise based on temporal characteristics, including modulations of depth and/or frequency, and may subsequently apply a gain reduction to the noisy signals or portions of signals, e.g., noisy envelopes. In another example, spectral subtraction based methods may estimate a noise spectrum using a predetermined pattern, which may be generated based on prior knowledge (e.g., detection of prior speech patterns) or speech pause detection, and may subsequently subtract the estimated noise spectrum from a noisy speech spectrum. As a further example, sub-space noise reduction methods may be based on a noisy speech vector, which may be projected onto different sub-spaces for analysis, e.g., a signal sub-space and a noise sub-space. The clean signal may be estimated by a sub-space noise reduction method by retaining only the components in the signal sub-space, and nullifying the components in the noise sub-space. An additional example may include an envelope subtraction algorithm, which is based on the principle that the clean (noise-free) envelope may be estimated by subtracting a noisy envelope from the noise envelope, which may be separately estimated. Another example may include a method that utilizes S-shaped compression functions in place of the conventional logarithmic compression functions for noise suppression. In an alternative example, a binary masking algorithm may utilize features extracted from training data and categorizes each time-frequency region of a spectrogram as speech-dominant or noise-dominant. In another example, a wavelet-based noise reduction method may provide de-noising in a wavelet domain by utilizing shrinking and/or thresholding operations.

Although there have been many approaches to filtering and/or reducing noise in a noisy audio signal to a cochlear implant, there remains a dilemma in designing a noise reduction system and/or method that there may be a tradeoff between an amount of noise-reduction that can be provided as compared to signal distortion and/or speech distortion that may be introduced as a side-effect of filtering and/or noise reduction processes. In particular, a more aggressive noise removal process may introduce more distortion, and therefore, possibly less intelligibility in the resulting signal. Conversely, a mild approach to remove noise may result in less distortion, but the signal may retain more noise. Finding the optimal point where the distortion may be minimized, and the noise may be minimized requires careful balancing of the two factors and can be difficult. In particular, this optimal point may differ from person to person in both normal hearing people and in CI users. The exemplary embodiments described herein provide a method and system for noise reduction, particularly multi-talker babble noise reduction, that is believed to bypass this optimal point conundrum by applying both aggressive and mild noise removal methods at the same time and benefit from the advantages and avoid the disadvantages of both approaches.

Many de-noising problems can be summarized as:

$$Y=X+N \qquad (1)$$

where Y is the available noisy signal and X and N are the unknown target signal and the added noise, respectively. In fact, Y, X and N may be three arrays of real numbers where each element in Y is the sum of two numbers with the same index in X and N. If L is the length of each array, then solving (1) requires solving a system of equation with L equations and 2 L unknowns. Such a system in general has infinite sets of answers. Out of these infinite possible results, only one unique solution actually represents the original signal and noise. Hence in general de-noising is not about solving (1), it is mainly about choosing one unique X and one unique N, among unlimited possible solutions, which are the most accurate estimates of original X and N. In order to find this unique solution, there is a need to have some additional information about the signal or the noise, or preferably both.

There are many seemingly different de-noising methods which are developed for different kinds of signals and noises. However, there is one thing common among to them. They all assume or obtain at least some prior knowledge or information about original signal or noise (or both). This information may be used as a constraint (possibly a 'soft' constraint) on equation (1) and may help to find the desired unique answer. For example, each of the following statements could be considered as useful prior information which might help to find a unique answer for de-noising problem: signal or noise or both have a certain probability distribution function, signal or noise or both have a certain spectral behavior, signal or noise can be sparsely represented in a certain domain, etc. In general, either the signal or noise (or both) should have some known behavior or property that helps to distinguish and ultimately separate them.

In the case of babble noise reduction, equation (1) can be re-written in the form:

$$Y = S + B \quad (2)$$

where: Y is the noisy signal, S is the target or the desired speech, and B is the multi-talker babble noise in the background. As mentioned above, every de-noising method needs some prior information. Therefore, in order to design a babble noise reduction method, we need some prior information or assumptions. In a typical babble noise situation, it's reasonable and realistic to make the following three assumptions:

1. Babble comprises of multiple speech signals. In other words, equation (2) can be expanded as: $Y = S + \sum_{i=1}^{N_b} S_i$, where $S_1$ to $S_{N_b}$ are the individual background talkers which collectively form the multi-talker babble.
2. Target speech and background babble both consist of human speech.
3. Target speech is louder (has greater variance) than every individual background speech, i.e.:

$$\sigma_S^2 > \sigma_{S_i}^2 \; \forall 1 \leq i \leq N \quad (3)$$

Note that (3) does not mean that the energy of target speech ($E_S$) is necessarily greater than the energy of the multi-talker babble ($E_S$). In fact, it is possible that the Signal to Noise Ratio (SNR) is negative ($E_S < E_B$) while (3) still holds.

Based on these three assumptions, it is noted that:

The first assumption can be useful because it demonstrates that as opposed to the target speech, babble is made of multiple speech signals. This means that babble carries more information than the target speech. Hence features like entropy which measure the amount of information in a signal might be helpful to differentiate target speech from the babble.

The second assumption makes the problem more difficult rather than easier. Because target signal and babble have similar properties, it is more difficult to distinguish and differentiate them, compared to distinguishing target speech from stationary noise (non-babble).

The third assumption can be very useful. This is because it means that a sample of the target speech is more likely to have a larger amplitude than a sample of the babble. It means that thresholding (which in general is a way to separate large-amplitude samples from the small-amplitude samples) can be a potential candidate to solve the babble problem.

Even though thresholding can be a potential way to remove the babble, it is shown below that simple thresholding cannot solve such a complex problem. FIG. 1 shows the ineffectiveness of time-domain thresholding even when the noise level is known. As can be seen in the bottom plot, the original signal is highly distorted after thresholding. There are two reasons for ineffectiveness of simple temporal/spectral thresholding for babble reduction: First, babble and speech are highly overlapping in time and frequency. Second, some target speech coefficients are smaller than the threshold level and they will be attenuated or set to zero by thresholding. Moreover, in practice the noise level is not known, and thus a suitable threshold level cannot be estimated. As discussed further below, a second exemplary embodiment (e.g., SEDA-RT method) proposes to solve these problems by designing a classifier to estimate the noise level and applying complex thresholding in an oversampled wavelet domain to minimize the overlapping and distortion.

Noise Reduction Using Q-Factor Based Signal Decomposition (E.g., SEDA_i Method)

In a first embodiment, an exemplary method comprises a first step for decomposing a noisy signal into two components, which may also perform a preliminary de-noising of the signal at the same time. This first step for decomposing the noisy signal into two components may utilize any suitable signal processing methods. For example, this first step may utilize, one, two or more wavelet or wavelet-like transforms and a signal decomposition method, e.g., a sparsity based signal decomposition method, optionally coupled with a de-noising optimization method. In particular, this first step may utilize two Tunable Q-Factor Wavelet Transforms (TQWTs) and a sparsity based signal decomposition method coupled with applying a Basis Pursuit De-noising optimization method. Wavelets, sparsity based decomposition methods and de-noising optimization methods may be highly tunable. Therefore, their parameters may be adjusted to obtain desired features in output components. The output components of this first step may include two main products and a byproduct. The two main products may include a Low Q-factor (LQF) component and a High Q-factor (HQF) component, and the byproduct may include a separated residual noise, wherein the Q-factor may be a ratio of a pulse's center frequency to its bandwidth, which is discussed further below. In case of complex non-stationary noise, this first step for decomposing the noisy signal may not remove all of the noise. Therefore, the method may include a second step for de-noising using information from the products obtained from the first step.

Generally, a first embodiment of a method for noise reduction, particularly multi-talker babble noise reduction, e.g., a Speech Enhancement using Decomposition Approach_iterative version (SEDA_i), may comprise three different stages: (1) Noise level classification, (2) Signal decomposition and initial de-noising, and (3) Spectral cleaning and reconstitution. The first stage classifies the noise level of the noisy speech. The second stage decomposes the noisy speech into two components and performs a preliminary denoising of the signal. This is achieved using two Tunable Q-factor Wavelet Transforms (TQWTs) and a sparsity-based signal decomposition algorithm, Basis Pursuit De-noising (BPD). The wavelet parameters in the second stage will be set based on the results of the classification stage. The output of the second stage will consist of three components. The low Q-factor (LQF) component, the high Q-factor (HQF) component and the residual. The third stage further denoises the HQF and LQF components and then recombines them to produce the final de-noised output.

Figure 2A:
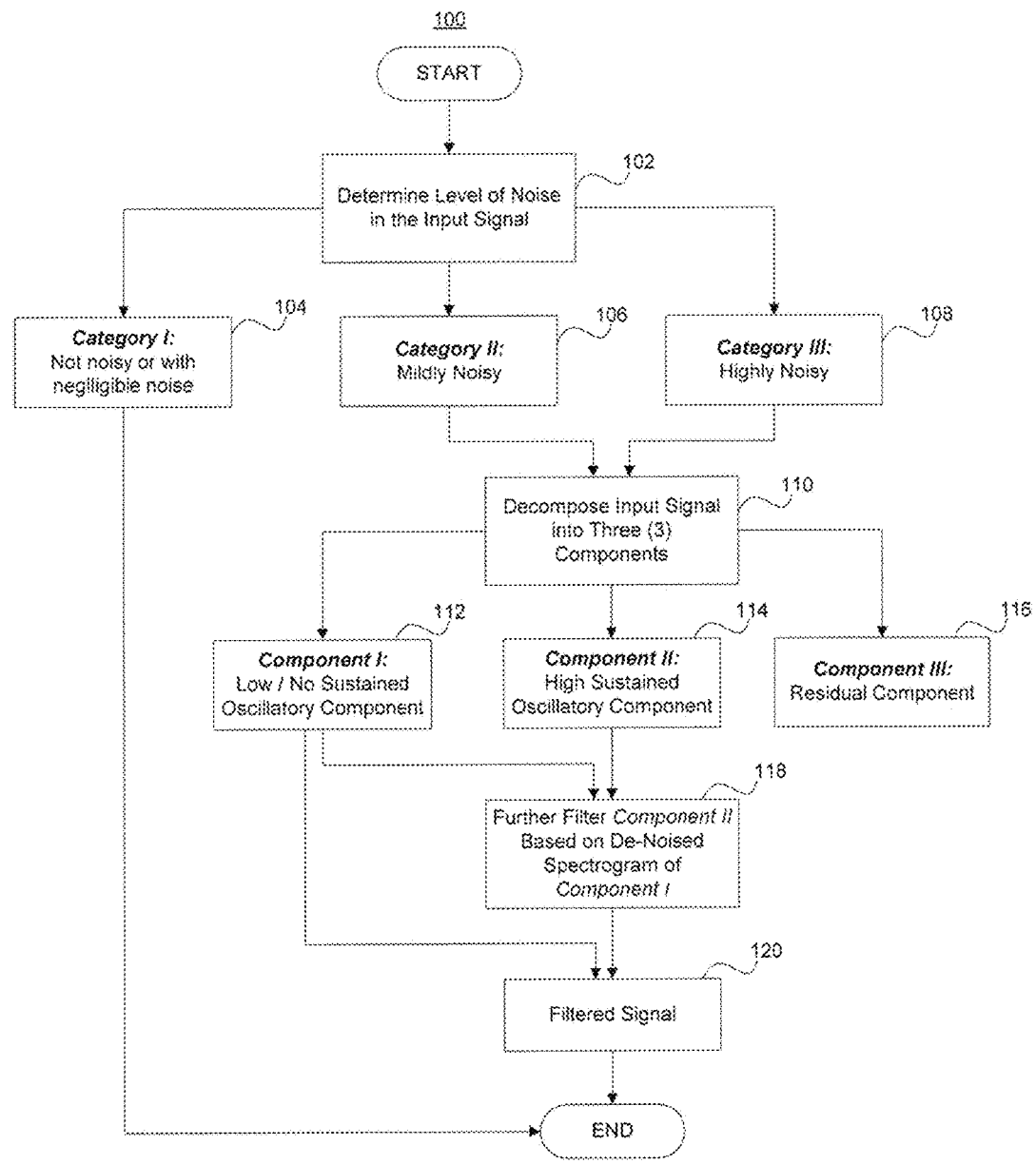
FIG. 2a shows an exemplary method for noise reduction, in particular, multi-talker babble noise reduction in a cochlear implant.

FIG. 2a illustrates a first exemplary method 100 for noise reduction, in particular, multi-talker babble noise reduction in a cochlear implant. Specifically, the method may be used to improve recognition and intelligibility of speech to patients in need of hearing assistance. Any suitable cochlear implant may be used with exemplary method 100. In particular, the cochlear implant may detect an audio signal and restore a deaf or partially deaf individual's ability to hear by providing an electrical stimulation to the auditory nerve corresponding to the audio signal. However, often the input audio signal may be noisy and cannot be recognized or discerned by the user. Therefore, the input signal may be further processed, e.g., filtered, to improve clarity and/or intelligibility of speech to the patient. In an exemplary embodiment, a rough determination of the noise level in the input signal may be determined before starting a de-noising process. In addition, the estimated level of noise present may be utilized to set a wavelet and optimizations parameters for subsequent de-noising of the input signal.

The input audio signal may be a continuous audio signal and may be broken down into predetermined segments and/or frames for processing by the exemplary method 100. In particular, in a real-time application, such as an application for improving hearing for a CI user or for improving intelligibility of audio communications on a communications device (such as mobile communications device, a telephone, a smart phone, etc.), the input signal may include non-steady noise where the level of noise, e.g., signal to noise ratio, may change over time. To adapt to the changing levels of noise intensity in an input signal, the signal may be separated into a plurality of frames of input signal, where each frame may be individually analyzed and/or de-noised, such as for example, processing each individual frame using the exemplary method 100. The input signal may be divided into the plurality of frames by any suitable means. The exemplary method 100 may be continuously applied to each successive frame of the input signal for analysis and/or de-noising. In some embodiments, the input audio signal may be obtained and each frame of the input audio signal may be processing by the exemplary method 100 in real-time or substantially real-time, meaning within a time frame that is negligible or imperceptible to a user, for example, within less than 3 seconds, less than 1 second, or less than 0.5 seconds.

In a first step 102, an input signal or a frame of an input signal may be obtained and analyzed to determine and/or estimate a level of noise present in the signal. Based on a level or an estimated level of noise present, the input signal or frame of input signal may be categorized into one of three categories: (I) the signal is either not noisy or has negligible amount of noise 104; (II) the signal is mildly noisy 106; or (Ill) the signal is highly noisy 108.

Step 102 may estimate the noise level in an input signal or a frame of an input signal using any suitable methods, such as, for example, methods for determining and/or estimating a signal to noise ratio (SNR), which may be adjusted to estimate the noise level in a variety of noise conditions. Any suitable SNR method may be used and may include, for example, those methods described in Hmam, H., "Approximating the SNR Value in Detection Problems," *IEEE Trans. on Aerospace and Electronic Systems VOL. 39, NO. 4* (2003); Xu, H., Wei, G., & Zhu, J. "A Novel SNR Estimation Algorithm for OFDM," *Vehicular Technology Conference, vol.* 5, 3068-3071 (2005); Mian, G., & Howell, T., "Determining a signal to noise ratio for an arbitrary data sequence by a time domain analysis," *IEEE Trans. Magn., Vol.* 29, No. 6 (1993); Liu, X., Jia, J., & Cai, L., "SNR estimation for clipped audio based on amplitude distribution," ICNC, 1434-1438 (2013), all of which are incorporated by reference herein. However, existing SNR estimation methods do not specifically accommodate non-stationary noise and therefore, typically suffer from some degree of error and computational costs. Alternatively, the noise level of an input signal or a frame of an input signal may be estimated by measuring a frequency and depth of modulations in the signal, or by analyzing a portion of the input signal in silent segments in speech gaps. It is noted that step 102 may determine a SNR for an input signal or a frame of an input signal, but may alternatively provide merely an estimate, even a rough estimate of its SNR.

The SNR or estimated SNR may be used to categorize the input signal or a frame of the input signal into the three different categories 104, 106, and 108. For example, Category I for a signal that is either not noisy or include negligible amounts of noise 104. In particular, this first category 104 may include, for example, those input signals or frames of input signals that have or are estimated to have a SNR that is greater than 12 dB (SNR>12 dB), or greater than or equal to 12 dB (SNR≥12 dB). The second category 106 may include, for example, those input signals or frames of input signals that have or are estimated to have a SNR that is greater than 5 dB and less than 12 dB (5 dB<SNR<12 dB), or greater than or equal to 5 dB and less than or equal to 12 dB (5 dB≤SNR≤12 dB). The third category 108 may include, for example, those input signals or frames of input signals that have or are estimated to have a SNR that is less than 5 dB (SNR<5 dB), or less than or equal to 5 dB (SNR≤5 dB).

This first step 102 does not depend highly on the accuracy of the noise level estimation, e.g., SNR estimation provided. Rather, for input signals having SNR values on or near the threshold values of 5 dB and 12 dB, categorization of such an input signal in either of the bordering categories is not expected to significantly alter the outcome of the exemplary de-noising method 100 of FIG. 2a. Therefore, estimated SNR values may be sufficient for the first step 102. In certain exemplary embodiments, estimated SNR values may be determined using a more efficient process, e.g., a method that requires less computational resources and/or time, such as by a process that requires fewer iterative steps.

In one particular embodiment, the SNR may be estimated using an exemplar SNR detection method for an arbitrary signal s, where s may be defined as $s=\{s_1, s_2, \ldots, s_n\}$. A ratio of the signal's root mean square (rms) after and/or before a thresholding with respect to τ(s) (which may be defined as $$\tau(s) = 3\frac{1}{n}\sum_{i=1}^{n} |s_i|),$$

may be represented by the term r(s,τ(s)). The ratio r(s,τ(s)) may be defined as:

$$r(s, \tau(s)) = \frac{h_{rms}(s, \tau(s))}{s_{rms}}$$

where $s_{rms} = \sqrt{\frac{1}{n}(s_1^2 + s_2^2 + \ldots + s_n^2)}$

And $h(s, \tau(s)) = \{h_1, h_2, \ldots, h_n\}$ where $h_i = \begin{cases} 0, & |s_i| \leq \tau(s) \\ s_i, & |s_i| > \tau(s) \end{cases}$ The term h(s,τ(s)) refers to signal s after hard thresholding with respect to τ(s). The term τ(s) may be defined such that for speech samples that are mixed with multi-talker babble, the value of r(s,τ(s)) varies little from signal to signal for samples having a constant a constant signal to noise ratio (SNR). In one specific embodiment, the term τ(s) for an arbitrary signal $s=\{s_1, s_2, \ldots, s_n\}$ is may be defined as shown below:

$$\tau(s) = 3\frac{1}{n}\sum_{i=1}^{n} |s_i|$$

The values of $r(x_1, \tau(x_1)), r(x_2, \tau(x_2)), \ldots, r(x_N, \tau(x_N))$ for a sufficiently large number, for example but not limited to (N=200), may be subsequently determined according to the following:

$$R_5 = \frac{\sum_{i=1}^{n} r(x_i, \tau(x_i))}{N}$$

wherein $x_1, x_2, \ldots, x_N$ correspond to a mixture of various speech samples taken from IEEE standard sentences (IEEE Subcommittee, 1969) and multi-taker babble with SNR=5.

The values for $r(y_1, \tau(y_1))$, $r(y_2, \tau(y_2))$, ..., $r(y_N, \tau(y_N))$ may be subsequently determined accordingly to the following:

$$R_{12} = \frac{\sum_{i=1}^{n} r(y_i, \tau(y_i))}{N}$$

wherein $y_1, y_2, \ldots, y_N$ correspond to a mixture of various speech samples taken from IEEE standard sentences (IEEE Subcommittee, 1969) and multi-taker babble with SNR=12.

An input signal s with an unknown SNR may be categorized into one of the three different categories 104, 106, and 108 as follows:

$$C(s) \in \begin{cases} 104\ (SNR > 12), & R_{12} < r(s, \tau(s)) \\ 106\ (5 < SNR < 12), & R_5 \leq r(s, \tau(s)) \leq R_{12} \\ 108\ (SNR < 5), & r(s, \tau(s)) < R_5 \end{cases}$$

C(s): Signal's s category based on its SNR

As discussed above, this exemplary SNR estimation method in the first step 102 need not provide accurate estimates of SNR. Rather, it serves to categorize the input signals or frames of input signals into various starting categories prior to further analysis and/or de-noising of the input signals or frames of input signals. This pre-processing categorization in step 102 is particularly beneficial for input signals or frames of input signals containing multi-talker babble. It is further contemplated that this first step 102 utilize any suitable method to categorize the input signals or frames of input signals into a plurality of categories, each having a different noise level. More particularly, the first step 102 may encompass any fast and efficient method for categorizing the input signals or frames of input signals into a plurality of categories having different noise levels.

In the exemplary embodiment shown in FIG. 2a, input signals or frames of input signals that fall within the first category 104 do not contain substantial amounts of noise. Therefore, these input signals or frames of input signals are too clean to be de-noised. The intelligibility of input signals in this first category 104 may be relatively high, therefore further de-noising of the signal may introduce distortion and/or lead to no significant intelligibility improvement. Accordingly, if the input signal or frame of input signal is determined to fall within the first category 104, the method 100 terminates without modification to the input signal or the frame of the input signal.

Input signals or frames of input signals that fall within the second category 106 may be de-noised in a less aggressive manner as compared to noisier signals. For input signals or frames of input signals in the second category 106, the priority is to avoid de-noising distortion rather than to remove as much noise as possible.

Input signals or frames of input signals that fall within the third category 108 may not be very intelligible to a CI user, and may not be intelligible at all to an average CI user. For input signals or frames of input signals in the third category 108, distortion is less of a concern compared to intelligibility. Therefore, a more aggressive de-noising of the input signal or frame of input signal may be performed on input signals of the third category 108 to increase the amount of noise removed while gaining improvements in signal intelligibility to the CI user.

Input signals or frames of input signals that fall within either the second category 106 or the third category 108 may be further processed in step 110. In step 110, the input signals or frames of input signals may be decomposed into at least two components: (I) a first component 112 that exhibits no or low amounts of sustained oscillatory behavior; and (II) a second component 114 that exhibits high sustained oscillatory behavior. Step 110 may optionally decompose the input signals or frames of input signals to include a third component: (III) a residual component 116 that does not fall within either component 112 or 114. Step 110 may decompose the input signals or frames of input signals using any suitable methods, such as, for example, separating the signals into components having different Q-factors. The Q-factor of a pulse may be defined as a ratio of its center frequency to its bandwidth, as shown in the formula below:

$$Q = \frac{\omega_c}{BW}.$$

For example, the first component 112 may correspond to a low Q-factor component and the second component 114 may correspond to a high Q-factor component. The second component 114, which corresponds to a high Q-factor component, may exhibit more sustained oscillatory behavior than the first component 112, which corresponds to a low Q-factor component.

Suitable methods for decomposing the input signals or frames of input signals may include a sparse optimization wavelet method. The sparse optimization wavelet method may decompose the input signals or frames of input signals and may also provide preliminary de-noising of the input signals or frames of input signals. The sparse optimization wavelet method may utilize any suitable wavelet transform to provide a sparse representation of the input signals or frames of input signals. One exemplary wavelet transform that may be utilized with a sparse optimization wavelet for decomposing the input signals or frames of input signals in step 100 may include a Tunable Q-Factor Wavelet Transform (TQWT). In particular, the TQWT may be determined based on a Q-factor, a redundancy rate and a number of stages (or levels) utilized in the sparse optimization wavelet method, each of which may be independently adjustable within the method. By adjusting the Q-factor, the oscillatory behavior of the TQWT may be modified. In particular, the Q-factor may be adjusted such that the oscillatory behavior of the TQWT wavelet matches that of the input signals or frames of input signals. Redundancy rate in a wavelet transform, e.g., a TQWT, may refer to a total over-sampling rate of the transform. The redundancy rate must be always greater than 1. Because the TQWT is an over-sampled wavelet transform, any given signal would not correspond to a unique set of wavelet coefficients. In other words, an inverse TQWT applied to two different sets of wavelet coefficients, may correspond to the same signal.

Step 110 may also provide preliminary de-noising of the input signals or frames of input signals. The preliminary de-noising may be performed by a sparsity-based de-noising method, such as, for example, a sparse optimization wavelet method. As discussed above, of the input signals or frames of input signals may be represented by any suitable wavelet, in particular TQWT. By adjusting the Q-factor, an optimal sparse representation of the input signals or frames of input signals may be obtained. Such an optimal sparse representation may provide improved performance for related sparsity-based methods such as signal decomposition and/or de-noising. To select a spare representation of the input signals or frames of input signals, a Basis Pursuit (BP) method may be used. In particular, if the input signals or frames of input signals are considered to be noisy, e.g., those falling within the third category 109, a Basis Pursuit De-noising (BPD) method may be used.

Human speech may exhibit mixture of oscillatory and non-oscillatory behaviors. These two components usually cannot be sparsely represented using only one TQWT. Therefore in step 110, each input signal or frame of input signal may be represented using two different components having two different Q-factors. Suitable methods for decomposing the input signals or frames of input signals in step 110 may also include, for example, a Morphological Component Analysis (MCA) method.

In one particular exemplary embodiment, the input signal or frame of input signal Y may be decomposed into three components: (I) a first component 112 having a low Q-factor $x_1$, which does not exhibit sustained oscillatory behavior, (II) a second component 114 having a High Q-factor component $x_2$, which exhibits sustained oscillatory behavior, and (III) a residual component 116 represented by n, which includes noise and stochastic unstructured signals that cannot be sparsely represented by either of the two wavelet transforms of the first and second components 112 and 114. The input signal Y may be represented as follows:

$$y = x_1 + x_2 + n.$$

The decomposition of the input signal y, as shown above, may be a nonlinear decomposition, which cannot be achieved by any linear decomposition methods in time or frequency domain. Therefore, a MCA method may be used to obtain a sparse representation of both the first and second components 112, 114, where $x_1$ and $x_2$ may be obtained using a constrained optimization method using the following formula:

$$\operatorname{argmin}_{w_1, w_2} \|y - \phi_1^{-1} w_1 - \phi_2^{-1} w_2\|_2^2 + \sum_{j=1}^{J_1+1} \lambda_{1,j} \|w_{1,j}\|_1 + \sum_{j=1}^{J_2+1} \lambda_{2,j} \|w_{2,j}\|_1$$

such that: $y = \Phi_1^{-1}(w_1) + \Phi_2^{-1}(w_2) + n$
wherein $\Phi_1$ and $\Phi_2$ are TQWT with low and high Q-factors respectively, $\lambda_{1,j}$ and $\lambda_{2,j}$ are subband-dependent regularizations and should be selected based on the intensity of the noise, j is the subband index and $\Phi_1^{-1}$ and $\Phi_2^{-1}$ are the inverse of the first and second tunable wavelet transforms.

The above formula may be solved to obtain $w_{1,j}$ and $w_{1,j}$, which are the wavelet coefficients in different subbands. Using the wavelet coefficients, $w_1$ and $w_2$, the first and second components 112 and 114, as represented by $x_1$ and $x_2$, may be obtained as follows:

$$x_1 = \Phi_1^{-1}(w_1), x_2 = \Phi_2^{-1}(w_2)$$

In one particular exemplary embodiment, the wavelet and optimization parameters may also be selected such that the first and second components 112, 114 are also preliminarily de-noised using a BPD method. In particular, the wavelet and optimization parameters may be selected such that the following conditions are met:

(1) The first component 112, which is the Low Q-factor (LQF) component, have significantly lower energy than the second component 114, which is the high Q-factor (HQF) component; and (2) The LQF be de-noised more aggressively, and consequently may be more distorted.

Because the LQF may be de-noised more aggressively, the HQF would be de-noised more mildly to reduce the amount of distortion. The two conditions above allow for identification of the HQF and LQF that typically have relatively similar Temporal and Spectral Pattern (TSP) when the signal is not noisy. In other words, the concentration of the energy in these spectrograms and time domain graphs are expected to be roughly in the same areas. The input signal or frame of input signal may be decomposed based on the Q-factors of different components, and that the input signals or frames of input signals that share similar frequency content may correspond to different Q-factors.

In step 118, the second component 114 may be further de-noised using the first component 112 or data generated based on the first component 112. As explained further below, the TSP of the first component 112 is expected to more closely resemble that of a clean speech signal, as compared to the second component 114. Therefore, the first component 112 may be used to further de-noise the second component 114, particularly using the TSP of the first component.

A clean audio signal that is not noisy may be represented by X. For a clean input signal X, BPD is not necessary for de-noising the signal. Therefore, decomposition of a clean input signal X may be correspond to a spare representation of two components, where $x_1$ and $x_2$ may be obtained using a constrained optimization method using the following formula:

$$\arg\min_{w_1, w_2} \Sigma_{j=1}^{J_1+1} \lambda_{1,j} \|w_{1,j}\|_1 + \Sigma_{j=1}^{J_2+1} \lambda_{2,j} \|w_{2,j}\|_1$$

such that: $x = \Phi_1^{-1}(w_1) + \Phi_2^{-1}(w_2)$
and: $x_1 = \Phi_1^{-1}(w_1), x_2 = \Phi_2^{-1}(w_2)$
where: $x = x_1 + x_2$.

Both the noisy input signal or frame of input signal Y and the clean input signal X may be decomposed into HQF and LQF components are follows:

$$Y = X + N$$

wherein $X = X_L + X_H$, and
wherein $Y = Y_L + Y_H + N_1$.
Each of the above variables are defined as follows:
Y: Noisy speech signal
X: Clean speech signal before adding noise
N: Added noise
$X_L$: LQF component of the original speech signal
$X_H$: HQF component of the original speech signal
$Y_L$: LQF component of the noisy speech signal
$Y_H$: HQF component of the noisy speech signal
$N_1$: Residual component of the decomposition using BPD Because the LQF component $Y_L$ is expected to include less noise than HQF component $Y_H$ due to a more aggressive noise removal in step 110, the TSP of the LQF component $Y_L$ is expected to be more similar to the TSP of the LQF component $X_L$ of the clean speech signal. This similarity is particularly notable in lower frequencies where speech fundamental frequencies are often located. Therefore, the concentration of energy in both their spectrograms are expected to follow a similar shared pattern. Gaps and speech pauses are also expected to be located at the same areas of the spectrograms and time domain graphs in both cases. The term gaps, as used herein, refers to empty or low energy areas in low frequency parts of the spectrograms or very low amplitude pauses in time domain graphs.

In contrast, the HQF component $Y_H$, which is de-noised less aggressively in step 110, is expected to be noisier and therefore, less similar to HQF component $X_H$ of the clean speech. Contrary to the LQF components $Y_L$ and $X_L$ discussed above where gaps could be seen in both noisy and clean spectrograms, all low frequency gaps which could be identified in clean signal's HQF component $X_H$ may be filled, typically completely filled, by noise in the HQF component $Y_H$ of the input signal or frame of input signal. Although the signal may include more noise, the HQF component $Y_H$ is expected to be less distorted, which is particularly crucial for good intelligibly to a patient. Because the LQF and HQF components of the clean speech, $X_L$ and $X_H$, are also expected to have roughly similar TSPs (at least the gaps in low frequencies in their spectrograms are roughly in the same areas), it is expected that the TSP of the HQF component $X_H$ of the clean speech also bears some similarities to the TSP of the LQF component $Y_L$ obtained from noisy input signal. This resemblance may be more pronounced in time domain graphs. The low frequency gaps in the time domain graphs may also be similar, at least compared to the noisy HQF component $Y_H$.

In step 118, the input signal or frame of input signal Y should be de-noised such that it becomes as similar as possible to the clean speech X without causing too much distortion. As discussed above, the LQF components of clean speech and noisy speech are already similar, and therefore, only the HQF component of the noisy input signal needs to be further modified (e.g., de-noised) so that it more closely resembles the HQF component of the clean speech ($X_H$).

The second component 114 may be further de-noised and may be represented by $\hat{Y}_H$, which corresponds to a modified version of $Y_H$ having a TSP that is similar to TSP of $X_H$, which may be represented as follows:

$$\mathcal{P}(\hat{Y}_H) \sim \mathcal{P}(X_H)$$

The further de-noised $\hat{Y}_H$ may be determined using the following formula:

$$\mathcal{P}(Y_L) \sim \mathcal{P}(X_L) \;\&\; \mathcal{P}(\hat{Y}_H) \sim \mathcal{P}(X_H) \Rightarrow \mathcal{P}(Y_L + \hat{Y}_H) \sim \mathcal{P}(X_L + X_H) \Rightarrow \mathcal{P}(Y_L + \hat{Y}_H) \sim \mathcal{P}(X)$$

Specifically, the first component 112 may correspond to $Y_L$ and the second component 114 may correspond to $Y_H$ in the formula shown above. Because $\mathcal{P}(\hat{Y}_H)$ is expected to be similar to $\mathcal{P}(X_H)$ and in the absence priori knowledge of $X_H$, the TSP of $Y_H$ may be modified and a modified version corresponding to version $\hat{Y}_H$ may be obtained to satisfy the following condition:

$$\mathcal{P}(\hat{Y}_H) \sim \mathcal{P}(Y_L)$$

Therefore, the further de-noised $\hat{Y}_H$ may be determined based on the following formula:

$$\mathcal{P}(Y_L) \sim \mathcal{P}(\hat{Y}_H) \;\&\; \mathcal{P}(Y_L) \sim \mathcal{P}(X_H) \Rightarrow \mathcal{P}(\hat{Y}_H) \sim \mathcal{P}(X_H)$$

In another exemplary embodiment, step 118 may include a method which modifies the spectrograph of the second component 114, e.g., $Y_H$, to a modified version of the second component, e.g., $\hat{Y}_H$. In particular, the method may prefer-ably introduce the least possible amount of distortion to the resulting output, and/or may provide processing of input signals in real-time or substantially real-time as to be useful in applications such as cochlear implant devices. In particular, the method for modifying the spectrograph of the second component 114, e.g., $Y_H$, to a modified version of the second component, e.g., $\hat{Y}_H$ may include point-wise multiplication of a Fourier transform domain of non-overlapping frames of an input signal. In particular, each frame of the input signal may be represented as $Y_i \in \mathbb{R}^N$, wherein N corresponds to a length of the frame. Each frame of the input signal may be represented may correspond to the following:

$$Y_L = Y_L + Y_H + Y_H + N_1$$

A Discrete Fourier Transform may be determined for each of the above components as follows:

$$Y_L^f = DFT\{Y_L\} = [Y_{L,1}^f, Y_{L,2}^f, \ldots, Y_{L,N}^f]$$

$$Y_H^f = DFT\{Y_H\} = [Y_{H,1}^f, Y_{H,2}^f, \ldots, Y_{H,N}^f]$$

Each point in $Y_L^f$ and $Y_H^f$ may be categorized as one of the following:

$$Y_{L,i}^f \in \begin{cases} C_{HH}: & |Y_{L,i}^f| \geq \alpha_1 Y_{L,m}^f \\ C_H: & \alpha_2 Y_{L,m}^f \leq |Y_{L,i}^f| \leq \alpha_1 Y_{L,m}^f \\ C_L: & \alpha_3 Y_{L,m}^f \leq |Y_{L,i}^f| \leq \alpha_2 Y_{L,m}^f \\ C_{LL}: & |Y_{L,i}^f| \leq \alpha_3 Y_{L,m}^f \end{cases}$$

$$Y_{H,i}^f \in \begin{cases} C_{HH}: & |Y_{H,i}^f| \geq \beta_1 Y_{H,m}^f \\ C_H: & \beta_2 Y_{H,m}^f \leq |Y_{H,i}^f| \leq \beta_1 Y_{H,m}^f \\ C_L: & \beta_3 Y_{H,m}^f \leq |Y_{H,i}^f| \leq \beta_2 Y_{H,m}^f \\ C_{LL}: & |Y_{H,i}^f| \leq \beta_3 Y_{H,m}^f \end{cases}$$

where:

$C_{HH}$, $C_H$, $C_L$, $C_{LL}$ represents four different categories corresponding to: very high energy, high energy, low energy and very low energy;

$$Y_{L,m}^f: \frac{\sum_{i=1}^{N} |Y_{L,i}^f|}{N}, \; Y_{H,m}^f: \frac{\sum_{i=1}^{N} |Y_{H,i}^f|}{N}$$

$$\alpha_3 < \alpha_2 < \alpha_1, \beta_3 < \beta_2 < \beta_1$$

The above categorization may be performed using a threshold-based quantification method. The TSP of the $Y_L^f$ is expected to be similar to TSP of $Y_H^f$ after removing the noise. Therefore, if a point demonstrates a high or very high energy in $Y_H^f$ but demonstrates low or very low energy in $Y_L^f$, its energy in $Y_H^f$ is believe to most likely be coming from a noise source and must then be attenuated.

To estimate $\hat{Y}_H^f$, each point in $Y_H^f$ may be compared with its counterpart in $Y_L^f$ and different reduction gains $g_r$ may be applied to high or very high energy points in $Y_H^f$ with low or very low energy counterparts in $Y_L^f$, which may be represented in the following formula:

$$\hat{Y}_{H,i}^f = \begin{cases} g_{r1} Y_{H,i}^f: & Y_{H,i}^f \in C_{HH}, Y_{L,i}^f \in C_{LL} \\ g_{r2} Y_{H,i}^f: & Y_{H,i}^f \in C_{HH}, Y_{L,i}^f \in C_L \\ g_{r3} Y_{H,i}^f: & Y_{H,i}^f \in C_H, Y_{L,i}^f \in C_{LL} \\ g_{r4} Y_{H,i}^f: & Y_{H,i}^f \in C_H, Y_{L,i}^f \in C_L \\ Y_{H,i}^f: & \text{Otherwise} \end{cases}$$

where: $0 < g_{r1} < g_{r2} \approx g_{r3} < g_{r4} \approx 1$.

In some embodiments, a reduction gain may be applied to low or very low energy points in $Y_H^f$. After an estimate for $\hat{Y}_H^f$ is obtained, an inverse Discrete Fourier Transform may be applied to obtain a modified version of the second component, e.g., $\hat{Y}_H$, of the input signal, as follows:

$$\hat{Y}_H = DFT^{-1}\{\hat{Y}_H^f\}$$

In step 120, the first component 112 and a further filtered second component, where the second component 114 is filtered using the first component 114, may be combined to generate a filtered signal that may be outputted for use in a cochlear. In particular, the first component 112, e.g., $Y_L$, and the further filtered second component, e.g., $\hat{Y}_H$, may be combined to create an output signal, as represented by $Y_O$, as follows:

$Y_{Out} = Y_L + \hat{Y}_H$, which is expected to demonstrate a TSP that is similar to the TSP of clean speech.

Figure 2B:
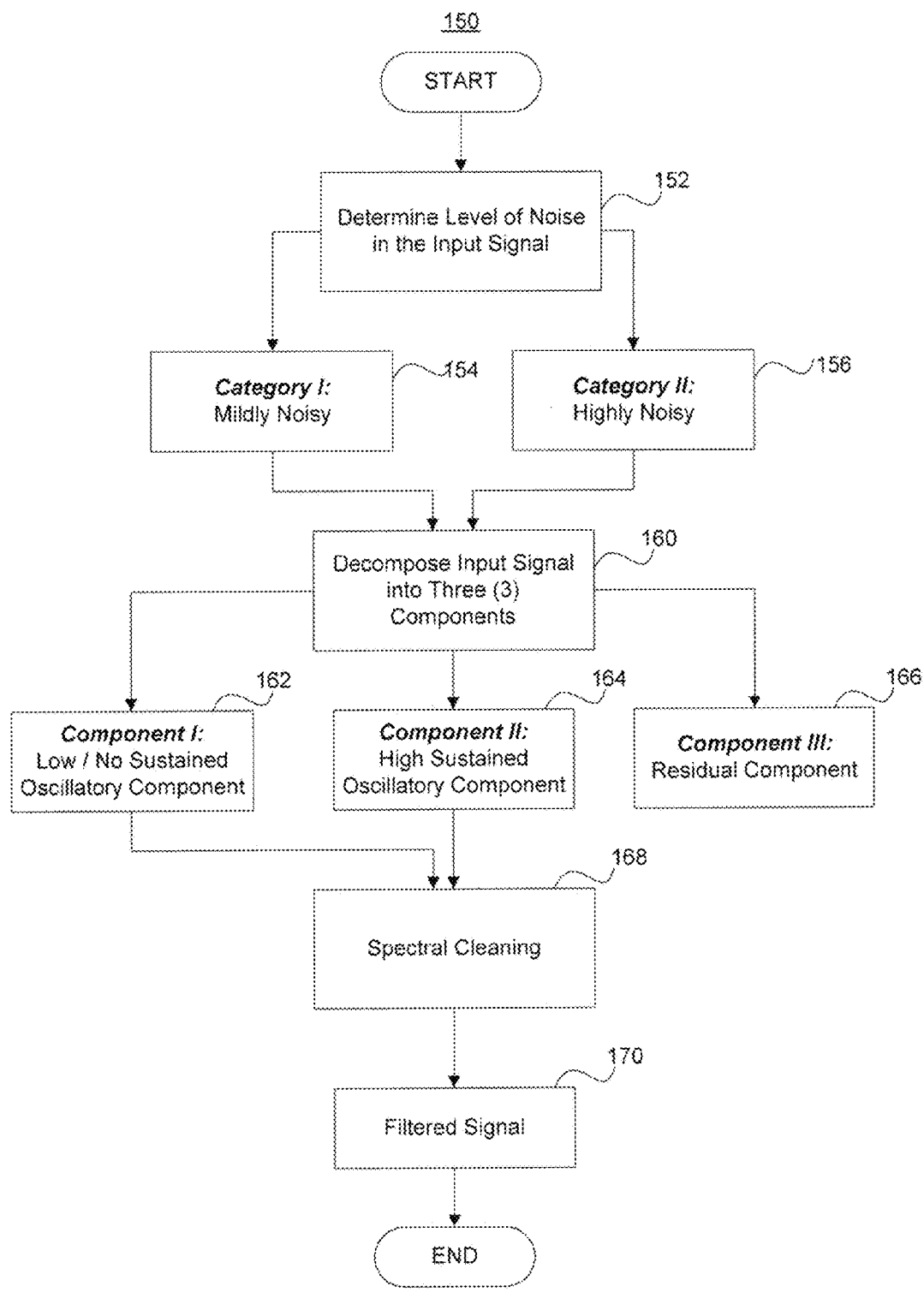
FIG. 2b shows an alternative exemplary method for noise reduction, in particular, multi-talker babble noise reduction in a cochlear implant.

FIG. 2b provides an alternative exemplary embodiment of a method 150 for noise reduction, in particular, multi-talker babble noise reduction in a cochlear implant. The alternative exemplary embodiment of method 150 shown in FIG. 2a is substantially similar to the method 100 describe with respect to FIG. 2b as discussed above. Differences between the two exemplary methods 100 and 150 are further detailed below.

Similar to step 102, in a first step 152, an input signal or a frame of an input signal may be obtained and analyzed to determine and/or estimate a level of noise present in the signal. Based on a level or an estimated level of noise present, the input signal or frame of input signal may be categorized into one of three categories: (1) the signal is either mildly noisy 154; or (II) the signal is highly noisy 156. Step 152 may estimate the noise level in an input signal or a frame of an input signal using any suitable methods, such those described above in reference to step 10 (e.g., methods for determining and/or estimating SNR).

In method 152, the SNR or estimated SNR may be used to categorize the input signal or a frame of the input signal into the two instead of three different categories 154 and 156. For example, Category I for a signal that is mildly noisy 154. In particular, this first category 154 may include, for example, those input signals or frames of input signals that have or are estimated to have a SNR that is greater than 3.5 dB (SNR>3.5 dB), or greater than or equal to 3.5 dB (SNR≥3.5 dB). The second category 156 may include, for example, those input signals or frames of input signals that have or are estimated to have a SNR that is less than 3.5 dB (SNR<3.5 dB), or less than or equal to 3.5 dB (SNR≤3.5 dB).

In one embodiment, the SNR may be estimated using the exemplary SNR detection method described above in reference to step 102. In another embodiment, the SNR may be estimated using a different exemplary method. This method may provide a computationally efficient and relatively accurate method to classify the noise level of speech corrupted by multi-talker babble. To keep track of the background noise variation, longer signals may be segmented into shorter frames and each frame may be classified and de-noised separately. The length of each frame should be at least one second to ensure a high classification/de-nosing performance. In this embodiment, step 152 uses two features which are sensitive to changes of the noise level in speech, easy to extract and relatively robust for various babble noise conditions (i.e., different number of talkers, etc.).

The first feature is the envelope mean-crossing rate which is defined as the number of times that the envelope crosses its mean over a certain period of time (e.g., one second). To compute this feature, step 152 first needs to extract the envelope of the noisy speech. For noisy speech frame Y the envelope can be obtained as follows:

$$E(n) = \frac{1}{l} \sum_{i=-\frac{l}{2}}^{\frac{l}{2}} |Y(i + n l_h)| w(i)$$

where, l is the length of the window (w) and $l_h$ is the hop size. The envelope mean-crossing rate of a noisy signal frame is calculated as follows:

$$f_1 = \frac{N}{2 f_s l_e} \sum_{i=2}^{l_e} |S(E(k) - M) - S(E(k-1) - M)|$$

where, E, $l_s$ and M are the envelope and its length and mean respectively, N is the length of the frame, $f_s$ is the sampling rate and S(x) is the sign function defined as:

$$S(x) = \begin{cases} 1, & x > 0 \\ -1, & x < 0 \\ 0, & x = 0 \end{cases}$$

Note that in for this feature we have used rectangular windows hence we have $l_h = 1$.

The main parameter that affects this feature is the length of the window (l). This feature may be optimized by finding the value of $l \in \mathbb{N}$ which maximizes the feature's Fischer score:

$$\mathrm{argmax}_{l \in N} \frac{\sum_{k=1}^{C_n} n_k (\mu_k - \mu)^2}{\sum_{j=1}^{C_n} n_k \sigma_k^2}$$

where, $C_n = 2$ is the number of classes, $\mu_k$ is the mean $f_1$ values of frames in class k, $\mu$ is the $f_1$ values overall mean, $\sigma_k$ is the $f_1$ values variance in class k and $n_k$ is the total number of frames in class k.

To numerically solve the above, this feature's Fischer score may be calculated for 10,000 labeled noisy speech frames corrupted with randomly created multi-talker babble. The duration of each noisy speech frame may be randomized between 2-5 seconds with sampling rate of $f_s = 16000$ samples/second. The average Fischer score for this feature may be maximized with l=50.

The second feature is post-thresholding to pre-thresholding RMS ratio. First we denote hard threshold of a noisy speech frame $Y = \{y_1, y_2, \ldots, y_n\}$, with threshold $\tau$ by $h(Y, \tau) = \{h_1, h_2, \ldots, h_n\}$ where: $h_i = \begin{cases} 0, & |y_i| \leq \tau \\ y_i, & |y_i| > \tau \end{cases}$ Post-thresholding to pre-thresholding RMS ratio is calculated as follows:

$$f_2 = \frac{\left\| h\left(Y, \frac{1}{n} K \|Y\|_1\right) \right\|}{\|Y\|}$$

The variable which determines the quality of this feature is K and this feature may be optimized by finding the value of K which maximizes the Fischer score for this feature:

$$\operatorname{argmax}_{K \in \mathbb{R}} \frac{\sum_{k=1}^{C_n} n_k (\mu_k - \mu)^2}{\sum_{j=1}^{C_n} n_k \sigma_k^2}$$

Numerical maximization of Fischer score with $K=0.1 \times \alpha$ where $\forall 1 \leq i \leq 100, \alpha \in \mathbb{N}$, shows the best value for K is K=3.

For training the classifier, the Gaussian Mixture Model (GMM) may be used. A GMM is the weighted sum of several Gaussian distributions:

$p(F|\mu,\alpha,\Sigma) = \sum_{i=1}^{Ng} \alpha_i \mathcal{N}(F|\mu_i,\Sigma_i)$ Such that $\sum_{i=1}^{Ng} \alpha_i = 1$.

where F is a d-dimensional feature vector (in this classification problem we have only two dimensions or d=2), $\alpha_i$ is the weight factor, $\mu_i$ is the mean and $\Sigma_i$ is the covariance of the ith Gaussian distribution. A Gaussian distribution $\mathcal{N}(F|\mu_i,\Sigma_i)$ can be written as:

$$\mathcal{N}(F|\mu_i, \Sigma_i) = -\frac{1}{(2\pi)^{\frac{d}{2}} \sqrt{|\Sigma_i|}} e^{\left(-\frac{1}{2}[F-\mu_i]^T \Sigma_i^{-1} [F-\mu_i]\right)}$$

Similar to step 102, step 152 also does not depend highly on the accuracy of the noise level estimation, e.g., SNR estimation provided. Rather, for input signals having SNR values on or near the threshold value of 3.5 dB, categorization of such an input signal in either of the categories is not expected to significantly alter the outcome of the exemplary de-noising method 152 of FIG. 2b. Therefore, estimated SNR values may also be sufficient for step 152. In certain exemplary embodiments, estimated SNR values may be determined using a more efficient process, e.g., a method that requires less computational resources and/or time, such as by a process that requires fewer iterative steps.

In the exemplary embodiment shown in FIG. 2b, input signals or frames of input signals that fall within the first category 154 may be de-noised in a less aggressive manner as compared to noisier signals. For input signals or frames of input signals in the second category 156, the priority is to avoid de-noising distortion rather than to remove as much noise as possible. The data samples may be divided between each of the two categories into two clusters and each cluster may be modeled by a Gaussian model. In order to train the model, the Expectation-Maximization (EM) algorithm may be used.

After training the classifier having the above, the method 150 may classify each test noisy speech frame Y with feature set F={$f_1,f_2$} using MAP (Maximum a posteriori estimation) as follows:

Y $\in \begin{cases} \text{Class 1 } (SNR \leq 3.5), & P(F|\text{Class 1})P(\text{Class 1}) > \\ & P(F|\text{Class 2})P(\text{Class 2}) \\ \text{Class 2 } (SNR > 3.5), & P(F|\text{Class 2})P(\text{Class 2}) > \\ & P(F|\text{Class 1})P(\text{Class 1}) \end{cases}$ $P(F|\text{Class 1}) = \alpha_1 \mathcal{N}(F|\mu_1,\Sigma_1) + \alpha_2 \mathcal{N}(F|\mu_2,\Sigma_2)$ $P(F|\text{Class 2}) = \alpha_3 \mathcal{N}(F|\mu_3,\Sigma_3) + \alpha_4 \mathcal{N}(F|\mu_4,\Sigma_4)$.

where; $\alpha_1, \alpha_2, \mu_1, \mu_2, \Sigma_1, \Sigma_2$ are GMM parameters of class 1 and $\alpha_3, \alpha_4, \mu_3, \mu_4, \Sigma_3, \Sigma_4$ are GMM parameters of class 2. Here both classes may be assumed to have equal overall probability (i.e., P(class$_1$)=P(class$_2$)=0.5). Note that for each Gaussian model, the method 150 has already obtained the values of $\mu_i$, $\Sigma_i$ and $\alpha_i$ from the EM method. Using MAP, for each noisy speech sample with feature vector F, two probabilities we may be obtained and the noisy sample may be classified into the class with the higher probability.

Input signals or frames of input signals that fall within either the first category 154 or the second category 156 may be further processed in step 160 in a similar manner as step 110 described above. In step 160, the input signals or frames of input signals may be decomposed into at least two components: (I) a first component 162 that exhibits no or low amounts of sustained oscillatory behavior; and (II) a second component 164 that exhibits high sustained oscillatory behavior. Step 160 may optionally decompose the input signals or frames of input signals to include a third component: (III) a residual component 166 that does not fall within either components 162 or 164. Step 160 may decompose the input signals or frames of input signals using any suitable methods, such as, for example, separating the signals into components having different Q-factors.

Step 160 may similarly provide preliminary de-noising of the input signals or frames of input signals. The preliminary de-noising may be performed by a sparsity-based de-noising method, such as, for example, a sparse optimization wavelet method. As discussed above, of the input signals or frames of input signals may be represented by any suitable wavelet, in particular TQWT. By adjusting the Q-factor, an optimal sparse representation of the input signals or frames of input signals may be obtained. Such an optimal sparse representation may provide improved performance for related sparsity-based methods such as signal decomposition and/or de-noising. To select a spare representation of the input signals or frames of input signals, a Basis Pursuit (BP) method may be used. In particular, if the input signals or frames of input signals are considered to be noisy, e.g., those falling within the third category 109, a Basis Pursuit De-noising (BPD) method may be used.

In step 168, the different HQF and LQF components may be further de-noised (e.g., by spectral cleaning) and subsequently recombined to produce the final de-noised output 170. In particular, this further de-noising step 168 may include parameter optimization followed by subsequent spectral cleaning. For example, assuming that the clean speech sample X and its noisy version Y are available, they may be each decomposed into HQF and LQF components. There are a total 8 parameters associated with the optimization problem discussed above in steps 110 and 160. In order to maximize the de-noising performance in this stage each of these eight parameters are optimized to ensure maximal noise attenuation with minimal signal distortion.

Low and high Q-factors ($Q_1$ and $Q_2$): These two parameters should be selected to match the oscillatory behavior of the speech in order to attain high sparsity and efficient subsequent denoising. $Q_1$ and $Q_2$ denote the low and high Q-factors, respectively. Hence $Q_2$ must be sufficiently larger than $Q_1$. Choosing close values for $Q_1$ and $Q_2$ will lead to very similar LQF and HQF components and poor sparsification. Conversely setting $Q_2$ to be too much greater than $Q_1$ also leads to poor results due to the concentration of most of the signal's energy in one component. With $Q_1=1$, any value between 5 to 7 is a reasonable choice for $Q_2$. In one exemplary embodiment, $Q_1=1$ and $Q_2=5$.

Oversampling rates ($r_1$ and $r_2$): a sufficient oversampling rate (redundancy) is required for an optimal sparsification. Nevertheless, selecting large oversampling values will increase the computational cost of the algorithm. For this method, any number between 2-4 can be suitable for $r_1$ and $r_2$. In one exemplary embodiment, $r_1=r_2=3$.

Number of levels ($j_1$ and $j_2$): Once the previous four parameters are chosen, $j_1$ and $j_2$ should be selected to ensure the distribution of wavelet coefficient in a sufficiently large number of sub-bands. In one exemplary embodiment, $j_1=10$, $j_2=37$.

After selecting suitable values for wavelet parameters, the regularization parameters $\lambda_1$ and $\lambda_2$ may be adjusted. These two parameters directly influence the effectiveness of denoising. A larger value for either of them will lead to a more aggressive de-noising for its corresponding component. A more aggressive de-noising will potentially lead to more noise removal but usually at the expense of increasing the distortion of the denoised speech. Choosing suitable values for $\lambda_1$ and $\lambda_2$ which ensure the maximum noise removal with minimum distortion is crucial for this stage.

Assuming the clean speech sample X is available, $\lambda_1$ and $\lambda_1$ may be selected, which maximize the similarity between the spectrograms of the clean speech components ($X_L$ and $X_H$) and their de-noised versions ($Y_L$ and $Y_H$). To measure the similarity between the spectrograms of the clean and de-noised signals, the normalized Manhattan distance applied to the magnitude of the spectrograms (e.g., here with non-overlapping $2^{10}$ samples long time frames) may be used, which may be defined as:

$$M = \frac{\||S_d| - |S_c|\|_1}{\|S_c\|_1}$$

where, $S_c$ is the Short Time Fourier Transform (STFT) of the clean speech and $S_d$ is the STFT of its de-noised version. Using the above, $M_L$ and $M_H$ may be defined as metrics to measure the STFT similarity between the low and high Q factor components of the clean and noisy speech samples respectively as follows:

$$M_L = \frac{\||S_{Y_L}| - |S_{X_L}|\|_1}{\|S_{X_L}\|_1}, \quad M_H = \frac{\||S_{Y_H}| - |S_{X_H}|\|_1}{\|S_{X_H}\|_1}$$

where the STFT matrix is denoted with S and its corresponding component with its subscript. To maximize the similarity of $S_{X_L}$ and $S_{Y_L}$ as well as the similarity of $S_{X_H}$ and $S_{Y_H}$ simultaneously while taking the relative energy of each component into account, the weighted normalized Manhattan distance may be defined as follows:

$$M_{LH} = \alpha M_L + \beta M_H \text{ where } \alpha + \beta = 1$$

The weighting factors of the $\alpha$ and $\beta$ are selected based on the $L_2$-norms of their corresponding components as follows:

$$\alpha = \frac{\|Y_L\|_2}{\|Y_L\|_2 + \|Y_H\|_2} \quad \beta = \frac{\|Y_H\|_2}{\|Y_H\|_2 + \|Y_H\|_2}$$

Therefore:

$$M_{LH} = \frac{\|Y_L\|_2}{\|Y_L\|_2 + \|Y_H\|_2} \frac{\||S_{Y_L}| - |S_{X_L}|\|_1}{\|S_{X_L}\|_1} + \frac{\|Y_H\|_2}{\|Y_H\|_2 + \|Y_H\|_2} \frac{\||S_{Y_H}| - |S_{X_H}|\|_1}{\|S_{X_H}\|_1}$$

The values of $\lambda_1$ and $\lambda_2$ which minimize $M_{LH}$ can be used to optimize the de-noising stage or:

$$\operatorname{argmin}_{\lambda_1, \lambda_2} \frac{\|Y_L\|_2}{\|Y_L\|_2 + \|Y_H\|_2} \frac{\||S_{Y_L}| - |S_{X_L}|\|_1}{\|S_{X_L}\|_1} + \frac{\|Y_H\|_2}{\|Y_H\|_2 + \|Y_H\|_2} \frac{\||S_{Y_H}| - |S_{X_H}|\|_1}{\|S_{X_H}\|_1}$$

To numerically solve the above, the average $M_{LH}$ may be calculated over many speech samples (n=1000) corrupted with randomly generated multi-talker babble noise with various signal to noise ratios. For each noisy sample, all combinations of $\lambda_1$ and $\lambda_2$ from 0.01 to 0.1 with 0.01 intervals may be used (Total 100 possible combinations) and $M_{LH}$ may be obtained. Two sets of values for $\lambda_1$ and $\lambda_2$ may be selected where each set maximizes the average $M_{LH}$ for noisy signals belonging to one of the classes discussed in the previous stage.

Using the optimized parameters discussed in the previous section, de-noised LQF and HQF components may be obtained. Nevertheless, the spectrograms of these components exhibit some remaining noise still existing in optimally de-noised components $Y_L$ and $Y_H$. Low magnitude 'gaps' in the spectrogram of clean speech components $X_L$ and $X_H$ may be completely filled with noise in their de-noised versions (i.e., $Y_L$ and $Y_H$). Here, by 'gaps' it refers to low magnitude pockets surrounded by high magnitude areas. These low magnitude gaps are more distinctly visible in lower frequencies (i.e., frequencies between 0 and 2000 Hz) where most of the speech signals energy exists. By implementing a more aggressive de-nosing (i.e., choosing larger values for $\lambda_1$ or $\lambda_2$ or both) more noise will be removed and some of these gaps will appear again in de-noised components. Nevertheless, this is only achieved at the expense of inflicting more distortion to the de-noised signal (i.e., larger $M_{LH}$ values). Hence even though more aggressively de-noised LQF and HQF components may have more similar "gap patterns" with the original clean speech components $X_L$ and $X_H$, they are not directly usable due to the high degree of distortion. However, they potentially contain usable information about the location of the gaps in spectrograms of $X_L$ and $X_H$ which may help us de-noise $Y_L$ and $Y_H$ one step further. In order to quantify and measure the similarity between the location of gaps in two spectrograms, the "Gap Binary Pattern" (GBP) matrix may be defined. To create GBP of a signal, the spectrogram of the signal is divided into non-overlapping time/frequency tiles and each tile is categorized as either low magnitude or high magnitude tile. Hence GBP of a spectrogram is a $N_{fb} \times N_{tf}$ binary matrix where $N_{fb}$ is the number of frequency bins and $N_{tf}$ is the number of time frames. Assuming $S_x$ is the STFT matrix of the signal X, and $T_{i,j}$ is a time/frequency tile of $S_X$ which covers the area on the spectrogram which contains all the frequencies between $(i-1)\Delta f$ to $i\Delta f$ on the frequency axis and $(i-1)\Delta t$ to $i\Delta t$ on the time axis, the GBP of X is defined as:

$$G_X(i, j) = \begin{cases} 1, & \text{mean } |T_{i,j}| < \alpha \text{ mean } |S_X| \\ 0, & \text{mean } |T_{i,j}| \geq \alpha \text{ mean } |S_X| \end{cases}$$

In one particularly embodiment, the following may be selected: $f_s=16000$ Hz $\Delta t f_s=2^{10}$, $N_{fb}=128$, $\alpha=0.5$, $\Delta f=62.5$ Hz.

By estimating the location of the gaps in clean speech components, step 168 can potentially remove significant residual noise from $Y_L$ and $Y_H$. If a low amplitude tile in the clean speech components $X_L$ and $X_H$, is categorized as high amplitude in de-noised components $Y_L$ and $Y_H$, then step 168 can conclude that this extra boost in the tile's energy is likely to be originated from the noise and can be attenuated by a reduced gain. Because in reality to clean speech components of $X_L$ and $X_H$ are not readily available, the goal is to find aggressively de-noised low and high Q-factor components (denoted by $Y'_L$ and $Y'_N$) with a similar gap location (in lower frequencies) with the clean speech components of $X_L$ and $X_H$.

To find these aggressively de-noised components, we should find parameter settings that maximize the similarity between GBPs of de-noised and clean speech components in lower frequencies. The best metric to measure the similarity of two GBPs is the Sorenson's metric which is designed to measure the similarity between binary matrices with emphasize on ones (i.e., gaps) rather than zeros. Sorenson's metric for two binary matrices $M_1$ and $M_2$ is defined as:

$$SM(M_1, M_2) = \frac{2C}{N_1 + N_2}$$

where C is the number of 1-1 matches (both values are 1), $N_1$ is the total number of 1s in the matrix $M_1$ and $N_2$ is the total number of 1s in the matrix $M_z$.

In this stage, two new sets of regularization parameters may be identified; one should maximize SM ($G_{X_L}$, $G_{Y_L}'$) and the other should maximize SM ($G_{X_H}$, $G_{Y_H}'$).

Two sets of regularization parameters may be numerically found which maximize the Sorenson's metrics by measuring SM ($G_{X_L}$, $G_{Y_L}'$) and SM ($G_{X_H}$, $G_{Y_H}'$) for sufficiently large number of speech samples (n=1000) corrupted with randomly generated multi-talker babble noise with various signal to noise ratios. There may be three sets of regularization parameters as follows: $\lambda_1$ and $\lambda_2$ found by minimizing $M_{LH}$ and are used to generate optimally de-noised components of $Y_L$ and $Y_H$. $\lambda_1'$ and $\lambda_2'$ found by maximizing SM ($G_{X_L}$, $G_{Y_L}'$) and are used to generate the aggressively de-noised component $Y'_L$ with similar gaps location with $X_L$. $\lambda_1''$ and $\lambda_2''$ by found by maximizing SM($G_{X_H}$, $G_{Y_H}'$) and are used to find the aggressively de-noised component $Y'_H$ with similar gaps location with $X_H$.

Because $Y_L'$ and $Y_H'$ have optimally similar gap patterns to $X_L$ than $Y_L$ respectively, they can be used as a template further clean up optimally de-noised $Y_L$ and $Y_H$. To achieve this, spectral cleaning may be performed on $Y_L$ and $Y_H$, based on the GBPs of the aggressively de-noised $Y_L'$, $Y_H'$. Using the time/frequency tiling, reduction gains $r_L$ and $r_H$ may be applied to high magnitude tiles $T_{i,j}$ in $Y_L$ and $Y_H$ with low magnitude counter parts $T_{i,j}'$ in $Y_L'$ and $Y_H'$. In some embodiments, the spectral cleaning is only performed in lower frequencies (i.e., frequencies between 0 and 2000 Hz).

$$\hat{T}_{i,j} = \begin{cases} r_L(i, j)T_{i,j}, & G_{Y_L'}(i, j) = 1 \text{ and } G_{Y_L}(i, j) = 0 \\ T_{i,j}, & \text{Otherwise} \end{cases}$$

$$r_L(i, j) = \frac{\text{mean } |S_{Y_L}| \text{ mean } |T_{i,j}'|}{\text{mean } |T_{i,j}| \text{ mean } |S_{Y_L'}|}$$

where $T_{i,j}$ and $T_{i,j}'$ are time/frequency tiles in $S_{Y_L}$ and $S_{Y_L'}$ respectively and the resulting enhanced STFT matrix and its time/frequency tiles are denoted with $\hat{S}_{X_L}$ and $\hat{T}_{i,j}$.

$$\hat{T}_{i,j} = \begin{cases} r_H(i, j)T_{i,j}, & G_{Y_H'}(i, j) = 1 \text{ and } G_{Y_H}(i, j) = 0 \\ T_{i,j}, & \text{Otherwise} \end{cases}$$

$$r_H(i, j) = \frac{\text{mean } |S_{Y_H}| \text{ mean } |T_{i,j}'|}{\text{mean } |T_{i,j}| \text{ mean } |S_{Y_H'}|}$$

where $T_{i,j}$ and $T_{i,j}'$ are time/frequency tiles in $S_{Y_H}$ and $S_{Y_H'}$ respectively and the resulting enhanced STFT matrix and its time/frequency tiles are denoted with $\hat{S}_{X_H}$ and $\hat{T}_{i,j}$.

Note that the reduction gains are chosen to decrease the normalized average magnitude of the tiles in $S_{Y_L}$, $S_{Y_H}$ to the level of the normalized average magnitude of the tiles in $S_{Y_L}'$, $S_{Y_H}'$. The gaps which were filled by noise in optimally de-noised components may be visible after spectral cleaning.

In step 170, after spectral cleaning the enhanced low and high Q-factor components of $\hat{X}_L$ and $\hat{X}_H$ can be obtained by inverse short time Fourier transform of $\hat{S}_{X_L}$ and $\hat{S}_{X_H}$ and eventually $\hat{X}$ which is the de-noised version of clean speech X can be created by re-composition of $\hat{X}_L$ and $\hat{X}_H$ as:

$$\hat{X} = \hat{X}_L + \hat{X}_H$$

In summary, a first embodiment of the present invention may a system and method for improving intelligibility of speech. The system and method may include obtaining an input audio signal, decomposing the audio signal into a first component having a low or no sustained oscillatory pattern, and a second component having a high oscillatory pattern, further de-noising the second component based on data generated from the first component to obtained a modified second component, and outputting an audio signal having reduced noise, the output audio signal comprising the first component in combination with the modified second component.

In particular, a first embodiment of the present invention may provide systems and methods for reducing noise and/or improving intelligibility of an audio signal that utilizes Q-factor based signal decomposition. For example, an exemplary method for reducing noise may be provided. The method comprises a first step for receiving an input audio signal comprising a speech signal and a noise. In some embodiments, the noise may comprise a multi-talker babble noise. The method also comprises a step for decomposing the input audio signal into at least two components, the at least two components comprises a first component having a low or no sustained oscillatory pattern, and a second component having a high oscillatory pattern. In certain embodiments, the decomposing step comprises de-noising the first and second components, and the first component is more aggressively de-noised than the second component. In some embodiments, the decomposing step may include determining a first Tunable Q-Factor Wavelet Transform (TQWT) for the first component and a second TQWT for the second component. The method also comprises a step for de-noising the second component based on data generated from the first component to obtained a modified second component. In some embodiments, the de-noising step comprises further modifying the second component to obtain a modified second component having a temporal and spectral pattern (TSP) corresponding to a TSP of the first component. The method further comprises a step for outputting an audio signal having reduced noise, the output audio signal comprising the first component in combination with the modified second component. The outputted audio signal may more closely correspond to the speech signal than the input audio signal.

In another aspect, a method for improving intelligibility of speech is provided. The method comprises a first step for obtaining, from a receiving arrangement, an input audio signal comprising a speech signal and a noise, and then a step for estimating a noise level of the input audio signal. In some embodiments, the estimating step comprises determining or estimating a signal to noise (SNR) for the input audio signal. The method also includes a step for decomposing the input audio signal into at least two components when the estimated noise level of the input audio signal is above a predetermined threshold, the at least two components comprises a first component having a low or no sustained oscillatory pattern, and a second component having a high oscillatory pattern. The method also includes a step for de-noising the second component based on data generated from the first component to obtained a modified second component. The method further includes a step for outputting an audio signal having reduced noise to an output arrangement, the output audio signal comprising the first component in combination with the modified second component.

In another aspect, a non-transitory computer readable medium storing a computer program that is executable by at least one processing unit. The computer program comprise sets of instructions for: receiving an input audio signal comprising a speech signal and a noise; decomposing the input audio signal into at least two components, the at least two components comprises a first component having a low or no sustained oscillatory pattern, and a second component having a high oscillatory pattern; de-noising the second component based on data generated from the first component to obtained a modified second component; and outputting an audio signal having reduced noise, the output audio signal comprising the first component in combination with the modified second component.

In a further aspect, a system for improving intelligibility for a user is provided. The system may comprise a receiving arrangement configured to receive an input audio signal comprising a speech signal and a noise. The system may also include a processing arrangement configured to receive the input audio signal from the cochlear implant, decompose the input audio signal into at least two components, the at least two components comprises a first component having a low or no sustained oscillatory pattern, and a second component having a high oscillatory pattern, de-noise the second component based on data generated from the first component to obtained a modified second component, and output an audio signal having reduced noise to the cochlear implant, the output audio signal comprising the first component in combination with the modified second component. The system may further comprise a cochlear implant, wherein the cochlear implant includes the receiving arrangement, and the cochlear implant is configured to generate an electrical stimulation to the user, the electrical stimulation corresponds to the output audio signal. Alternatively, the system may further comprise a mobile computing device, wherein the mobile computing device includes the receiving arrangement, and the mobile computing device is configured to generate an audible sound corresponding to the output audio signal.

Noise Reduction with Reduced Latency (e.g., SEDA-RT Method)

In a second embodiment, systems and methods for reducing noise and/or improving intelligibility of an audio signal that provides reduced latency, so as to provide de-noising in real-time or near real-time. For example, an exemplary method for noise reduction, in particular, multi-talker babble noise reduction in a cochlear implant, the method may be used to improve recognition and intelligibility of speech to patients in need of hearing assistance, while providing reduced latency in the exemplary de-noising processes. In particular, the systems and methods may utilize a novel classifier, a method for parallel de-noising, a new method for de-noising using adaptive thresholding, and/or a new method for de-noising by decomposing the signal into a plurality of sub-bands. In an exemplary method, a rough determination of the noise level in the input signal may be determined before starting a de-noising process. In addition, the estimated level of noise present may be utilized to set a wavelet and optimizations parameters for subsequent de-noising of the input signal.

Figure 3A:
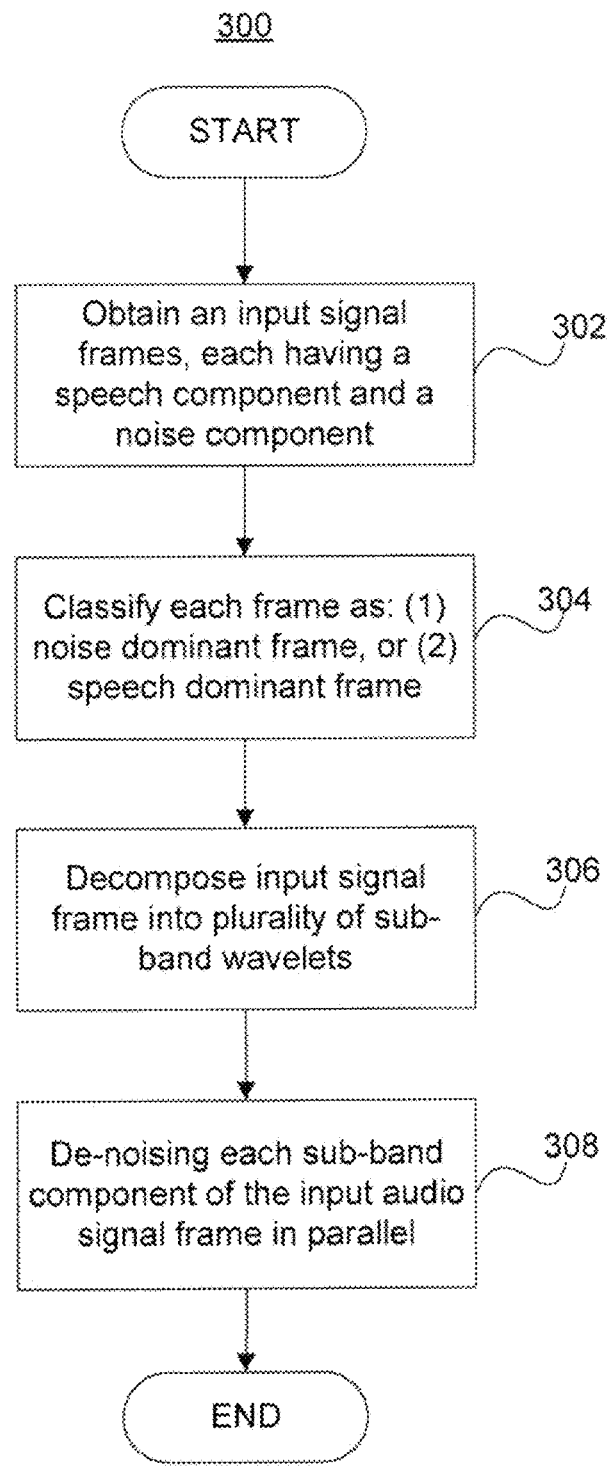
FIG. 3a shows another exemplary method for noise reduction, in particular, multi-talker babble noise reduction in a cochlear implant.

FIG. 3a illustrates a second exemplary method 300 for noise reduction, in particular, multi-talker babble noise reduction in a cochlear implant. Specifically, the method may be used to improve recognition and intelligibility of speech to patients in need of hearing assistance. Any suitable cochlear implant may be used with exemplary method 300. In particular, the cochlear implant may detect an audio signal and restore a deaf or partially deaf individual's ability to hear by providing an electrical stimulation to the auditory nerve corresponding to the audio signal. However, often the input audio signal may be noisy and cannot be recognized or discerned by the user. Therefore, the input signal may be further processed, e.g., filtered, to improve clarity and/or intelligibility of speech to the patient.

In a first step 302, an input audio signal or a frame of an input audio signal may be obtained. The input audio signal may comprise a speech signal and noise. In certain embodiments, the noise comprises a multi-talker babble noise. In some embodiments, step 302 may obtain a successive frames of input audio signals that are non-overlapping. In other embodiments, step 302 may obtain successive frames of input audio signals that are overlapping. The input audio signal may be a continuous audio signal and may be broken down into predetermined segments and/or frames for processing by the exemplary method 300. In particular, in a real-time application, such as an application for improving hearing for a CI user or for improving intelligibility of audio communications on a communications device (such as mobile communications device, a telephone, a smart phone, etc.), the input signal may include non-steady noise where the level of noise, e.g., signal to noise ratio, may change over time. To adapt to the changing levels of noise intensity in an input signal, the signal may be separated into a plurality of frames of input signal, where each frame may be individually analyzed and/or de-noised, such as for example, processing each individual frame using the exemplary method 300. The input signal may be divided into the plurality of frames by any suitable means. The exemplary method may be continuously applied to each successive frame of the input signal for analysis and/or de-noising. In some embodiments of the exemplary method 300, the input audio signal may be obtained and each frame of the input audio signal may be processing by the exemplary method in real-time or substantially real-time, meaning within a time frame that is negligible or imperceptible to a user, for example, within less than 100 milliseconds, less than 90 milliseconds, less than 70 milliseconds, or less than 40 milliseconds.

Figure 3B:
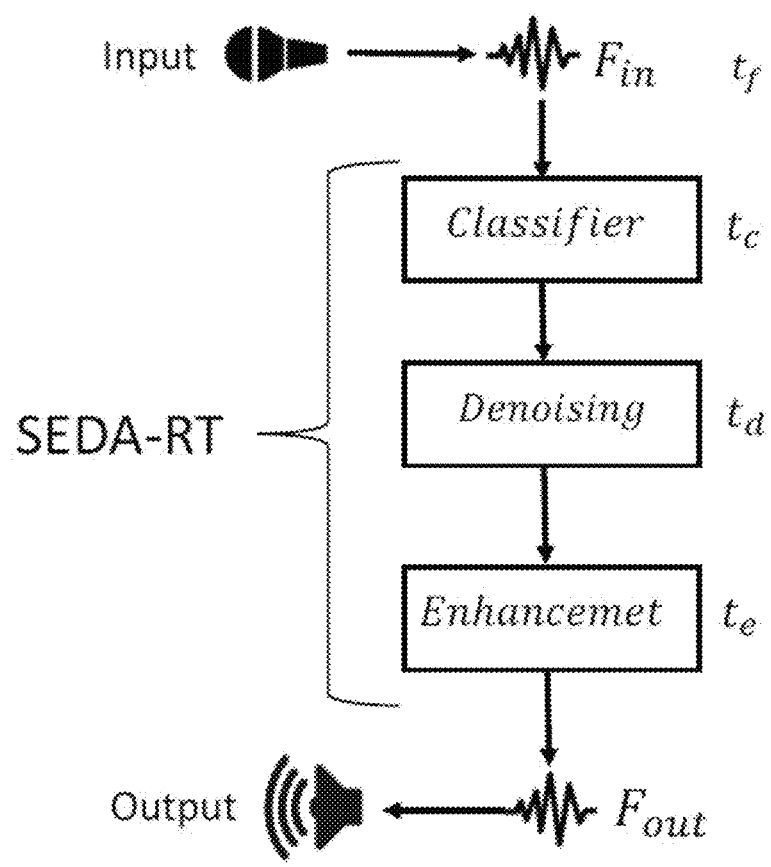
FIG. 3b shows an exemplary embodiment for a method for real-time babble noise reduction, also referred to herein as Speech Enhancement using Decomposition Approach—Real Time (SEDA-RT).

The exemplary method 300 provides a babble noise reduction method (e.g., a SEDA-RT (Speech Enhancement using Decomposition Approach—Real Time version)) that solves the ineffectiveness of simple temporal/spectral thresholding, as discussed above and shown in FIG. 1. The exemplary method also provides a babble noise reduction that operates in real-time or substantially real-time with a very short latency. In SEDA-RT, non-overlapping frames (for step 302) are preferably used for two main reasons: First; to avoid slowing down the method or process by the extra computation due to overlapping frames (using 50% overlapping will reduce the algorithm speed to half). Second; overlapping frames allow longer frames without increasing latency but when the noise is non-stationary (e.g., babble) long frames will lead to poor temporal resolution which will degrade the method's performance. However, if the device's or processing arrangement's processing power is high enough to perform in real-time or substantially in real-time when using overlapping frames and the number of talkers in babble is large (slower variation in babble properties), then SEDAT-RT can use overlapping frames to decrease the latency and potentially increase the de-noising performance. Being real time means that the processing time required to de-noise an incoming frame of the noisy speech should be shorter than the duration of the frame itself. Given the frames don't overlap, short latency means the length of each incoming frame to be as short as possible. FIG. 3b shows the general block diagram for SEDA-RT. Every incoming frame of the noisy signal will go through the following three steps:

Classification
De-noising
Enhancement

Assuming that $t_c$, $t_d$ and $t_e$ are the times required for processing an incoming block $F_{in}$ by above mentioned steps respectively. In order to maintain the real time operation of SEDA-RT, the total required processing time for all three steps must be less than the duration of the $F_{in}$ or:

$$t_c + t_d + t_e \leq t_f \quad (4)$$

Where: $t_f$ is the duration of $F_{in}$. The main challenge to keep a de-nosing algorithm real-time is to avoid any iterative or computationally costly process.

Having a low latency is also an important aspect of a good real-time de-noising algorithm. Latency is the delay between the time a frame enters the de-noising algorithm and the time it exits. If the algorithm is real time and incoming frames don't overlap, then the latency is equal to the duration of the frames. Because the discrepancy between audio cues and visual cues starts to be noticed at latencies around 100 ms, it is preferable to keep the latency of SEDA-RT below this limit. Hence, $t_f$ is preferably less than 100 ms. That means that the classifier and de-noising algorithm should be able to perform well on very short frames of signal. Most of the conventional classification features and de-noising algorithms need sufficiently long frames of signal to perform well. The main challenge to keep the latency short is to find a set of very robust features and an efficient de-noising algorithm which can perform well even if the incoming signal's frames are very short.

In Examples III and IV below, the three stages of SEDA-RT are described in detail. In addition, methods for clinical testing the algorithm, and collected data from CI users using SEDA-RT are also provided. In addition, the speed and latency of the exemplary method 300 are measured using different computing machines (e.g., cell phones, tablets, and computers).

In step 304, each frame of an input signal may be classified to a first category or a second category. The first category may correspond to the noise being stronger than the speech signal, and the second category may correspond to the speech signal being stronger than the noise. As discussed herein, the term "stronger" may refer to having more of one component over another, e.g., the first category may correspond to an input signal being comprised more of noise as compared to speech signal. Similarly, the second category may correspond to an input signal being comprised more of speech signal than noise. In particular, the exemplary method 300 may utilize a classifier which is capable of classifying the relatively short frames of the noisy signal into one of the two following categories:

1. Noise dominated frames: frames in which the noise is significantly stronger than speech
2. Speech dominated frames: frames in which the speech is significantly stronger than noise The classifier may be computationally efficient and accurate, even when applied to short frames (less than 100 ms in duration) corrupted by speech-like non-stationary noise (e.g., Multi-talker babble). It may also work well on short frames for the purpose of achieving a low-latency implementation.

In certain embodiments, the classifying step may comprise applying a principle component analysis using a plurality of features, wherein the plurality of features includes at least one of: (1) an envelope variance feature of the input audio signal frame; (2) an envelope mean crossing feature of the input audio signal frame; (3) a root mean square feature of the input audio signal frame as compared to a predetermined threshold value; and (4) an entropy feature of a histogram of the input audio signal frame. The input audio signal frame may be classified into the first category when the principle component analysis identifies predominantly noise from the input audio signal frame, and into the second category when the principle component analysis identifies predominantly speech signal from the input audio signal frame. In one exemplary embodiment, each of the plurality of features may each be weighted differently in the principle component analysis. In another exemplary embodiment, the predetermined threshold value for the root mean square feature is based on a previous audio signal frame received by the receiving arrangement. In particular, the previous audio signal frame may include predominantly noise. The principle component analysis and each of the plurality of features are described further below in Examples III and IV. In a further embodiment, step 304 may further comprise a step for adjusting the plurality of features based on the input audio signal by an iterative method using a Gaussian mixture model for a plurality of sub-categories, wherein the first and second categories are each further divided into the plurality of sub-categories.

In step 306, each frame of the input audio signal may be decomposed into a plurality of wavelet sub-bands. Each sub-band may have a different sampling rate and number of coefficients. Each sub-band may encompass a different range of the audio spectrum. Each of the sub-bands may be divided into a plurality of coefficient-groups. In one particular embodiment, each sub-band may correspond to a TQWT wavelet sub-band. For each frame of the input audio signal, all sub-bands and their coefficients form a representation of the frame in a TQWT wavelet domain.

More particularly, in the exemplary method 300 (e.g., SEDA-RT), each sub-band may be divided into smaller "coefficient-groups" (each coefficient-group may contain, for example, 16 coefficients). Each of the coefficient groups may be initially de-noising using an adaptive group thresholding method. For example, an exemplary adaptive group thresholding method may be applied to all members to all members of each coefficient-group. The threshold type (e.g., soft or hard) and aggressiveness (e.g., threshold level) of the adaptive group thresholding applied on a coefficient group may depend on first, category of the noisy frame (e.g., speech dominated or noise dominated) and second, the energy level (e.g., II norm) of the coefficient group. Further details of the adaptive group thresholding methods are provided below in Examples III and IV.

In step 308, each sub-band component of the input audio signal frame may be de-noised by various suitable means. In particular, each sub-band component of an input audio signal frame may be de-noised in parallel. Step 308 may utilize any suitable wavelet transform method for de-noising. More particularly, in the exemplary method 300, multiple wavelet transforms with different settings may be used in parallel. Hence multiple de-noised versions of the same signal may be obtained. The resulting multiple de-noised signals may be averaged to obtained significantly reduced de-noising distortion. For example, step 308 may apply a first wavelet de-noising method including a first wavelet transform and a predetermined threshold for the sub-band component, and a second wavelet de-noising method including a second wavelet transform and the predetermined threshold for the sub-band component. The predetermined threshold for each sub-band component may be based on at least one previous noise-dominant signal frame received by the receiving arrangement. In addition, the first and second wavelets may be configured to more aggressively de-noise the input audio signal frame when the input audio signal frame is classified in the first category as compared to when the input audio signal frame is classified in the second category. In one embodiment, the first and second wavelet transforms are Tunable Q-Factor Wavelet Transforms (TQWTs). The first and second wavelet transforms may be selected based whether the input audio signal is classified into the first category or the second category. Exemplary embodiments of step 308 are further described in Examples III and IV below.

Furthermore, the resulting de-noised signal may be further enhanced, as described below in Examples III and IV. For example, the exemplary method 300 may further comprise an enhancement step, which comprises filtering the signal through a low pass filter. In the exemplary method 300 (e.g., SEDA-RT), the de-noising process may produce undesired high frequency artifacts which may be reduced or eliminated by a low pass filter.

Those skilled in the art will understand that the exemplary embodiments (e.g., SEDA and SEDA-RT methods) described herein may be implemented in any number of manners, including as a separate software module, as a combination of hardware and software, etc. For example, the exemplary analysis methods may be embodiment in one or more programs stored in a non-transitory storage medium and containing lines of code that, when compiled, may be executed by at least one of the plurality of processor cores or a separate processor. In some embodiments, a system comprising a plurality of processor cores and a set of instructions executing on the plurality of processor cores may be provided. The set of instructions may be operable to perform the exemplary methods discussed herein. The at least one of the plurality of processor cores or a separate processor may be incorporated in or may communicate with any suitable electronic device for receiving audio input signal and/or outputting a modified audio signal, including, for example, an audio processing device, a cochlear implant, a mobile computing device, a smart phone, a computing tablet, a computing device, etc.

Figure 4:
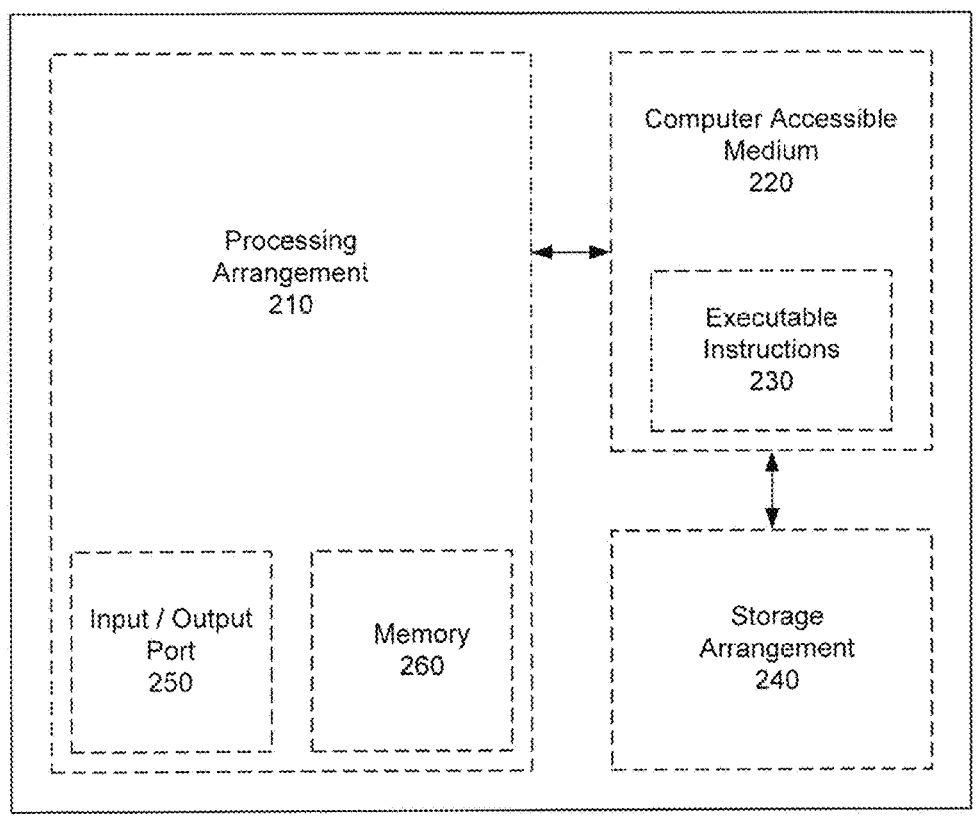
FIG. 4 shows an exemplary computer system for performing method for noise reduction.

Although the exemplary analysis methods describe herein are discussed in reference to a cochlear implant. It is contemplated that the exemplary methods may be incorporated into any suitable electronic device that may require or benefit from improved audio processing, particularly noise reduction. For example, the exemplary methods may be embodied in an exemplary system 200 as shown in FIG. 4. For example, an exemplary method described herein may be performed entirely or in part by a processing arrangement 210. Such processing/computing arrangement 210 may be, e.g., entirely or a part of, or include, but not limited to, a computer/processor that can include, e.g., one or more microprocessors, and use instructions stored on a computer-accessible medium (e.g., RAM, ROM, hard drive, or other storage device). As shown in FIG. 4, e.g., a computer-accessible medium 220 (e.g., as described herein, a storage device such as a hard disk, floppy disk, memory stick, CD-ROM, RAM, ROM, etc., or a collection thereof) can be provided (e.g., in communication with the processing arrangement 210). The computer-accessible medium 220 may be a non-transitory computer-accessible medium. The computer-accessible medium 220 can contain executable instructions 230 thereon. In addition or alternatively, a storage arrangement 240 can be provided separately from the computer-accessible medium 220, which can provide the instructions to the processing arrangement 210 so as to configure the processing arrangement to execute certain exemplary procedures, processes and methods, as described herein, for example.

System 200 may also include a receiving arrangement for receiving an input audio signal, e.g., an audio receiver or a microphone, and an outputting arrangement for outputting a de-noised audio signal, e.g., a speaker, a telephone, or a smart phone. Alternatively, the input audio signal may be a pre-recorded that is subsequently transmitted to the system 200 for processing. For example, an audio signal may be pre-recorded, e.g., a recording having a noisy background, particularly a multi-babble talk noisy background, that may be processed by the system 200 post-hoc. The receiving arrangement and outputting arrangement may be part of the same device, e.g., a cochlear implant, headphones, etc., or separate devices. Alternatively, the system may include a display or output device, an input device such as a keyboard, mouse, touch screen or other input device, and may be connected to additional systems via a logical network.

The system may also include a receiving arrangement for receiving an input audio signal, e.g., an audio receiver or a microphone, and an outputting arrangement for outputting a de-noised audio signal, e.g., a speaker, a telephone, or a smart phone. Alternatively, the input audio signal may be a pre-recorded that is subsequently transmitted to the system for processing. For example, an audio signal may be pre-recorded, e.g., a recording having a noisy background, particularly a multi-babble talk noisy background, that may be processed by the system post-hoc. The receiving arrangement and outputting arrangement may be part of the same device, e.g., a cochlear implant, headphones, etc., or separate devices. Alternatively, the system may include a display or output device, an input device such as a key-board, mouse, touch screen or other input device, and may be connected to additional systems via a logical network.

In one particular embodiment, the system 200 may include a smart phone having a receiving arrangement, e.g., a microphone, for detecting speech, such as a conversation from a user. The conversation from the user may be obtained from a noisy environment, particularly where there is multi-talker babble, such as in a crowded area with many others speaking in the background, e.g., in a crowded bar. The input audio signal received by the smart phone may be processed using the exemplary methods described above and a modified signal, e.g., a cleaned, audio signal, where a noise portion may be reduced and/or a speech signal may be enhanced, may be transmitted via the smart phone over a communications network to a recipient. The modified signal may provide for a more intelligible audio such that a smart phone user from a noisy environment may be more easily understood by the recipient, as compared to an unmodified signal. Alternatively, the input audio signal may be received by the smart phone and transmitted to an external processing unit, such as a centralized processing arrangement in a communications network. The centralized processing arrangement may process the input audio signal transmitted by the smart phone using the exemplary methods described above and forward the modified signal to the intended recipient, thereby providing a centralized processing unit for de-noising telephone calls. In some embodiments, the input audio signal may be a pre-recorded audio signal received by the system 200 and the input audio signal may be processed using the exemplary methods described herein. For example, the system 200 may include a computing device, e.g., a mobile communications device, that includes instructions for processing pre-recorded input audio signals before outputting it to a user. In a further embodiment, the input audio signal may be received by the system 200 (e.g., a smart phone or other mobile communications device), in real-time, or substantially in real-time from a communications network (e.g., an input audio call from a third party received by a smart phone) and the input audio signal may be processed using the exemplary methods described above. For example, a user of the system 200, e.g., smart phone, may receive a noisy an input audio signal from another party, e.g., conversation from the other party, where the other party may be in a noisy environment, particularly where there is multi-talker babble, such as in a crowded area with many others speaking in the background, e.g., in a crowded bar. The input audio signal received via the communications network by the smart phone may be processed using the exemplary methods described above and a modified signal, e.g., a cleaned, audio signal, where a noise portion may be reduced and/or a speech signal may be enhanced, may be outputted to the user, for example, as an audible sound, e.g., outputted through a speaker or any other suitable audio output device or component.

Many of the embodiments described herein may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art can appreciate that such network computing environments can typically encompass many types of computer system configurations, including personal computers, hand-held devices, multi-processor systems, microprocessor-based or programmable consumer electronics, network PCs, minicomputers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. For example, the tasks may be performed by an external device such as a cell-phone for de-noising an input signal and then sending a modified signal from the external device to a CI device via any suitable communications network such as, for example, Bluetooth. In a distributed computing environment, program modules may be located in both local and remote memory storage devices.

EXAMPLES

Example I

The exemplary embodiment of FIG. 2a, as described above may be evaluated by measuring a subject's understanding of IEEE standard sentences with and without processing by the exemplary method 100. Sentences may be presented against a background of 6-talker babble using four different signal to noise ratios (0, 3, 6, or 9 dB). In IEEE standard sentences (also known as "1965 Revised List of Phonetically Balanced Sentences, Harvard Sentences) there may be 72 lists of 10 sentences. To test speech intelligibility in noise, two randomly selected sentence sets (20 sentences) may be presented for each of the following 8 conditions:

1-Speech and 6 Talker Babble (SNR=0 dB)—Unprocessed
2-Speech and 6 Talker Babble (SNR=0 dB)—Processed
3-Speech and 6 Talker Babble (SNR=3 dB)—Unprocessed
4-Speech and 6 Talker Babble (SNR=3 dB)—Processed
5-Speech and 6 Talker Babble (SNR=6 dB)—Unprocessed
6-Speech and 6 Talker Babble (SNR=6 dB)—Processed
7-Speech and 6 Talker Babble (SNR=9 dB)—Unprocessed
8-Speech and 6 Talker Babble (SNR=9 dB)—Processed In addition to the above mentioned conditions, another two sentence sets (20 sentences) may be selected for the following two additional conditions:

9-Speech in quiet (10 Sentences)
10-Practice with all SNRs (10 Sentences)

Each intelligibility test in Example I may include 180 sentences in total. Before processing of any audio signals, 18 sets of sentences that may be spoken by a male speaker may be arbitrarily selected from IEEE standard sentences. In Example I, the selected sentence sets include: 11, 16, 22, 41, 42, 43, 44, 45, 46, 47, 48, 49, 50, 51, 52, 65, 71 and 72. Before each test, two sentence sets may be selected at random for each condition and two other sentence sets may be selected for speech in quiet test and practice session. Then a list, including these 180 sentences in a completely random order may be created. Prior to the test, a practice session with ten sentences, presented in all SNRs may be used to familiarize the subject with the test. The practice session with the subject may last for 5 to 10 minutes. After the practice session, the subjects may be tested on the various conditions. Sentences may be presented to CI subjects in free field via a single loudspeaker positioned in front of the listener at 65 dBA. Subjects may be tested using their clinically assigned speech processor. Subjects may then be asked to use their normal, everyday volume/sensitivity settings. Performance may be assessed in terms of percent of the correctly identified words-in-sentences as a function of SNR for each subject. Each sentence may include five keywords and a number of non-keywords. Keywords may be scored 1 and non-keywords may be scored 0.5.

Figure 5:
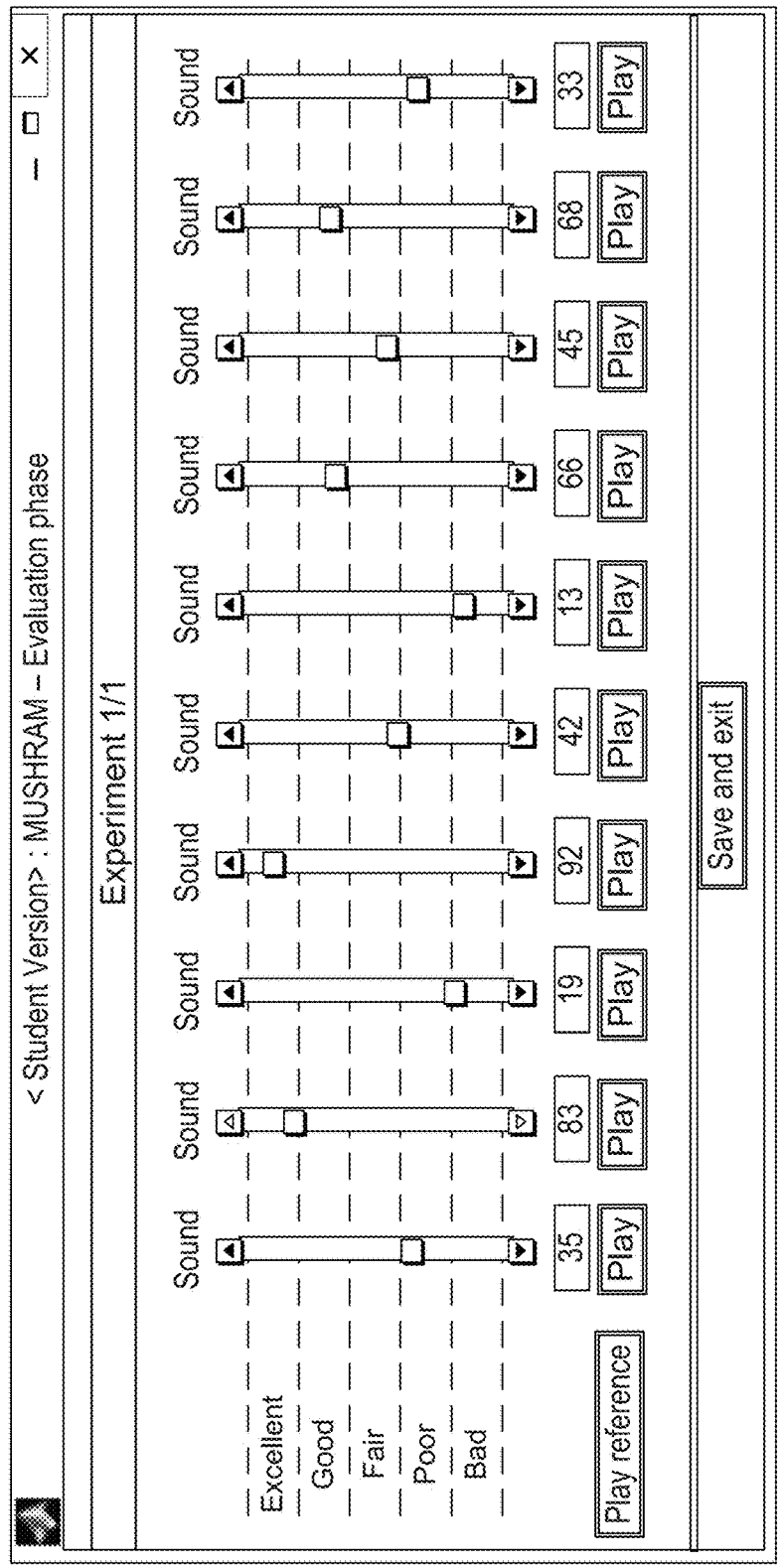
FIG. 5 shows an exemplary embodiment of a user interface for a MUSHRA (MUltiple Stimuli with Hidden Reference and Anchor) evaluation.

After completing a speech understanding test, subjects may be asked to evaluate the sound quality of the sentences using a MUSHRA (MUltiple Stimuli with Hidden Reference and Anchor) scaling test. Participants may complete a total of 5 MUSHRA evaluations, one for each randomly selected sentence. Trials may be randomized among participants. Within each MUSHRA evaluation, participants may be presented with a labeled reference (Clean Speech) and ten versions of the same sentence presented in random order. These versions may include a "hidden reference" (i.e., identical to the labeled reference), eight different conditions (two processing conditions in 4 SNRs) and an anchor (Pure 6-talker babble). Participants may be able to listen to each of these versions without limit by pressing a "Play" button or trigger within a user interface. Participants may then be instructed to listen to each stimulus at least once and provide a sound quality rating for each of the ten sentences using a 100-point scale. To rate a stimulus, participants may move an adjustable slider between 0 and 100, and example of which is shown in FIG. 5. The rating scale may be divided into five equal intervals, and may delineate by the adjectives very poor (0-20), poor (21-40), fair (41-60) good (61-80), and excellent (81-100). Participants may be requested to rate at least one stimulus in the set a score of "100" (i.e., identical sound quality to the labeled reference). Once participants are satisfied with their ratings, they may press a "Save and proceed" button or trigger within a user interface to move to a next trial.

Figure 6A:
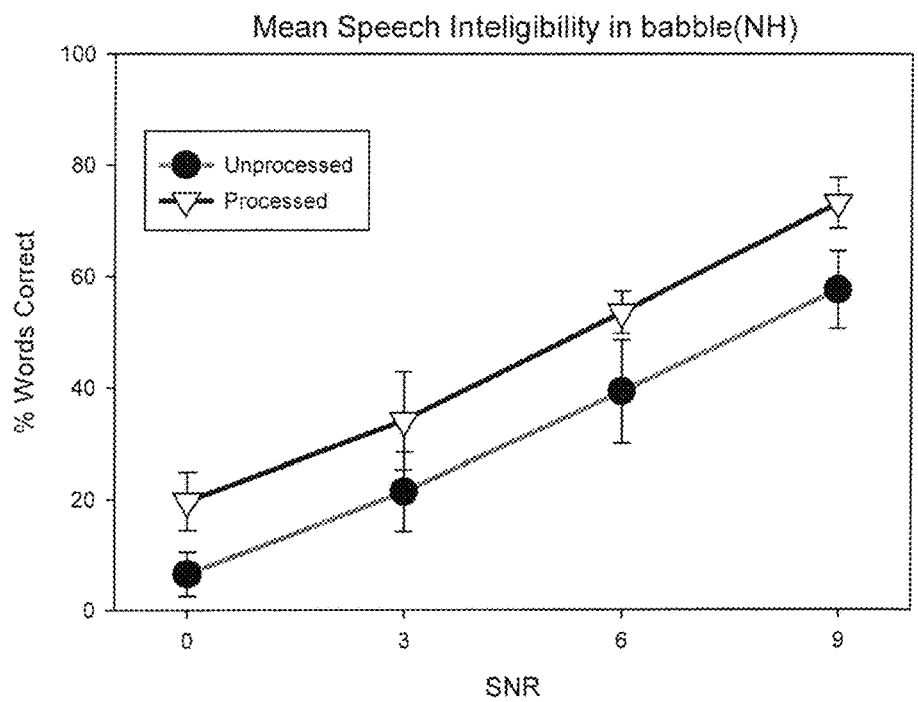
Figure 6B:
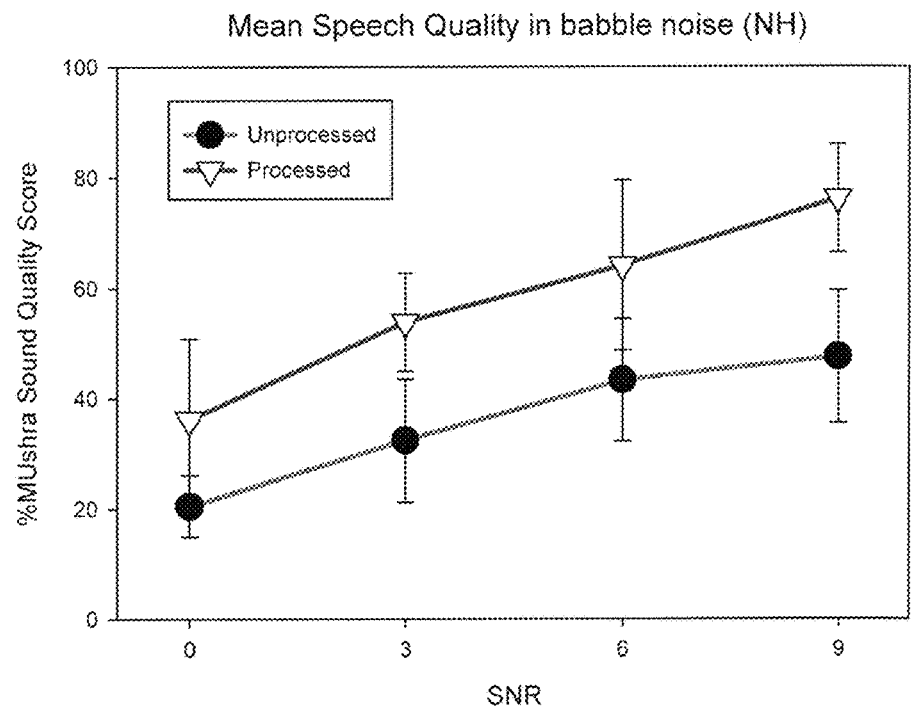

In Example I, as a pilot test, preliminary results were collected with 5 normal hearing (NH) subjects using an eight channel noise-vocoded signals. As shown in FIG. 6a, the percentage of words correct for each unprocessed signal is shown with an open triangle symbol, and the percentage of words correct for each signal processed using the exemplary method 100 of FIG. 2a is shown with a filled-in circle symbol. Similarly, as shown in FIG. 6b, the MUSHRA score for each unprocessed signal is shown with an open triangle symbol, and the MUSHRA score for each signal processed using the exemplary method 100 of FIG. 2a is shown with a filled-in circle symbol. As can be seen in FIGS. 6a and 6b, for all NH subjects, intelligibility and quality improved.

In Example I, for the main test, 7 post-lingually deafened CI subjects, as indicated below in Table 1 were tested. For all subjects intelligibility in quite was measured as a reference and its average was 80.81 percent.

TABLE 1

| Participant | Sex | CI Experience (years) | Type of Implant | Strategy | Clear Voice |
|---|---|---|---|---|---|
| C110 | M | 10 | HR 90KHiFocus 1J | HiRes Optima-S | Medium |
| C105 | F | 10.5 | HiRes 90K 1J | Optima-S | Medium |
| C113 | F | 6 | HiRes 90K/Hifocus 1J | HiRes-S w/Fidelity 120 | Medium |
| C107 | F | 14 | CII-HiFocus 1J | Optima-P | Medium |
| C120 | F | 0.5 | HR 90K/HiFocus MS | Hi Res Optima-S | Medium |
| C106 | M | 5 | HiRes 90K 1J | HiRes-S w/Fidelity 120 | Medium |
| C118 | F | 5.5 | HR 90K HiFocus 1J | HiRes-P w/fidelity 120 | Medium |

*Note:
For MUSHRA test, oral data was collected from subject C118 due to her severe visual impairment.

Figure 7:
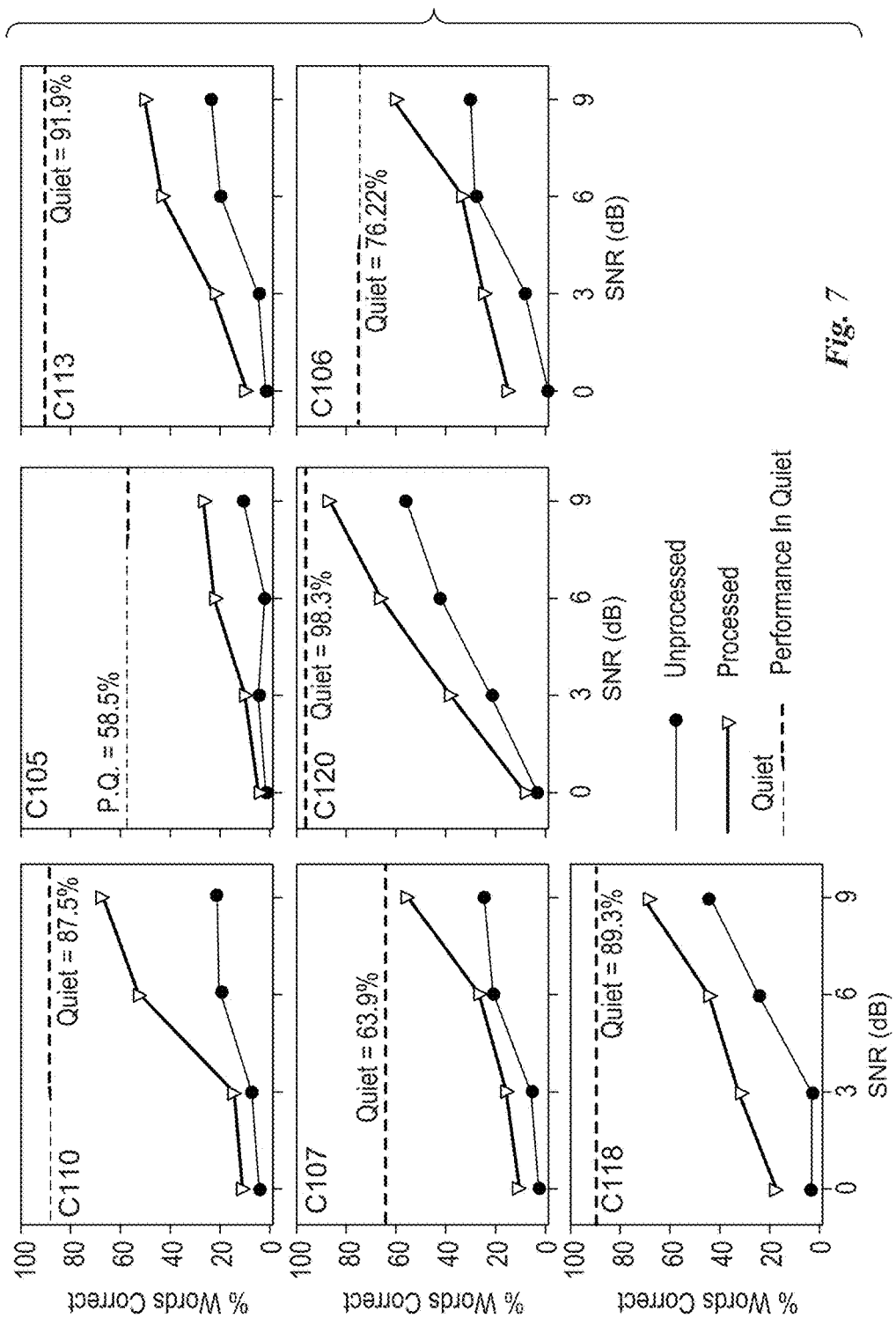
Figure 9A:
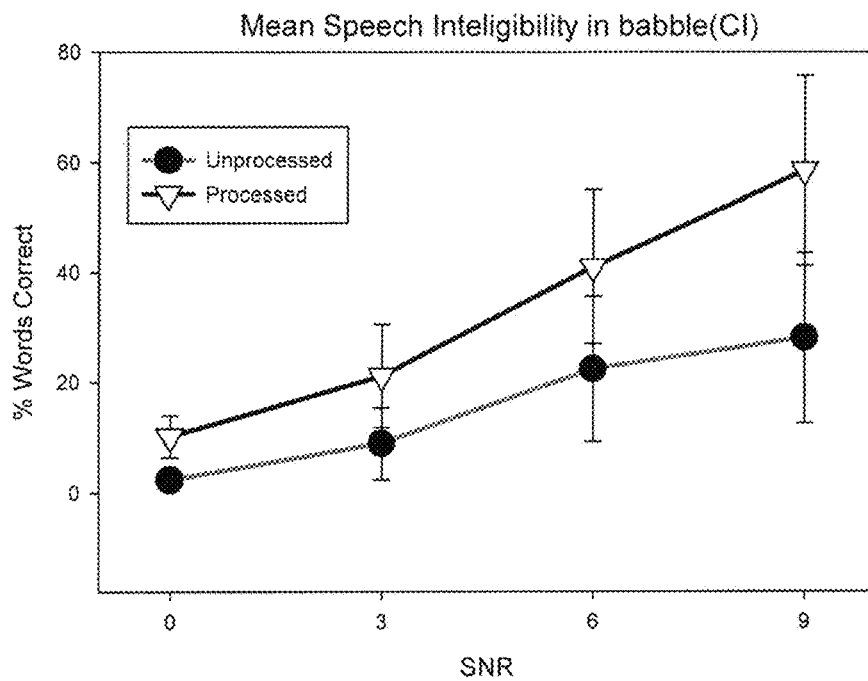
FIG. 9a shows an average of the data corresponding to percentages of words correct in CI patients of FIG. 7.

As shown in FIG. 7, word-in-sentence intelligibility in the presence of 6 talker babble background as a function of the SNR for individual subjects. Data for each unprocessed signal is shown with an open triangle symbol, whereas data for each signal processed using the exemplary method 100 of FIG. 2a is shown with a filled-in circle symbol. FIG. 9a shows an average result for all subjects. Mean intelligibility scores, averaged across all subjects and all SNRs, increased by 17.94 percentage points. Two-way ANOVA tests revealed significant main effects of processing [$F(1,6)=128.953$, $p<0.001$] and noise levels [$F(3,18)=40.128$, $p<0.001$]. It also revealed a relatively large interaction between noise levels and algorithms [$F(3,18)=8.117$, $p=0.001$].

Figure 8:
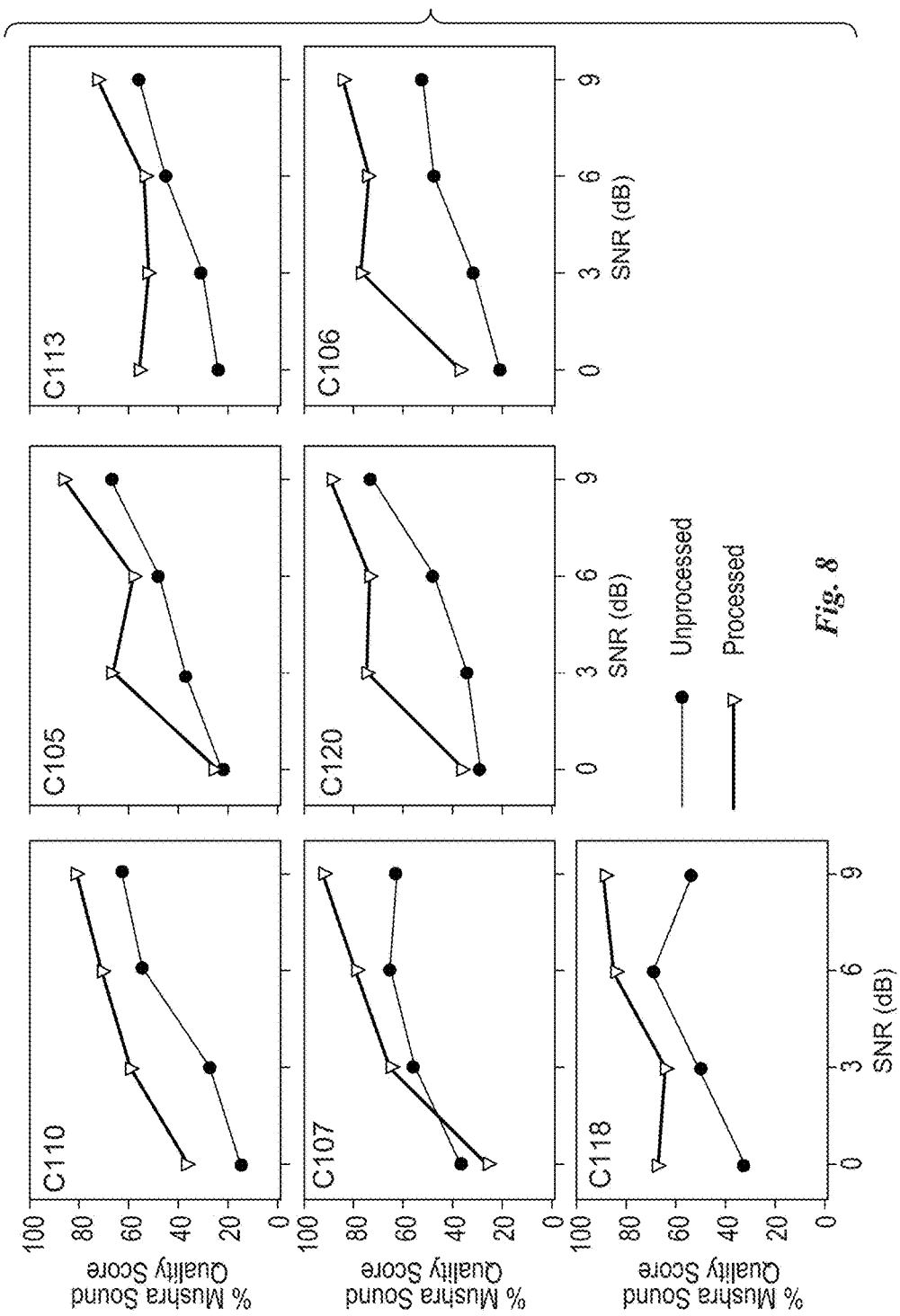
Figure 9B:
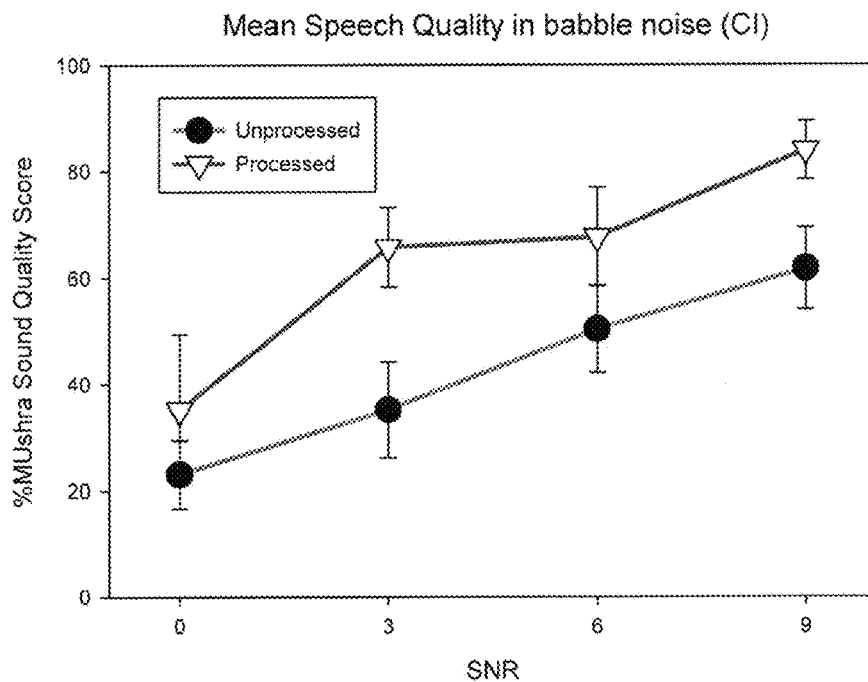
FIG. 9b shows an average of the data corresponding to MUSHRA scores in CI patients of FIG. 8.

FIG. 8 shows speech quality in the presence of 6 talker babble background as a function of the SNR for individual subjects. Data for each unprocessed signal is shown with an open triangle symbol, whereas data for each signal processed using the exemplary method 100 of FIG. 2a is shown with a filled-in circle symbol. FIG. 9b shows average results for all subjects. Mean quality scores, averaged across all subjects and all SNRs, increased by 21.18 percentage points. Two-way ANOVA tests revealed significant main effects of processing [$F(1,6)=72.676$, $p<0.001$] and noise levels [$F(3,18)=42.896$, $p<0.001$]. It also revealed no significant interaction between noise levels and algorithms [$F(3,18)=1.914$, $p=0.163$].

As can be seen above, the exemplary method 100 of FIG. 2a may provide significant speech understanding improvements in the presence of multi-talker babble noise in the CI listeners. The exemplary method 100 performed notably better for higher signal to noise ratios (6 and 9). This could be because of the distortion introduced to the signal due to the more aggressive de-noising strategy for lower SNRs (0 and 3). In Example I, subjects with higher performance in quiet also performed generally better. For the subjects with lower performance in quite (C105 and C107), a floor effect may be seen. However, a ceiling effect was not observed in Example I for the subjects with higher performance in quiet.

Example II

The exemplary embodiment of FIG. 2b, as described above may be evaluated by measuring a subject's understanding of IEEE standard sentences with and without processing by the exemplary method 150. All babble samples in Example II are randomly created by mixing sentences randomly taken from a pool of standard sentences which contains a total of 2,100 sentences (including IEEE standard sentences with male and female speaker, Hint sentences and SPIN sentences). For each babble sample, the number of talkers was randomized between 5 to 10 and the gender ratio of talkers also was randomly selected (all female, all male or a random combination of both.)

Figure 10:
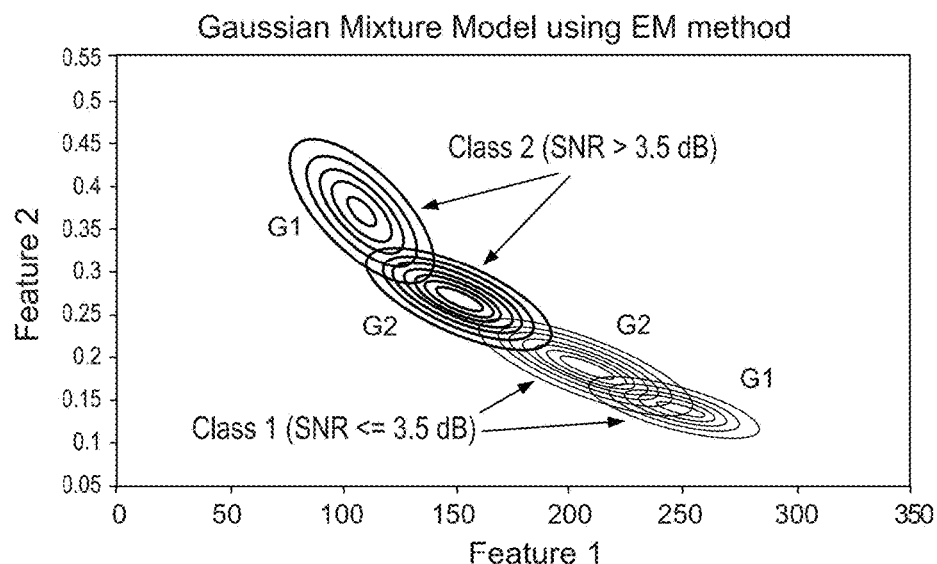
FIG. 10 shows a Gaussian Mixture model of data corresponding to noisy speech samples with SNRs ranging from −10 dB to 20 dB processed using the exemplary method of FIG. 2b.

FIG. 10 shows a Gaussian Mixture model using EM method trained with EM method trained with 100,000 randomly created noisy speech samples with SNRs ranging from −10 dB to 20 dB, as the different speech samples would be classified under step 152. A first set of curves to the right curves represent Gaussian distributions belonging to the class (SNR≤3.5) and a second set of curves to the left represent Gaussian distributions belonging to the class (SNR>3.5).

To evaluate the performance of method 150, a modified version of a two-fold cross validation method may be used. First, half of the sentences in the database were used for training and the second half were used to test the classifier. Then, the sentences used for testing and training (second half of the sentences in the database for training and the first half for testing the classifier) were switched. For a classifier, the F accuracy metric is defined as follows:

$$F = \frac{2\left(\frac{C}{C+f^+}\right)\left(\frac{C}{C+f^-}\right)}{\left(\frac{C}{C+f^+}\right)+\left(\frac{C}{C+f^-}\right)}$$

where C, $f^+$ and $f^-$ are correct, false positive and false negative detection, respectively.

Figure 11:
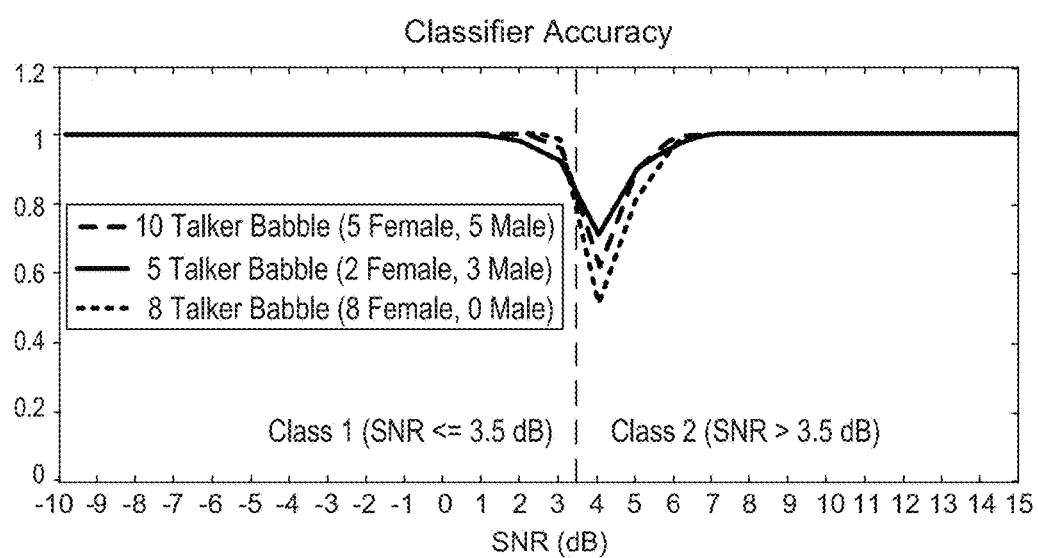
FIG. 11 shows data corresponding to variation of accuracy metric F as a function of SNR for three different multi-talker babble noise according to the exemplary method of FIG. 2b.

The average values of F accuracy metric were measured for three types of multi-talker babble in different SNRs. The average value of F slightly changed by changing the number and the gender ratio of talkers. The average value of F was 1 for SNRs outside the neighborhood of the border SNR between two classes (i.e., 3.5 dB). In the vicinity of SNR=3.5 dB some decline in the accuracy was observed. FIG. 11 shows the variation of accuracy metric F as a function of SNR for three different multi-talker babble noise. 1,000 randomly created noisy samples were tested for each SNR.

Figure 12:
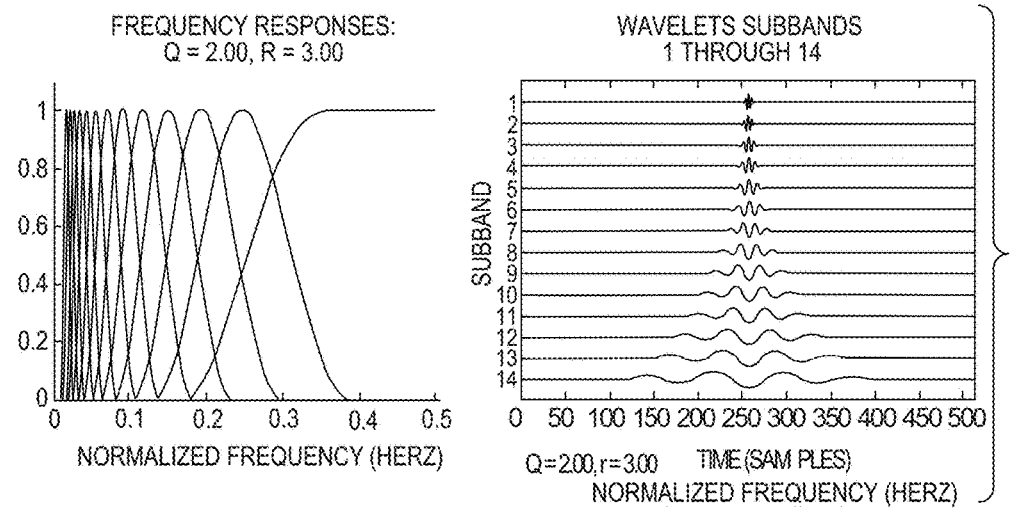
FIG. 12 shows data corresponding to frequency response and sub-band wavelets of a TQWT according to the exemplary method of FIG. 2b.

FIG. 12 shows frequency response and sub-band wavelets of a TQWT, e.g., step 160 as described above. Specifically, FIG. 12 shows frequency response (left) sub-band wavelets (right) of a TQWT with Q=2, r=3, J=13.

Table 2 shows specific selected values for $\lambda_1$ and $\lambda_1$ in Example II as well as other parameters for each class.

TABLE 2

| Settings | $Q_1$ | $Q_2$ | $r_1$ | $r_1$ | $j_1$ | $j_2$ | $\lambda_1$ | $\lambda_2$ |
|---|---|---|---|---|---|---|---|---|
| SNR ≤ 3.5 dB | 1 | 5 | 3 | 3 | 10 | 37 | 0.07 | 0.07 |
| SNR > 3.5 dB | 1 | 5 | 3 | 3 | 10 | 37 | 0.05 | 0.05 |

To validate the optimization results with other distance metrics, the Manhattan distance of the sum of two components in were minimized:

$$M = \frac{\|s_{(Y_L+Y_H)} - s_X\|_1}{\|s_X\|_1}$$

as well as the Euclidean distance of the de-noised and clean components in:

$$M = \frac{\|Y_L\|_2}{\|Y_L\|_2 + \|Y_H\|_2} \frac{\|\|s_{Y_L}\| - |s_{X_L}\|\|_2}{\|s_{X_L}\|_2} + \frac{\|Y_H\|_2}{\|Y_H\|_2 + \|Y_H\|_2} \frac{\|\|s_{Y_H}\| - |s_{X_H}\|\|_2}{\|s_{X_H}\|_2}$$

The same results for $\lambda_1$ and $\lambda_2$ were achieved.

In this example, two sets of regularization parameters were found which maximize the Sorenson's metrics by measuring SM ($G_{X_L}$, $G_{Y_L}$') and SM ($G_{X_H}$, $G_{Y_H}$') for sufficiently large number of speech samples (n=1000) corrupted with randomly generated multi-talker babble noise with various signal to noise ratios. Three sets of regularization parameters were also identified as follows: $\lambda_1$ and $\lambda_2$ found by minimizing $M_{L_H}$ and are used to generate optimally de-noised components of $Y_L$ and $Y_H$. $\lambda_1$' and $\lambda_2$' found by maximizing SM ($G_{X_L}$, $G_{Y_L}$') and are used to generate the aggressively de-noised component $Y'_L$ with similar gaps location with $X_L$. $\lambda_1$" and $\lambda_2$" by found by maximizing SM ($G_{X_H}$, $G_{Y_H}$') and are used to find the aggressively de-noised component $Y'_H$ with similar gaps location with $X_H$. Table 3 shows selected values for these regularization parameters for both classes.

TABLE 3

| Settings | Minimize $M_{LH}$ | Maximize SM ($G_{X_L}$, $G_{Y_L}$) | Maximize SM ($G_{X_H}$, $G_{Y_H}$) |
|---|---|---|---|
| Class SNR ≤ 3.5 dB | $\lambda_1$ = 0.08 $\lambda_2$ = 0.08 | $\lambda'_1$ = 0.05 $\lambda'_2$ = 0.02 | $\lambda"_1$ = 0.04 $\lambda"_2$ = 0.09 |
| Class SNR > 3.5 dB | $\lambda_1$ = 0.04 $\lambda_2$ = 0.04 | $\lambda'_1$ = 0.02 $\lambda'_2$ = 0.01 | $\lambda"_1$ = 0.01 $\lambda"_2$ = 0.02 |

Figure 13:
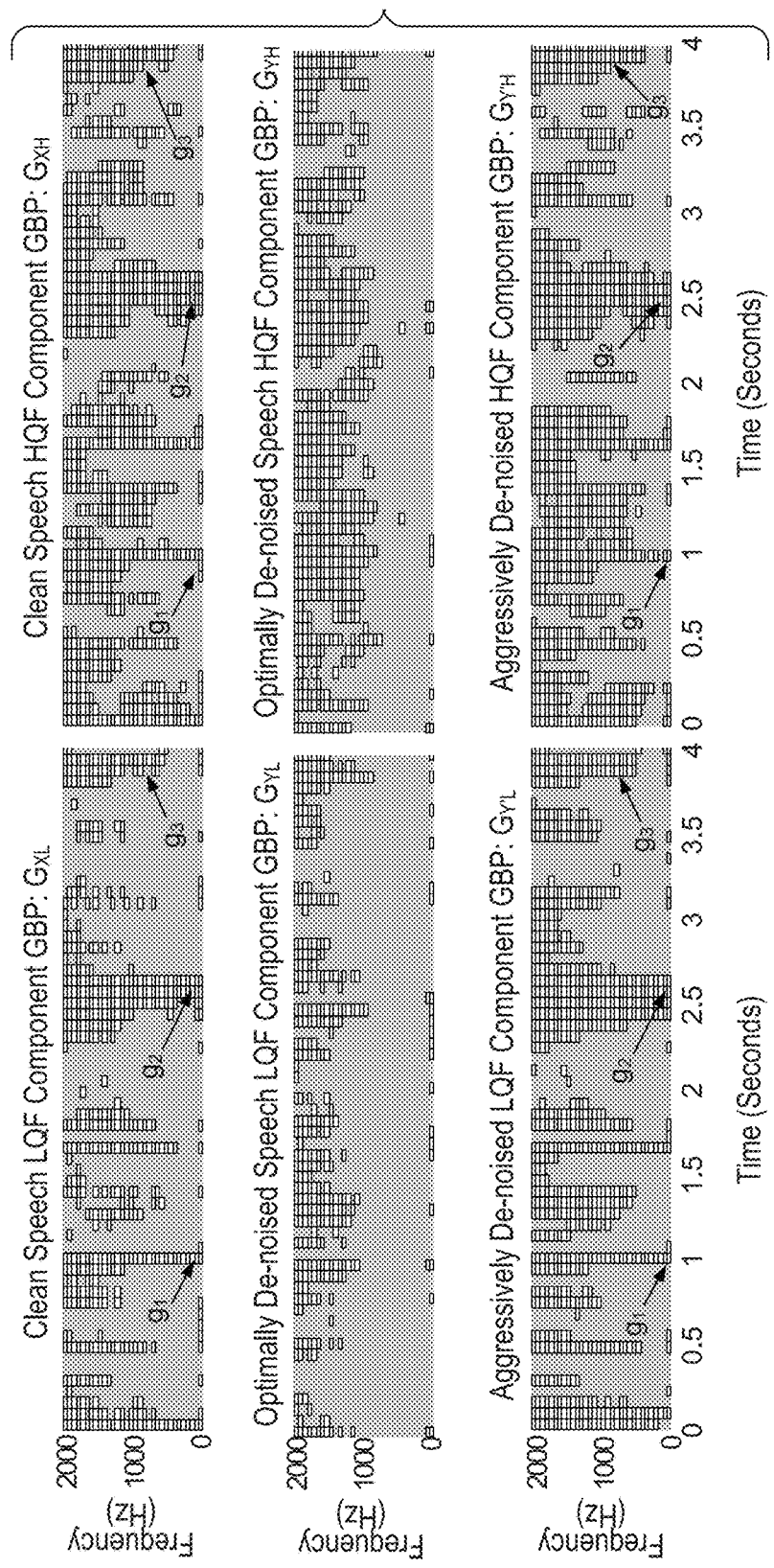
FIG. 13 shows data corresponding to Low frequency Gap Binary Patterns of for clean/noisy speech samples processed using the exemplary method of FIG. 2b.

FIG. 13 shows that using the selected aggressive de-noising regularization parameters will lead to finding a much more accurate gap patterns of the clean speech components. In particular, FIG. 13 shows Low frequency Gap Binary Patterns of $X_L, X_H, Y_L, Y_H, Y_L'$ and $Y_H'$ for clean/noisy speech samples. It can be seen that gaps (shown with $g_1, g_2, g_3, g_4$) which are filled with noise in $Y_L$ and $Y_H$, are visible in $Y_L'$ and $Y_H'$. SM($G_{X_L}$, $G_{Y_L}$')=0.76, SM($G_{X_H}$, $G_{Y_H}$')=0.79, SM($G_{X_L}$, $G_{Y_L}$)=0.54, SM($G_{X_H}$, $G_{Y_H}$)=0.57.

Figure 14:
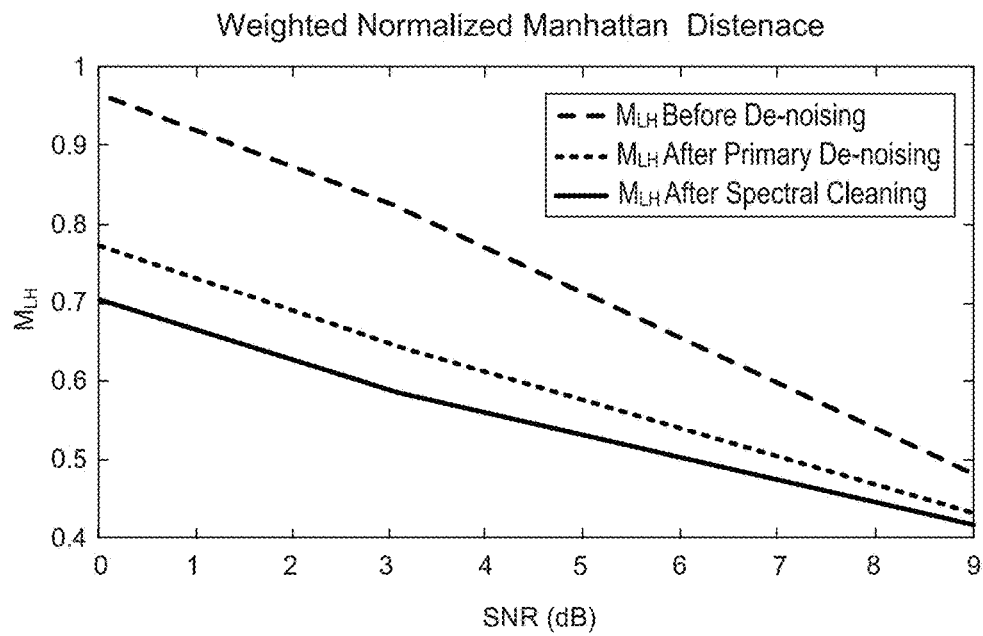
FIG. 14 shows data demonstrating the effect of each initial de-noising and spectral cleaning on the weighted normalized Manhattan distance $M_{LH}$ measured on noisy speech samples corrupted with various randomly created multi-talker babbles processed according to Example III.

FIG. 14 shows the effect of each initial de-noising and spectral cleaning on the weighted normalized Manhattan distance $M_{LH}$ measured on 1000 noisy speech samples corrupted with various randomly created multi-talker babbles. As it can be seen the effect of spectral cleaning decreases with increasing SNR.

Example III

As discussed above, the exemplary method 300 provides a babble noise reduction method (e.g., a SEDA-RT) that solves the ineffectiveness of simple temporal/spectral thresholding. Example III, as described herein, provide a detailed description of an exemplary embodiment of the three stages of exemplary method 300 (e.g., SEDA-RT), methods for clinical testing of the exemplary method, and collected data from CI users using SEDA-RT. In addition, the speed and latency of the exemplary embodiment of method 300 are measured using different computing machines (e.g., cell phones, tablets, and computers).

1. Classification

In step 304, each frame of an input signal may be classified into a first category corresponding to the noise being stronger than the speech signal, or a second category corresponding to the speech signal being stronger than the noise. In particular, the exemplary method 300 may utilize a classifier which is capable of classifying the relatively short frames of the noisy signal into one of the two following categories:

3. Noise dominated frames: frames in which the noise is significantly stronger than speech 4. Speech dominated frames: frames in which the speech is significantly stronger than noise The classifier may be computationally efficient and accurate, even when applied to short frames (less than 100 ms in duration) corrupted by speech-like non-stationary noise (e.g., Multi-talker babble). It may also work well on short frames for the purpose of achieving a low-latency implementation.

1.1 Overall Versus Local SNR

For a given noisy signal X=S+N where S is the signal and N is the noise, the overall SNR (Signal-to-Noise Ratio) is defined as $$SNR_{dB} = 20\log_{10}\left(\frac{S_{rms}}{N_{rms}}\right) \quad (5)$$

where the root mean square (RMS) value of a signal S is defined as:

$$S_{rms} = \sqrt{\frac{1}{n}(s_1^2 + s_2^2 + \ldots + s_n^2)}$$

Figure 15:
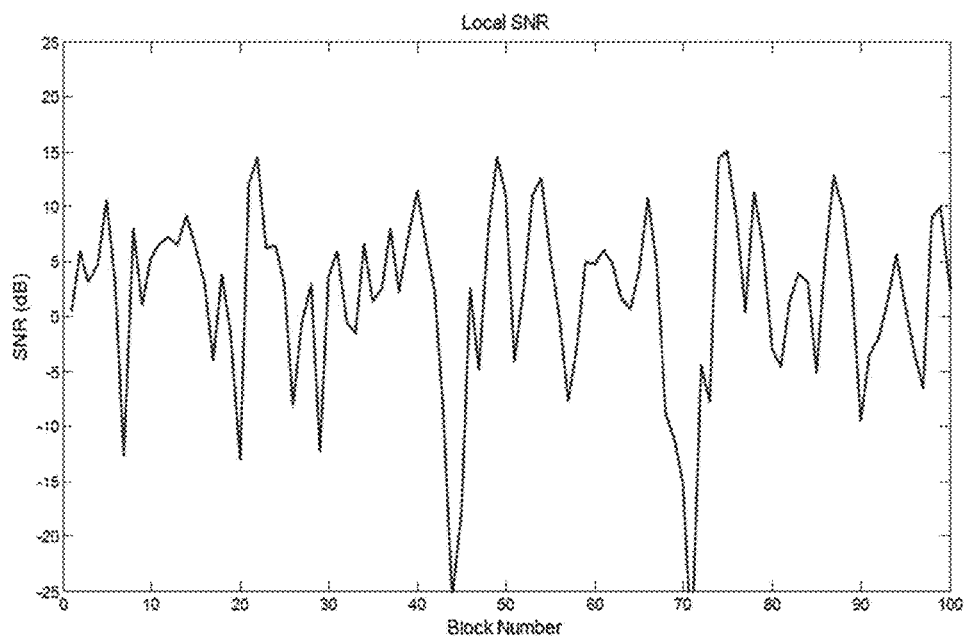
FIG. 15 shows data corresponding to a local Signal-to-Noise Ratio (SNR) for noisy speech sample with overall SNR=6; Frame duration=90 ms according to Example Ill.

If a noisy signal is partitioned with a fixed overall SNR into shorter frames, each frame will have a SNR which can be smaller or larger than the overall SNR. In contrast to overall SNR which is estimated over the entire length of the signal, the local SNR is estimated over short frames of the noisy signal. FIG. 15 shows the local SNR of short frames of a noisy speech with overall SNR=6 dB.

1.2 Buffer Zone

Because the SNR is a continuous value (i.e., not discrete), in order to define two classes (speech-dominated vs noise-dominated), a certain predetermined SNR value to may be established as the border value between the two classes. The predetermined SNR value may be preselected or may be manually inputted by a user. If SNR=0 dB is selected as this border value, then all the frames with SNR<0 dB will be classified as noise-dominated and frames with SNR>0 dB will be classified as speech-dominated. Because two classes adjoin at SNR=0, there will be frames with SNR values very close to zero on either positive or negative sides, which are classified into different groups (e.g., a frame with SNR=−0.01 dB will be classified as noise dominated where a frame with SNR=+0.01 dB will be classified as speech dominated). In order to make two classes more distinct and avoid classifying frames with negligible SNR difference into different classes, a narrow buffer zone may be defined around the border SNR (0 dB). A frame with SNR belonging to this buffer zone may be classified as either speech-dominated or noise-dominated. For example, this buffer region may be set as −1.5 dB to +1.5 dB. (Rationale: Consider the classification of each minute of a 24-hour period as either day or night. There will be minutes during dawn or dusk that can be correctly classified as either class).

1.3 Feature Selection

The first step for a good classification is choosing good features. Features which are robust and relevant with minimum variance for different conditions are always preferred. Step 304 utilizes features which are sensitive to changes of SNR in very short frames of speech, corrupted by multi-talker babble noise.

In one exemplary embodiment, a SEDA-RT classifier, four different features may be selected. However, it is contemplated that any one or more of these four different features may be used in any combination. Each feature is discussed briefly below and a score of their quality is provided. Each of the features may subsequently be given a weighting factor based on their quality score.

In one exemplary embodiment discussed below, the exemplary results are computed over short frames of speech corrupted by multi-talker babble. The length of each frame is $2^{12}$ samples ($\approx$90 ms for a sampling rate of fs=44100 samples/second).

1.3.1 Feature1: Envelope Variance

To compute this feature, the envelope of the incoming noisy speech frame is first extracted. For an arbitrary frame $F_i$ the envelope can be calculated as follows:

$$e_i(n) = \frac{1}{L_w} \sum_{k=-\frac{L_w}{2}}^{\frac{L_w}{2}} |F_i(k+nh)| w(k) \quad (6)$$

where: $L_w$ is the window length, w is the window type and h is the hop size. Here, non-overlapping rectangular windows with $h=L_w$ may be used. Then the envelope will be normalized:

$$\hat{e}_i(n) = \frac{e_i(n)}{\max(e_i)} \quad (7)$$

Finally, the envelope variance may be obtained by:

$$f_1(i) = \text{var}(\hat{e}_i) = \frac{1}{N_w} \sum_{n=1}^{N_w} (\hat{e}_i(n) - \mu_i)^2 \quad (8)$$

where: $N_w$ is the total number of windows in a frame and $$\mu_i = \frac{1}{N_w}\sum_{n=1}^{N_w} \hat{e}_i(n).$$

Feature quality may be estimated using a Fischer score:

$$S_1 = \frac{\sum_{j=1}^{N_c} n_j(\mu_j - \mu)^2}{\sum_{j=1}^{N_c} n_j \sigma_j^2} \qquad (9)$$

Where $N_c$ is the number of classes (in one particular embodiment, $N_c=2$), $\mu_j$ is the mean of the feature in class j, $\mu$ is the overall mean of the feature, $\rho_j$ is the variance of the feature in class j and $n_j$ is the number of instances in class j.

In the exemplary embodiment as specified above in Section 1.3, with the number of classes, $N_c=2$, experiments show that for this feature, the quality score increases by increasing the window's length up to a certain point and then start to decrease.

1.3.2. Feature2: Envelope Mean-Crossing

To obtain this feature, the normalized envelope of the frame obtained from (6) and (7) may again be used. Mean crossing is the number of times that the normalized envelope crosses its mean. For an arbitrary frame of the signal the mean crossing is calculated as follows:

$$f_2(i) = \frac{1}{2N_w}\sum_{k=2}^{N_w} |\text{sign}(\hat{e}_i(k) - \mu_{\hat{e}_i}) - \text{sign}(\hat{e}_i(k-1) - \mu_{\hat{e}_i})| \qquad (10)$$

where: $\hat{e}_i$ and $\mu_{s_i}$ are the normalized envelope and its mean respectively and sign(x) is defined as:

$$\text{sign}(x) = \begin{cases} 1, & x > 0 \\ -1, & x < 0 \\ 0, & x = 0 \end{cases}$$

Estimating the feature quality with Fischer score shows that the score decreases by increasing the window's length. Because the main parameter which determines the quality score of both feature 1 and feature 2 is the window's length, the window's length $L_w \in \mathbb{N}$ can be obtained, which maximizes the sum of two feature scores:

$$\text{argmax}_{L_w \in \mathbb{N}} S_1 + S_2 = \frac{\sum_{j=1}^{N_c} n_j^1(\mu_j^1 - \mu^1)^2}{\sum_{j=1}^{N_c} n_j^1 \sigma_j^{1\,2}} + \frac{\sum_{j=1}^{N_c} n_j^2(\mu_j^2 - \mu^2)^2}{\sum_{j=1}^{N_c} n_j^2 \sigma_j^{2\,2}} \qquad (11)$$

In the exemplary embodiment as specified above in Section 1.3, with the number of classes, $N_c=2$, experiments show that with $L_w=85$ the average $S_1+S_2$ is maximized.

1.3.3. Feature3: Signals RMS Ratio after and Before Time Domain Thresholding

To obtain this feature, for a frame $F=(x_1, x_2, \ldots, x_L)$, $r(F,\tau(F))$ is defined as the ratio of the frame's root mean square (RMS) value after hard thresholding with threshold $\tau(F)$ to its original RMS value:

$$f_3(i) = \frac{h_{rms}(F, \tau(F))}{F_{rms}} \qquad (12)$$

where: $h(F, \tau(F))$ is the hard threshold of the signal F with threshold $\tau(F)$ or:

$$h(F, \tau(F)) = \{h_1, h_2, \ldots, h_n\} \text{ where: } h_i = \begin{cases} 0, & |x_i| \leq \tau(F) \\ x_i, & |x_i| > \tau(F) \end{cases} \qquad (13)$$

and define:

$$\tau(F) = K\frac{1}{L}\sum_{i=1}^{L}|x_i| \qquad (14)$$

The only determining parameter for the quality of this feature is K and this feature can be optimized by finding the value of K which maximizes the feature's Fischer score:

$$\text{argmax}_{K \in \mathbb{R}} S_3 = \frac{\sum_{j=1}^{N_c} n_j(\mu_j - \mu)^2}{\sum_{j=1}^{N_c} n_j \sigma_j^2}$$

In the exemplary embodiment as specified above in Section 1.3, experiments show that with $K=1.9$ the average of $S_3$ is maximized.

This feature is directly extracted from a noisy speech frame in a time domain. First, the RMS value of the frame and its RMS value after hard thresholding with a suitable level may be obtained. Then, the ratio of these two RMS values may be obtained. The thresholding is directly applied to the signal in the time domain.

1.3.4. Feature4: Entropy

To obtain this feature, the entropy of each frame may be obtained using its histogram. This is the histogram of the sample values in the noisy speech frame. To compute the entropy of a noisy speech frame, an "estimate" the probability distribution of that frame is obtained. The histogram of the frame may provide this "estimation". The histogram of the noisy speech frame shows the distribution of the samples values over a number bins. These bins divide the entire range of sample values into a series of non-overlapping intervals.

Figure 16:
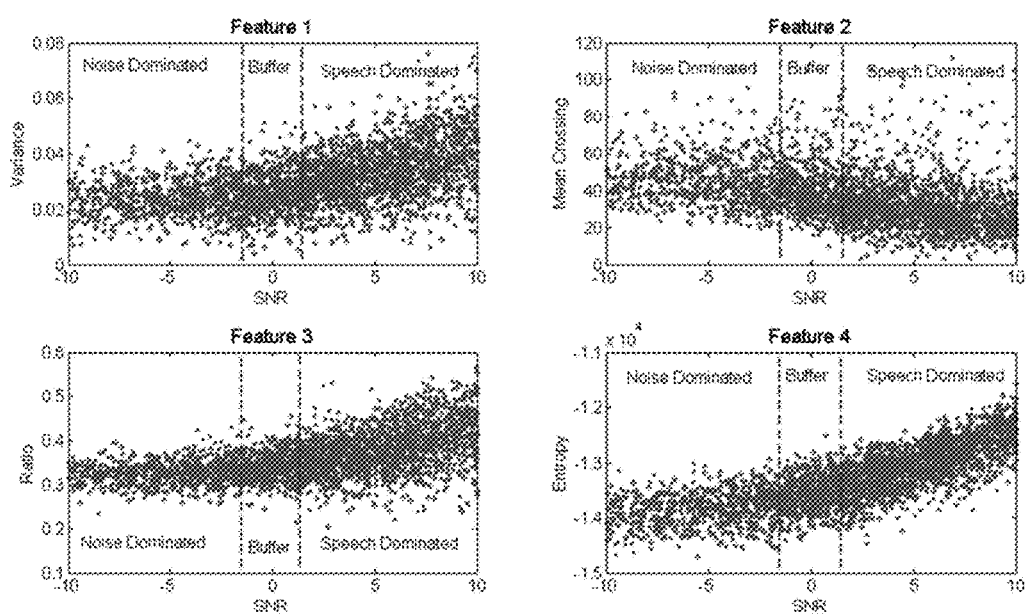
FIG. 16 shows data corresponding to variation of features for four exemplary different features for characterizing a sample audio signal as compared to SNR over 90 ms of noisy speech frames (samples) according to Example III.

This can be written as follows:

$$f_4(i) = -\Sigma_{k=1}^{N} H_{F_i}(k)\log_{10}(H_{F_i}(k)) \qquad (15)$$

where $H_{F_i}$ is the histogram of frame $F_i$. The main adjustable parameter for this feature is the width and the number of bins in the histogram. Again, the optimal bin-width and number-of-bins may be determined by maximizing the Fischer score of this feature. In the exemplary embodiment as specified above in Section 1.3, this feature is by far the most effective and robust feature among the four selected features (see FIG. 16).

1.4 Weighted PCA (Principle Component Analysis)

The goal of this section is to reduce the correlation (redundancy) between the features by generating a new smaller set of uncorrelated features. The quality of each feature is taken into account and given a relative weight to each feature based on its quality score, as determined above.

1.4.1 PCA (Principle Component Analysis)

Assuming $\mathcal{F}$ is the feature vector and $N_F$ is the total number of frames can be represented as follows:

$$\mathcal{F} = \begin{bmatrix} f_1 \\ f_2 \\ f_3 \\ f_4 \end{bmatrix}_{4 \times N_F} \text{ and } M = \begin{bmatrix} \mu_1 & \cdots & \cdots & \mu_1 \\ \mu_2 & \cdots & \cdots & \mu_2 \\ \mu_3 & \cdots & \cdots & \mu_3 \\ \mu_4 & \cdots & \cdots & \mu_4 \end{bmatrix}_{4 \times N_F}$$

where $\mu_1$ to $\mu_4$ are the mean values of the features. First, remove the mean of each feature to obtain:

$$F_0 = F - M. \tag{16}$$

Assuming T is the transformation matrix, it can be obtained that:

$$F_d = TF_0. \tag{17}$$

where: $F_d$ is the de-correlated feature vector. It may be assumed that $C_d$ is the covariance matrix of $F_d$ and it is rank-ordered based on its eigenvalues. Because all features in $F_d$ are de-correlated, the non-diagonal elements of its covariance matrix must be zero. Going back to the zero mean feature vector $F_0$, the covariance matrix $C_0$ of $F_0$ can be obtained as follows:

$$C_0 = \frac{1}{N} F_0 F_0^T \tag{18}$$

Now using (17) and (18), it can be obtained that:

$$C_d = \frac{1}{N} F_d F_d^T = \frac{1}{N} [TF_0][TF_0]^T = T\left[\frac{1}{n} F_0 F_0^T\right] T^T = T C_0 T^T \tag{19}$$

$C_d$ is known to be a diagonal matrix. In order to diagonalize the symmetric matrix of $C_0$ the orthogonal matrix of its eigenvectors may be created. Assuming r is the rank of covariance matrix $C_0$, the eigenvectors of $C_0$ and their associated eigenvalues may be written as:

$\{\bar{v}_1, \bar{v}_2, \ldots, \bar{v}_r\}$ and $\{\lambda_1, \lambda_2, \ldots, \lambda_r\}$ such that: $C_0 \bar{v}_i = \lambda_i \bar{v}_i$.

Now we define: $V = [\bar{v}_1 \; \bar{v}_2 \; \ldots \; \bar{v}_r]$ and using (19) we have:

$$C_d = V^T C_0 V \Rightarrow T = V^T \tag{20}$$

That means the transform matrix T is a matrix which its rows are the eigenvectors of the covariance matrix $C_0$. Having T, the original feature vector $F_0$ may be de-correlated as follows:

$$F_d = TF_0. \tag{21}$$

Because in this exemplary embodiment utilizes four original features, $N_f = 4$, therefore, $r \leq N_f$. In the case of $r < N_f$, $N_f - r$ arbitrary orthonormal vectors may be selected to complete the V. These orthonormal vectors don't change the result because they are associated with zero variance features.

1.4.2 Weighting the Features

Because the above-selected features have different quality, the PCA does not treat them equally. In order to take the feature's importance into account, a weight factor is assigned to each feature. The result of the Fischer score is used for weighting the features. The weight factors for each feature is selected based on its average Fischer score obtained in previous section:

The weighted covariance matrix $C_0$ will be obtained as:

$$C_0 = \frac{1}{N} W F_0 F_0^T W^T \tag{22}$$

where $$W = \begin{bmatrix} w_1 & 0 & \cdots & 0 \\ 0 & w_2 & \cdots & 0 \\ \cdots & \cdots & \cdots & \cdots \\ 0 & 0 & \cdots & w_{N_F} \end{bmatrix}$$

Figure 17:
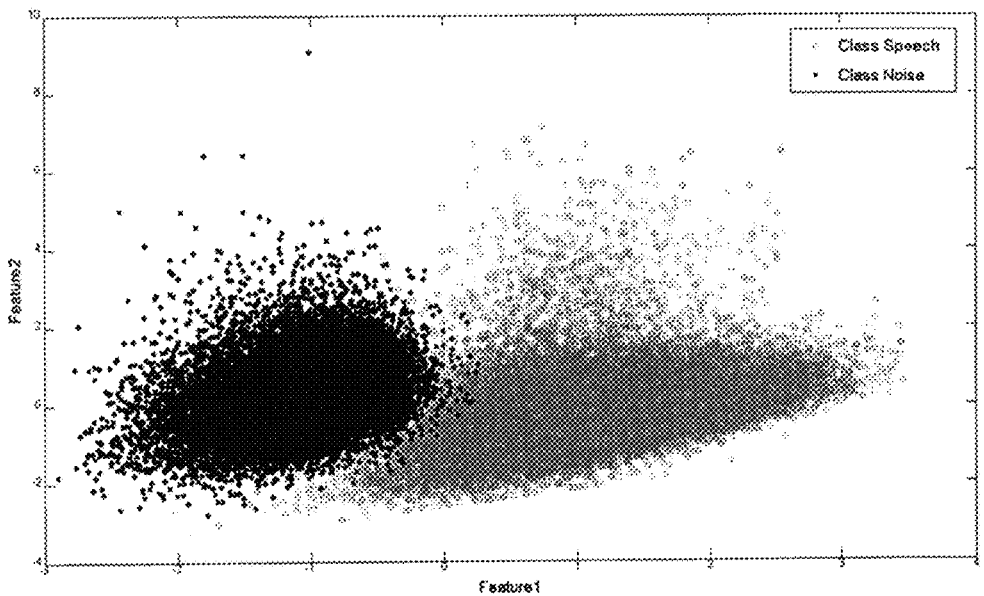
FIG. 17 shows data corresponding to a scatter plot of two de-correlated features according to Example III.

W is a diagonal $N_f \times N_f$ weighting matrix and $w_i$ is the weighting factor for ith feature. In SEDA-RT classifier $$N_F = 4 \text{ and } W = \begin{bmatrix} w_1 & 0 & 0 & 0 \\ 0 & w_2 & 0 & 0 \\ 0 & 0 & w_3 & 0 \\ 0 & 0 & 0 & w_4 \end{bmatrix} = \begin{bmatrix} S_1 & 0 & 0 & 0 \\ 0 & S_2 & 0 & 0 \\ 0 & 0 & S_3 & 0 \\ 0 & 0 & 0 & S_4 \end{bmatrix} = S$$

where $S_1$ to $S_4$ are the average Fischer scores of the four original features. After completing this stage, four new de-correlated features are obtained, which are ranked based on their variances and the first two features with the highest Fischer score as shown in FIG. 17.

1.5 Training with GMM

For training the classifier, a Gaussian Mixture Model (GMM) may be used. A GMM is the weighted sum of several Gaussian distributions:

$$p(\mathcal{F}_d | \mu, w, C) = \Sigma_{i=1}^{N_g} w_i \mathcal{N}(\mathcal{F}_d | \mu_i, C_i) \tag{23}$$

where $\mathcal{F}_d$ is a d-dimensional feature vector (For this exemplary classification, there are only two dimensions or d=2), $w_i$, $\mu_i$, and $C_i$ are the weight factor, mean and covariance of the ith Gaussian distribution respectively. A Gaussian distribution $\mathcal{N}(\mathcal{F}_d | \mu_i, C_i)$ can be written as:

$$\mathcal{N}(\mathcal{F}_d | \mu_i, C_i) = \frac{1}{(2\pi)^{\frac{d}{2}} \sqrt{|C_i|}} e^{\left\{-\frac{1}{2}[\mathcal{F}_d - \mu_i]^T C_i^{-1} [\mathcal{F}_d - \mu_i]\right\}} \tag{24}$$

In addition, $$\Sigma_{i=1}^{N_g} w_i = 1. \tag{25}$$

For an arbitrary data sample k with a feature vector $\mathcal{F}^k$, the probability that the sample belongs to a Gaussian n can be calculated as:

$$p_n^k = \frac{w_n \mathcal{N}(\mathcal{F}^k | \mu_n, C_n)}{\sum_{i=1}^{N_g} w_i \mathcal{N}(\mathcal{F}^k | \mu_i, C_i)} \tag{26}$$

$p_n^k$ is called soft responsibility function. In this example, each class is divided into a number of (e.g., three) clusters and each cluster may be modeled by a Gaussian model. In order to train the model, an iterative method, such as the Expectation-Maximization (EM) algorithm, may be used.

In order to fit a Gaussian to each cluster the following logarithmic function is maximized:

$$\log \{p\vec{f}|\mu,C,w)\} = \Sigma_{k=1}^{N_F} \log \{\Sigma_{i=1}^{N_g} w_i \mathcal{N}(f^k|\mu_i, C_i)\} \quad (27)$$

where the $N_F$ is the number of data samples (i.e., the number of audio frames). First, $w_i$, $\mu_i$, $C_i$ are initialized, and then soft responsibilities $p_i^k$ may be obtained with $w_i$, $\mu_i$, $C_i$ values. The $w_i$, $\mu_i$, $C_i$ values may be updated using the new soft responsibilities as follows:

$$\mu_i^{new} = \frac{\sum_k p_i^k \vec{f}^k}{\sum_k p_i^k} \quad (28)$$

$$\omega_i^{new} = \frac{\sum_k p_i^k}{N_F}$$

$$C_i^{new} = \frac{\sum_k p_n^k (\vec{f}^k - \mu_i^{new})(\vec{f}^k - \mu_i^{new})^T}{\sum_k p_n^k}$$

Figure 18:
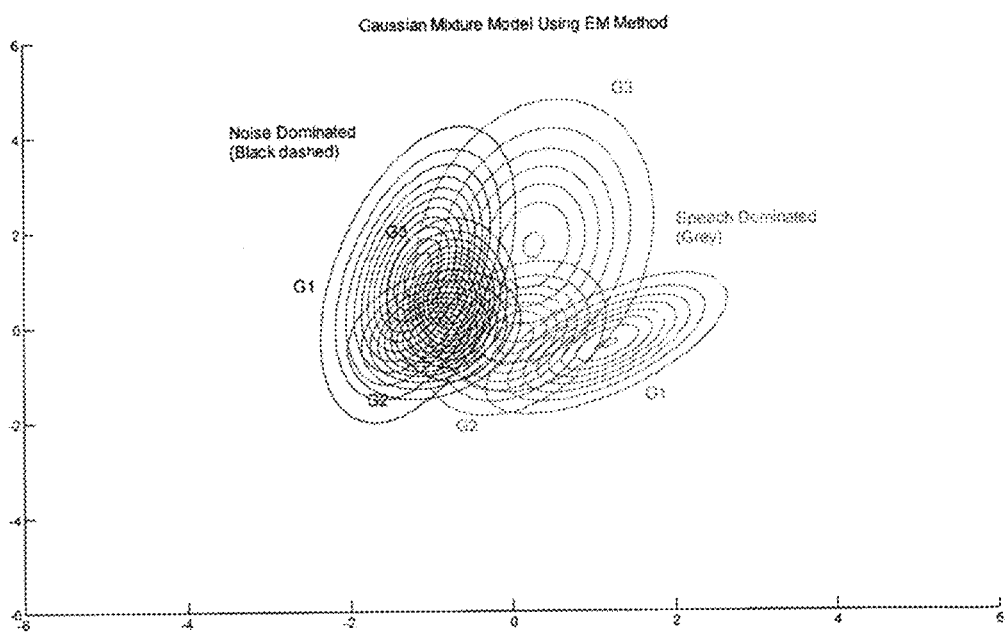
FIG. 18 shows data corresponding to a Gaussian Mixture Model (GMM) using a Expectation-Maximization (EM) method as described Example III.

The above stages are repeated until the convergence of (27). (See FIG. 18).

1.6 Classification Using MAP (Maximum a Posteriori Estimation)

After finishing training, the probability of each test feature set f belonging to a class X may be obtained by:

$$\arg \max_x [P\vec{f}|\text{class}_X)P(\text{class}_X)]$$

$X \in \{S,N\}$ S: Speech Dominated N: Noise Dominated. (29)

where $$P(\vec{f}|\text{class}_X) = \sum_{i=1}^{N_g^X} w_i \mathcal{N}(\vec{f}|\mu_i, C_i). \quad (30)$$

$N_g^X$ is the number of Gaussians belonging to the class X. $P(\text{class}_x)$ also can be easily obtained during training by computing the number of class X occurrence divided by the total data samples in training data. $\mu_i$, $C_i$ and $w_i$ are also available from the GMM training process.

The values $P(\text{class}_N)$ and $P(\text{class}_S)$ change as a function of the global SNR, therefore these two probabilities should be continuously updated based on the estimated global SNR (The frequency of global SNR detection update depends on our assumption of how fast the noisy environment varies.). A basic, computationally efficient method may be used to estimate the global SNR using the same features which were used to estimate the local SNR. The global SNR may be estimated once every few second and the result may be used to update $P(\text{class}_N)$ and $P(\text{class}_S)$. Because the global SNR is estimated over long windows, the features perform very well in this case and the accuracy of global SNR estimation is very high.

1.7 Performance Evaluation

Because de-noising threshold levels in SEDA-RT are extracted from the information taken from the noise dominated frames, in order to provide the performance of SEDA-RT, for the frames which are classified as noise dominated, there is a need to make sure that they are actually noise dominated, and not speech dominated frames. Conversely, classifying few noise dominated frames as speech dominated will not have a drastic negative effect on the result. Therefore, in the exemplary method as described in this Example may be very strict when categorizing a frame as noise dominated, even if it comes at the cost of misclassifying some noise dominated frames as speech dominated.

Using MAP for each noisy speech frame with feature vector $\vec{f}$ two probabilities of $P(\vec{f}|\text{class}_N)$ and $P(\vec{f}|\text{class}_p)$ may be obtained. Normally, a frame may be classified into a class with the higher probability (Assuming $\alpha=1$ in equation 31). Alternatively, to be stricter about one class, $\alpha$ may be changed to a suitable number.

$$f(i) \in \begin{cases} \text{class}_S & P(\vec{f}|\text{class}_N) \leq \alpha P(\vec{f}|\text{class}_S) \\ \text{class}_N & P(\vec{f}|\text{class}_N) > \alpha P(\vec{f}|\text{class}_S) \end{cases} \quad (31)$$

In this Example, SEDA-RT classifier was evaluated using K-fold cross validation method (K=8) and the average values of following six accuracy metrics were measured.

$$P_N = \frac{C_N}{C_N + f_N^+} \quad (32)$$

$$R_N = \frac{C_N}{C_N + f_N^-}$$

$$F_N = \frac{2 P_N R_N}{P_N + R_N}$$

$$P_S = \frac{C_S}{C_S + f_S^+}$$

$$R_S = \frac{C_S}{C_S + f_S^-}$$

$$F_S = \frac{2 P_S R_S}{P_S + R_S}$$

where C, $f^+$ and $f^-$ are correct, false positive and false negative detection, respectively. The average performance metrics slightly changed by changing the width of the buffer zone as well as the overall SNR values. However, in most cases all six metrics remained well above 90%. The most important metric on which the performance of SEDA-RT depends is $P_N$. It is desirable for $P_N$ to be always more than 95% for a desirable de-noising result. In order to make sure that $P_N > 0.95$ at all times, a value of $\alpha > 1$ may be chosen. In this particular example, the value of $\alpha$ is set to 1.25, which ensures a high average for $P_N$. However, it usually causes a small decline in $R_N$ which will not have any detrimental effect on de-noising performance.

2. De-Noising

As discussed above, oversampling can potentially decrease the overlapping between speech and noise coefficients and increase the performance of thresholding-based de-noising or other separation methods. Decomposing a signal into its frequency bands using a filter bank (e.g., Gammatone filter bank) is an example of an oversampled transformation. In this example, the oversampling rate is equal to the number of filters in the filter bank. Sparsification, using an oversampled wavelet transform (given the signal or noise can be sparsely represented in that particular wavelet domain) is an effective way to minimize the overlapping problem. However, sparsification is an iterative process which often cannot be implemented in real-time algorithms due to its high computation. Moreover, human speech cannot be efficiently sparsified in most wavelet domains unless some additional measures are implemented (e.g., MCA). The representation of the clean speech samples in oversampled TQWTs (Tunable Q Wavelet Transform) exhibits some limited degree of group sparsity which does not exist in babble samples. SEDAR-RT employs this property, and a few other properties to de-noise the speech samples which are corrupted by multi-talker babble. In general, if signal a S is decomposed into n sub-bands of $w_1$ to $w_n$ using the transform T:

$$S \xrightarrow{T} [w_1, w_2, \ldots, w_n]$$

The redundancy (Oversampling rate) of the transform T can be calculated as:

$$r_T = \frac{\sum_{i=1}^{n} f_{w_i}}{f_s} \quad (33)$$

where: $r_T$ is the redundancy of the transformation T, $f_s$ and $f_{w_i}$ are the sampling rates of S and $w_i$ respectively.

Note that increasing the redundancy will increase number of samples and consequently the amount of required computation by the same factor. Hence using a conventional filter bank in which each output channel has the same sampling frequency as the input signal, has the disadvantage of increasing the computational costs in real-time applications.

Figure 19:
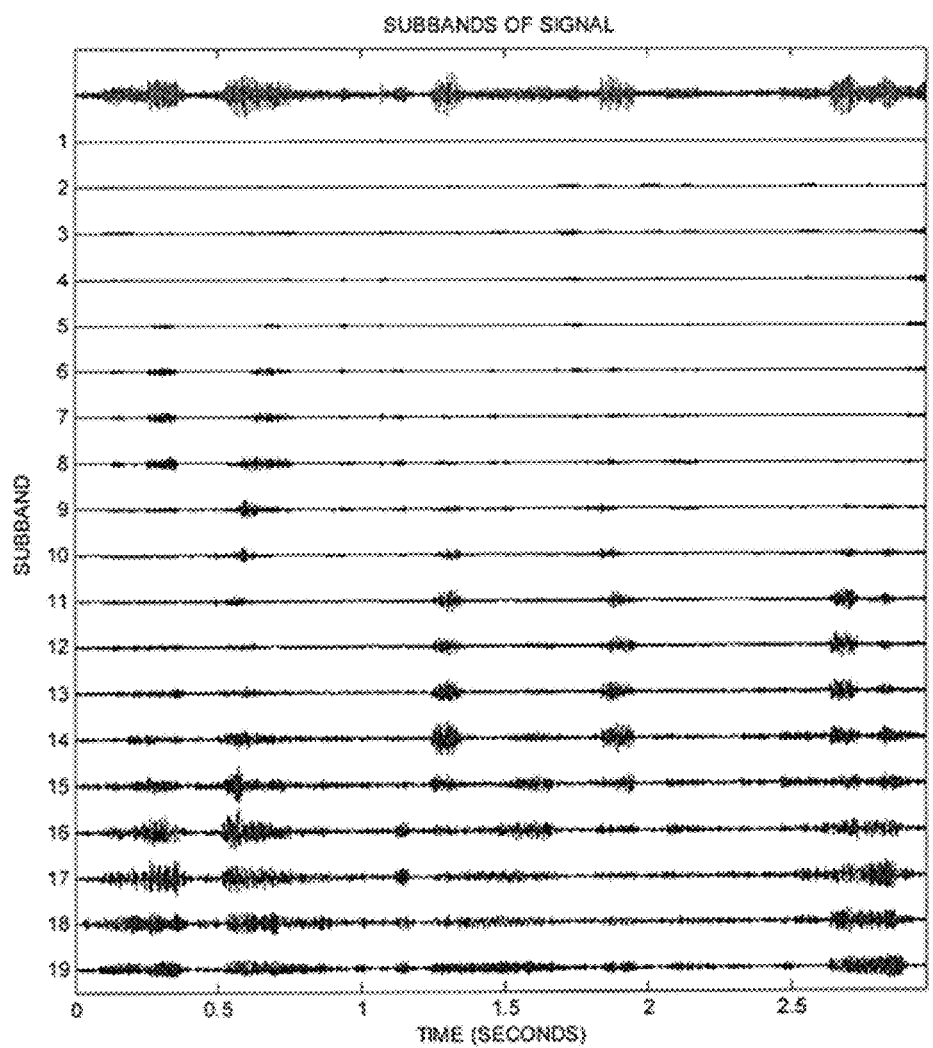
FIG. 19 shows data corresponding to a Tunable Q-Factor Wavelet Transform (TQWT) of three seconds of noisy speech (speech plus babble) and its sub-bands as described Example III.
Figure 20:
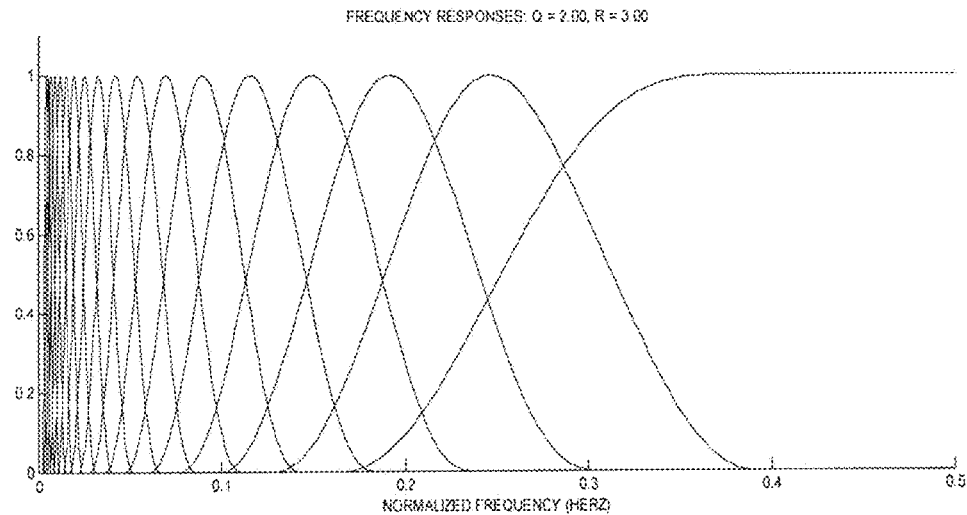
FIG. 20 shows data corresponding to a TQWT frequency response as described Example III.

In order to be able to adjust the oversampling rate to an optimal level, any suitable wavelet transform may be used. In particular, the "Tunable Q-factor Wavelet Transform" (TQWT) may be used. A TQWT is defined by three parameters which can be adjusted independently: Q-factor, the redundancy, and the number of levels. (FIG. 19). The Q-factor is a measure of the oscillatory behavior of a pulse; it is defined as the ratio of its center frequency to its bandwidth. The redundancy is the over-sampling rate of the wavelet transform and should be always greater than 1. Adjustability of these three parameters is one advantage of TQWT transform, because different representation of the signal can be obtained by changing the parameters. SEDA-RT uses this advantage in a parallel de-noising technique. Another advantage of the TQWT is that its spectral properties, namely the frequency response of its sub-bands, are compatible with the human auditory system. The distribution of the center frequencies of the sub-bands and the shape of the frequency responses of the TQWT resemble Mel-scale and Gammatone filter banks that are designed to reflect the human auditory system (see FIG. 20).

2.1 Adaptive Group Thresholding

It is important to choose suitable threshold function and threshold levels. A high threshold level will remove the noise but distort the signal, whereas a low threshold level will preserve the signal but keep the noise. Moreover, hard thresholding is not always suitable and sometimes leads to very severe distortion. Before describing the adaptive group thresholding, hard and soft thresholding may be established. For a real-valued signal r, hard and soft thresholding with threshold level T are defined with $H_T(x)$ and $S_T(x)$ as follows:

$$H_T(x) = \begin{cases} 0, & |x| \leq T \\ x, & |x| > T \end{cases} \quad (34)$$

$$S_T(x) = \begin{cases} x+T, & x < -T \\ 0, & -T \leq x \leq T \\ x-T, & x > T \end{cases} \quad (35)$$

Adaptive group thresholding used in SEDA-RT is mainly based on the following three strategies:

1. For each sub-band i the threshold level should be just enough to remove most of the babble noise with minimum distortion of the target speech. Hence the threshold level in each sub-band should be selected based on the average noise level in that sub-band. Because the average noise level in each sub-band is not known, for a given sub-band i, the threshold level is estimated based on the l1 norm of the same sub-band i in the neighboring frames which are classified as noise dominated by the classifier.

2. For every frame, each sub-band may be divided into a number of sub-frames where each sub-frame consists of a few coefficients (typically 16). Within each sub-band hard and soft thresholding may be used alternatively for different sub-frames. Hard thresholding may be used for sub-frames with a relatively low l1 norm compare to the other sub-frames in the same sub-band. This will remove many small coefficients originating from the noise source. Recall that target speech is louder than any individual background talker and has some degree of group sparsity, therefore coefficients with small value spreading across the sub-band without forming a distinct group of coefficients, are more likely to originate from the babble source. A milder soft thresholding (with a smaller threshold level) will be used for sub-frames with high l1 norm. This will prevent distortion when a mixture of large and small original speech coefficients coming are concentrated in a group/cluster. Using hard threshold in these cases would eliminate the smaller coefficients and would lead to distortion.

3. In addition to using different thresholding strategies for different sub-frames within a sub-band, a general thresholding aggressiveness for a noisy speech frame is also determined based on the result of the classification. A more aggressive thresholding may be used for noise-dominated frames and less aggressive thresholding for speech-dominated frames. Details are given in following sub-sections.

As described herein, the term "adaptive group thresholding" refers to this combination of thresholding levels based on the amount of noisy speech present in each input audio frame.

2.1.1 Updating the Threshold Level

In SEDA-RT for every incoming frame, the threshold levels may be updated for all sub-bands based on the babble noise level. To update the threshold levels, for every sub-band, the average normalized l1 norm of that sub-band in the last M noise dominated frames may be obtained. Array A is defined as:

$$A = \begin{bmatrix} a_1 \\ a_2 \\ \vdots \\ a_{J+1} \end{bmatrix} \quad (36)$$

where:

$$a_i = \frac{1}{M}\sum_{k=1}^{M} \mu_{ik} \quad (37)$$

is the average of normalized l1 norm of the sub-band i over the last M noise dominated sub-bands.

$$\mu_{ik} = \frac{1}{L_i}\sum_{m} |w_{ik}(m)| \quad (38)$$

is the normalized l1 norm of the sub-band i of the noise dominated frame k and $L_i$ is the sub-band's length. The noise dominated frame k is denoted by $F_k^{Noise}$. Therefore: $w_k=\text{TQWT}(F_k^{Noise})$ where: $w_k=\{w_{1k}, w_{2k}, \ldots, w_{(J+1)k}\}$, J is the number of levels in our TQWT and $w_{ik}$ is sub-band i of the noise dominated frame k. M is an arbitrary number that depends on the variation of the ambient noise. For a steadier ambient noise, a larger M may be chosen and for a noise which varies quickly, a smaller M may be selected. In case of multi-talker babble, as the number of talkers increase, the M may be increased. Assuming a new noise dominated frame $F_{M+1}^{Noise}$ is detected, update each element of array A may be updated as follows:

$$a_i^{new} = \frac{(M-1)a_i^{old} + \mu_{i(M+1)}}{M} \quad (39)$$

Figure 21:
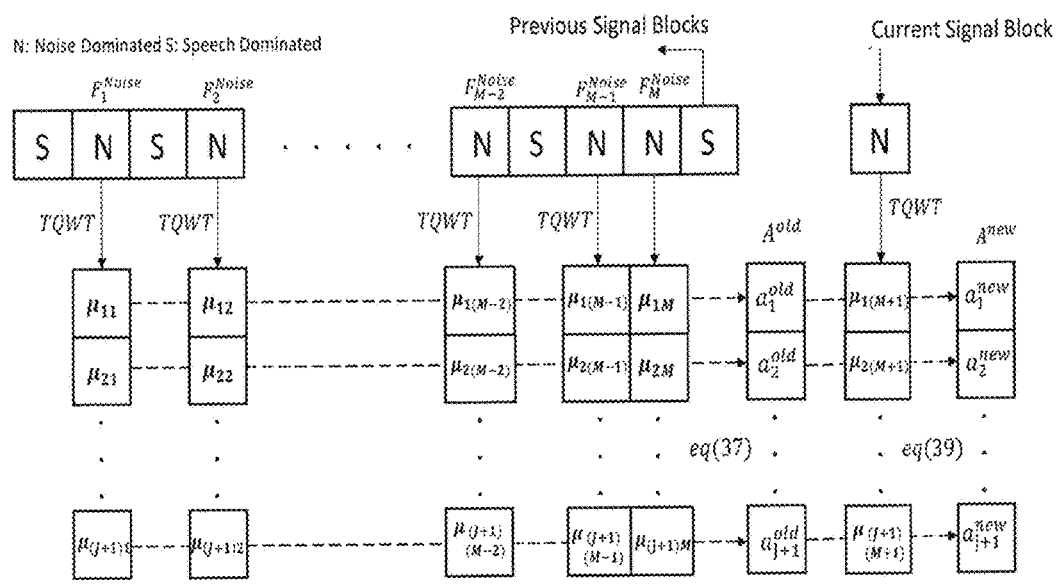
FIG. 21 shows an exemplary embodiment for a method for threshold updating as described Example III.

This updating process is shown in FIG. 21.

2.1.2 Thresholding

With this updated array of average noise level for all sub-bands, an adaptive group thresholding method may be implemented. Denoting by F an incoming frame of the noisy speech:

$w=\text{TQWT}(F)$ where $w=\{w_1, w_2, \ldots, w_{j+1}\}$

As discussed earlier, each TQWT sub-band will be divided into a number of sub-frames. For an arbitrary sub-band i:

$L_i = N_i L_{gw}$ where: $N_i$ is the number of sub-frames for sub-band i, $L_{gw}$ is the length of each sub-frame and $L_i$ is the sub-band's length. Assuming $sw_{ik}$ is the kth sub-frame of the ith sub-band:

$sw_{ik}=\{(w_i((k-1)L_{gw}+1), w_i((k-1)L_{gw}+2) \ldots, w_i(k L_{sw})\}$ (40)

Where: $k, i \in \mathbb{N}$; $1 \leq k \leq N_i$, and $1 \leq i \leq J+1$ $r_{ik}$ may be defined as the ratio of the average l1 norm of $sw_{ik}$ to the average l1 norm of sub-band i. $r_{ik}$ can be represented as:

$$r_{i,k} = \frac{1}{N_i}\frac{|w_i|_1}{|sw_{ik}|_1} \quad (41)$$

Each sub-frame $sw_{ik}$ may be classified as either high-energy or low-energy sub-frame based on its $r_{ik}$ value. Sub-frames with $r_{i,k}$ value greater than a certain threshold y (typically $2<\gamma<5$) will be classified as high energy sub-frames and a mild soft thresholding will be applied to them. Conversely, sub-frames with $r_{i,k}$ value smaller than y will be considered low energy sub-frames, and a more aggressive hard thresholding will be applied to them. This can be represented as:

$$\widetilde{sw}_{ik} = \begin{cases} H_{T_1}(sw_{ik}), & r_{ik} \leq \gamma \\ S_{T_2}(sw_{ik}), & r_{i,k} > \gamma \end{cases} \quad (42)$$

where: $T_1=\rho\tau a_i$, $T_2=\rho\beta\tau a_i$

Figure 22:
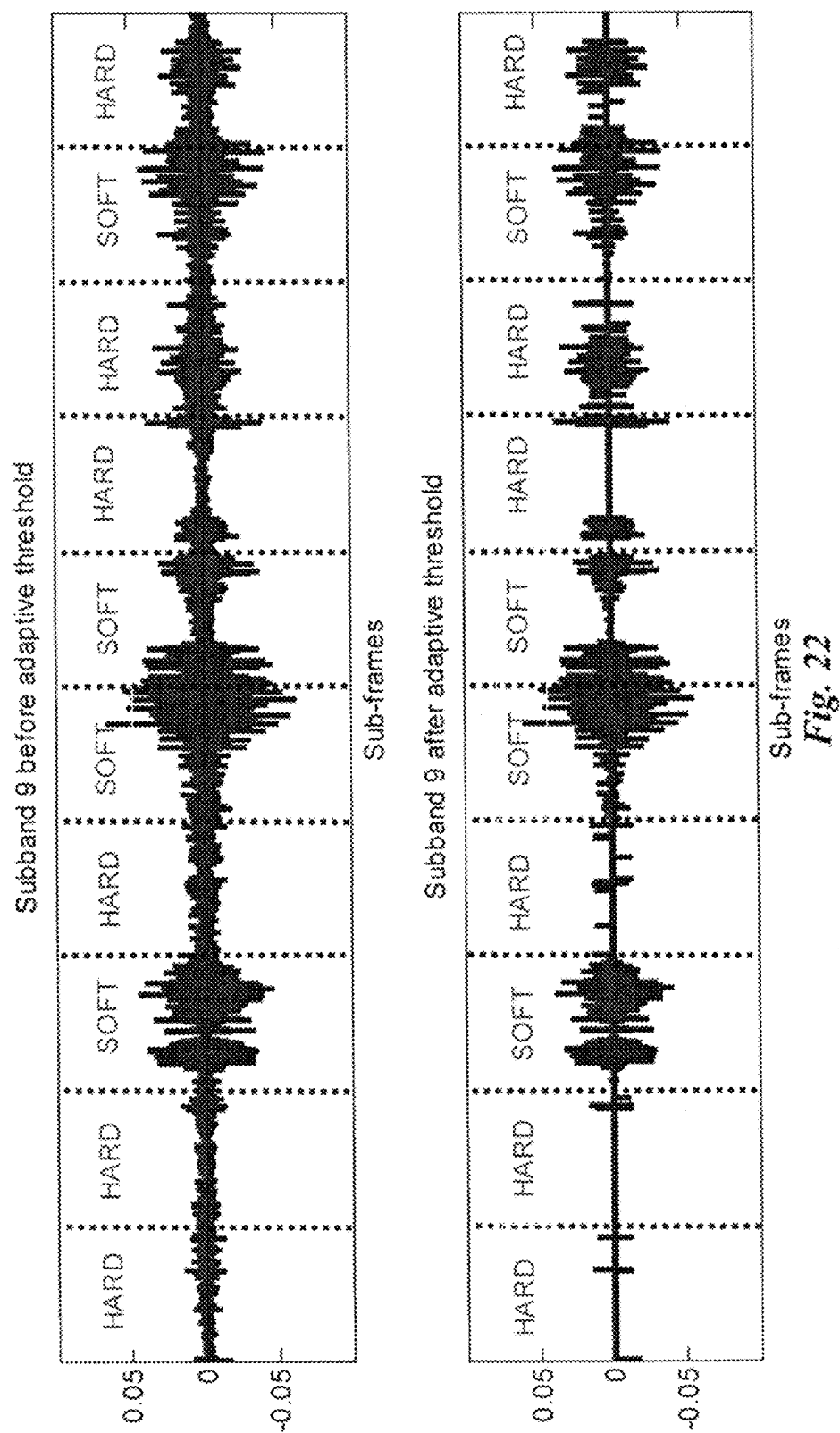
FIG. 22 shows data corresponding to an exemplary embodiment of adaptive group thresholding in a sub-band of TQWT, wherein threshold levels are different for hard and soft thresholding, as described Example III.

Note that in equation (42), $a_i$ is the updated average of normalized l1 norm of the sub-band i over the last M noise-dominated sub-bands. $\tau$ controls the thresholding aggressiveness based on the frame's class. $\tau$ is greater when the signal's frame is noise dominated and smaller when it is speech dominated (e.g., $\tau=1$ for speech dominated frames and $\tau=1.5$ for noise dominated frames). $\rho$ determines the desired overall de-noising aggressiveness. By increasing $\rho$, signal is de-noised more aggressively but are more likely to distort the signal ($1.5<\rho<3$ is the typical range). $\beta$ which is always smaller than 1 (In one particular embodiment, as shown in FIG. 22, $\beta=0.3$ is selected), determines the milder aggressiveness for soft thresholding.

2.2 Parallel De-Noising

Even using an adaptive group thresholding will not remove all the babble and will not prevent the original speech from distortion. To solve this problem, a parallel de-noising approach may be used. Parallel de-nosing may be used to further remove the residual noise and recover the distorted parts of the speech. It also has another benefit: it changes the behavior of the remaining babble noise. This advantage is further discussed in the next section.

In parallel de-noising the previously mentioned adaptive group thresholding in three parallel routes may be implemented with different wavelet settings. The three resulting de-noised signals will eventually be averaged. First, three different setting for the tunable Q wavelet transform may be chosen. Each setting will provide a different representation of the signal in the wavelet domain. Hence, implementing the adaptive group thresholding for each case will lead to slightly different versions of the de-noised signal.

To increase thresholding performance and have different wavelet representation for each TQWT, the following two considerations should be implemented:

1. Three wavelet transforms should have low, medium and high Q factors respectively. This will assure the speech representations in wavelet domain are different from each other.
2. Redundancy and number of levels in each TQWT should be selected so that the signal's energy is distributed over many sub-bands. The parameters r and J must be set to appropriately values, otherwise the signal energy may be concentrated in a few sub-bands which leads to less effective adaptive group thresholding.

Note that a good selection of Q, r and J for a certain incoming signal's frame duration, might not be optimal for another frame duration.

In this particular example, the selected values for a frame duration of $t^f \approx 90$ ms for a sampling rate of fs=44100 Hz samples/second are:

$Q_1=9, r_1=3, J_1=67$ $Q_2=5, r_2=3, J_2=43$ $Q_3=2, r_3=3, J_3=20$

Note that these values are not the only choices and other parameter values that satisfy the two above mentioned criteria may be acceptable. After parallel de-noising, there will be three different de-noised versions of the same frame. Since each de-noising process has been performed using different setting and parameters, the results will be different. Some areas of the speech might be distorted in one version while the same areas are not distorted in another version. By adding and averaging these three de-noised versions, some areas which are distorted in one version will be recovered by another and this substantially reduces the overall distortion.

Assuming F is an incoming noisy speech frame which is the mixture of the speech S and babble noise B.

$$F = S + B$$

This frame will be transformed into wavelet domain using three parallel TQWTs with three different settings:

$$w_1 = TQWT_1(F)$$

$$w_2 = TQWT_2(F)$$

$$w_3 = TQWT_3(F) \qquad (43)$$

where $w_1$, $w_2$ and $w_3$ are three different wavelet domain representations of frame f using three different sets of parameters.

The resulting $w_1$, $w_2$ and $w_3$ then will go through the adaptive group thresholding processes with different parameters. The wavelet representations $w_1$, $w_2$ and $w_3$ each comprise a different number of sub-bands with different values, therefore the adaptive group thresholding parameters will also be different for each case. If the adaptive group thresholding process is denoted with T:

$$\hat{w}_1 = T(w_1)$$

$$\hat{w}_1 = T(w_2)$$

$$\hat{w}_1 = T(w_2) \qquad (44)$$

Figure 23:
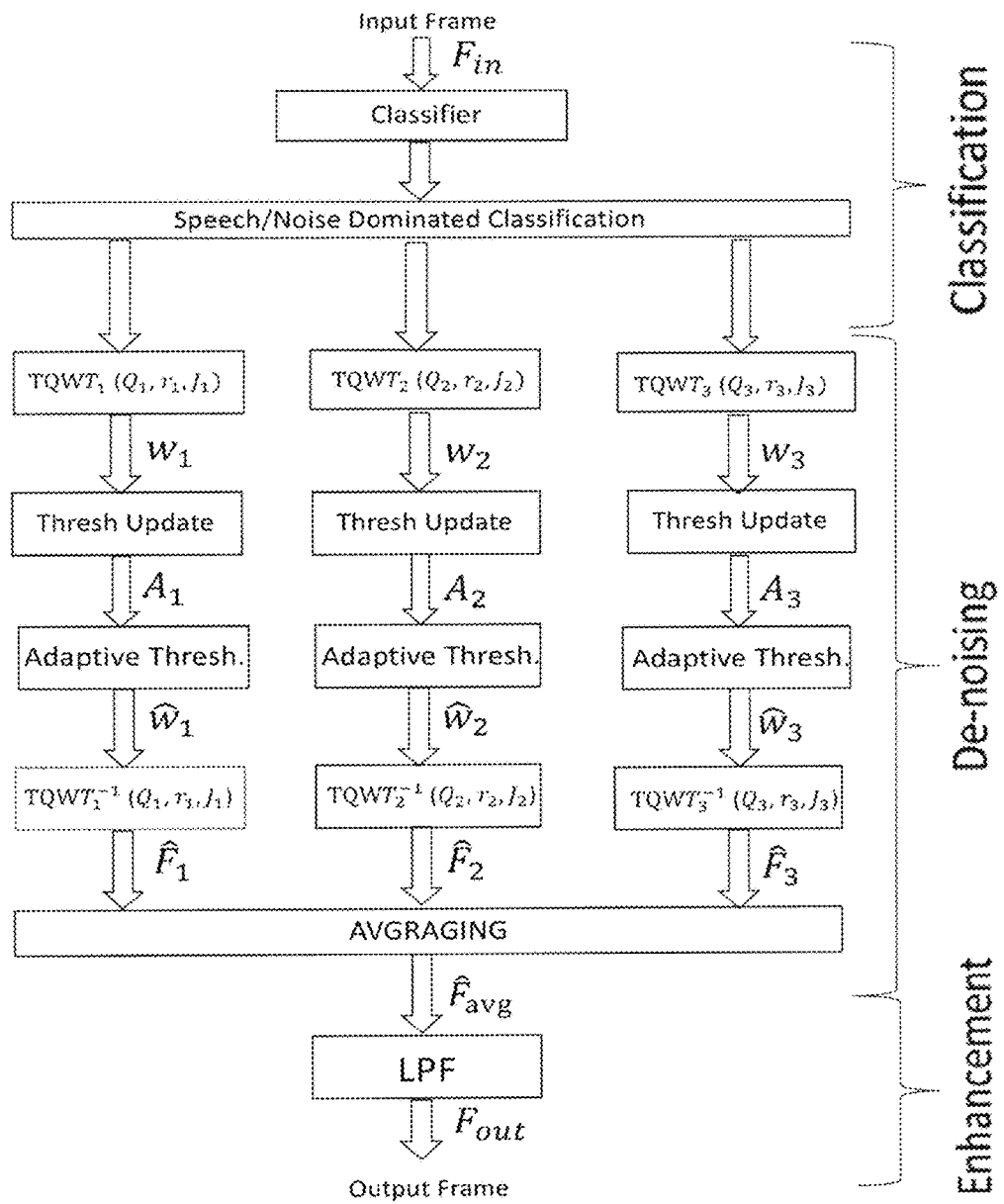
FIG. 23 shows an exemplary embodiment of a method for parallel de-noising and SEDA-RT as described Example III.

Now applying inverse TQWT $\hat{w}_1$, $\hat{w}_2$ and $\hat{w}_3$ and obtain:

$$\hat{F}_1 = TQWT_1^{-1}(\hat{w}_1)$$

$$\hat{F}_2 = TQWT_2^{-1}(\hat{w}_2)$$

$$\hat{F}_3 = TQWT_3^{-1}(\hat{w}_3) \qquad (45)$$

where $\hat{F}_1$, $\hat{F}_2$ and $\hat{F}_3$ are three different de-noised versions of the F, resulting from three parallel adaptive group thresholding processes. Finally, the averaged result will be:

$$\hat{F}_{avg} = \alpha(\hat{F}_1 + \hat{F}_2 + \hat{F}_3) \qquad (46)$$

where $\alpha$ is a regularization parameter to control the output signal's energy (FIG. 23).

3. Enhancement

Even after parallel de-noising, some babble noise will remain in the signal that may be further removed in this stage. Investigating this remaining noise shows, this noise does not exactly exhibit the behavior of the babble noise anymore. It has been processed by multiple different thresholding steps and its structure is significantly altered by the adaptive group thresholding. It has also been averaged with different versions of itself after parallel de-noising. Looking more closely at the properties of the remaining noise after the parallel de-nosing stage, two properties of the babble and speech dominated frames before and after parallel de-nosing may be observed. In this example, the selected two properties are: spectral flatness and high-frequency to low-frequency energy ratio.

Figure 24:
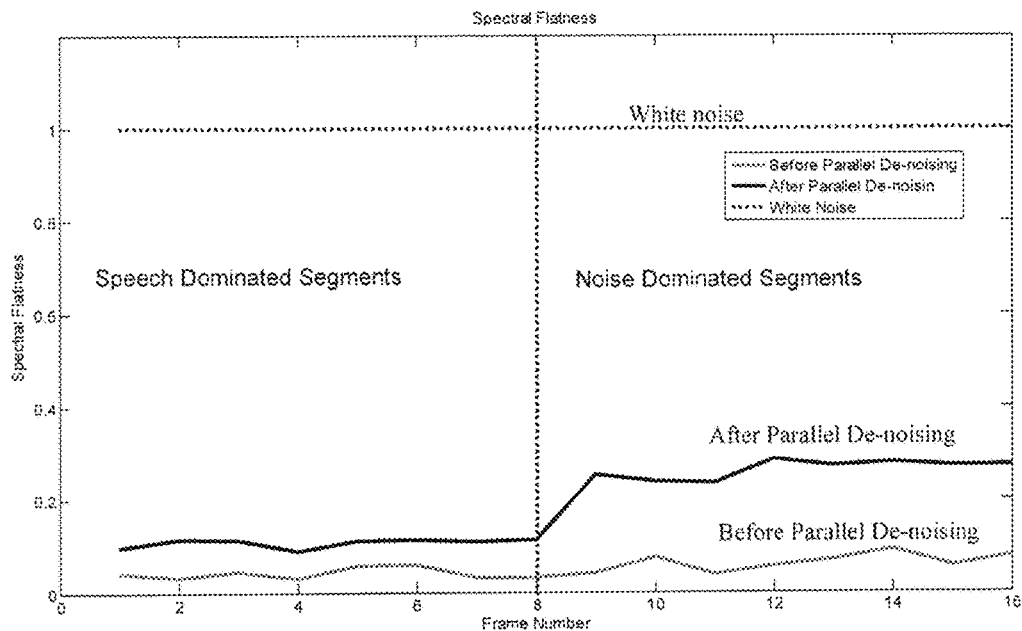
FIG. 24 shows data corresponding to exemplary input signals showing spectral flatness variation before and after parallel de-noising, as described Example III.

The index of spectral flatness measures how flat the spectrum of a signal is. It is designed to measure the similarity of a signal to the white noise (flat spectrum) or a pure tone (impulse shape spectrum). It is defined as the ratio of the geometric mean of the signal's spectrum to its arithmetic mean. The index of spectral flatness of a signal is a value between zero and one. The index of spectral flatness of white noise is one and spectral flatness of a pure tone is zero. The higher spectral flatness of a signal is, the more white-noise-like that signal will be. Spectral flatness can be calculated as follows:

$$SF(m) = \frac{\left(\prod_k |X(m,k)|\right)^{\frac{1}{K}}}{\frac{1}{K}\sum_k |X(m,k)|} \qquad (47)$$

where: m is the frame number and k is the frequency bin. The experiments conducted in this example show that the spectral flatness of the noise dominated frames will drastically increase after parallel de-nosing. But this is not true for speech-dominated frames. (see FIG. 24).

The second property is high-to-low frequency energy ratio. In this example, the selected border between high and low frequency is f=3500 Hz. For an audio signal x with total energy of $E^x$, $E_{f>3500}^x$ may be defined as the energy of the x after it is filtered with an ideal high pass filter with cut-off frequency of f=3500 Hz. $E_{f\leq 3500}^x$ may also be defined as the energy of the x after filtered with an ideal low pass filter with cut-off frequency of f=3500 Hz. $R_{f=3500}(x)$ may be defined as:

$$R_{f=3500}(x) = \frac{E(X_{f>3500})}{E(X_{f\leq 3500})} \qquad (48)$$

Figure 25:
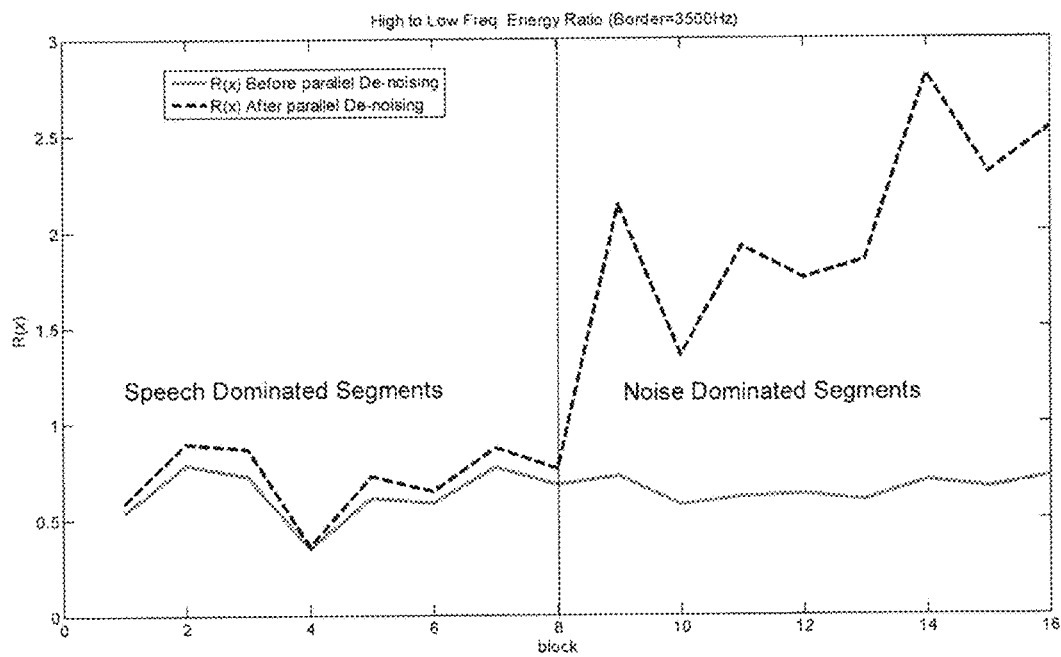
FIG. 25 shows data corresponding to high-to-low frequency energy ratio variation before and after parallel de-noising for an exemplary input signal according to Example III.

The experiments conducted according to Example III show that $R_{f=3500}(x)$ remains almost constant for speech dominated frames, after and before parallel de-noising while it drastically increases for noise dominated frames. That means after parallel de-noising, the proportion of high frequency components increases in the noise dominated frames. (see FIG. 25)

One possible explanation for this phenomenon is that since the adaptive group thresholding is adjusted based on the noise level, target speech coefficients get less distorted by the threshold while noise (babble) coefficients are more likely to be effected. The remaining isolated noise originated coefficients (Impulse shape with high frequency content) which have survived the adaptive group thresholding will be added to other isolated noise originated coefficients during the parallel de-noising and further lose their speech-likeness property and start to behave more like a stationary noise with significant high frequency content.

Figure 26:
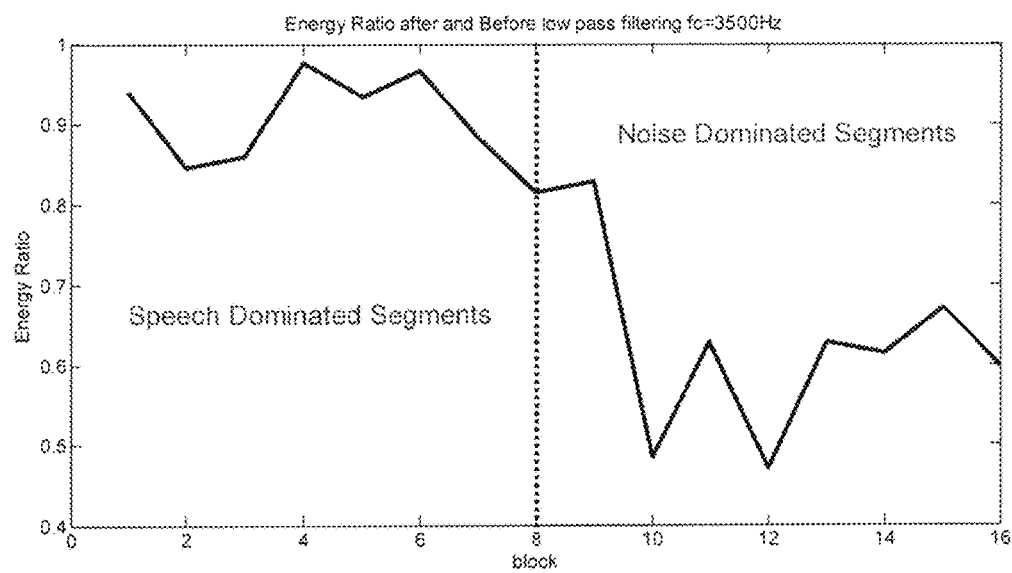
FIG. 26 shows data corresponding to an exemplary output of parallel de-noising of an exemplary input signal demonstrating variation of energy ratios for speech-dominated and noise-dominated frames, as described in Example III.

In this example, pure speech and pure babble frames were used to measure the above mentioned properties. In normal use (e.g., with a cochlear implant or a telephone) every input frame contains both speech and babble. Even in a speech-dominated frame there can be noise-dominated sub-frames. Because speech and babble are so inter-tangled, the best approach to exploit the above-mentioned properties is to apply a suitable low-pass filter to the results of the parallel de-noising step. Because the noise, resulting from the parallel de-noising step has higher proportion of high frequency energy, by low pass filtering, noise becomes more attenuated than speech. To verify the effectiveness of low-pass filtering, the following may be used:

$$R_{LP}(x) = \frac{E_{LP}(x)}{E(x)} \quad (49)$$

where E(x), $E_{LP}$(x) are the energy signal x before and after low pass filtering respectively. FIG. 26 shows the variation of $R_{LP}$(x) for speech-dominated and noise-dominated frames (output of parallel de-noising). As shown, low-pass filtering has removed more noise than speech. (Note that in this example of SEDA-RT, a 6th order Butterworth low pass filter was used with cut-off frequency of 4500 Hz).

Example IV

As discussed above, the exemplary method 300 provides a babble noise reduction method (e.g., a SEDA-RT) that solves the ineffectiveness of simple temporal/spectral thresholding. Example IV, as described herein, provide a detailed description of another exemplary embodiment of the three stages of exemplary method 300 (e.g., SEDA-RT), methods for clinical testing of the exemplary method, and collected data from CI users using SEDA-RT. In addition, the speed and latency of the exemplary embodiment of method 300 are measured using different computing machines (e.g., cell phones, tablets, and computers).

In this particular example, step 304 for classifying each frame of an input signal into a first or second category is substantially similar to Example III, Section 1, as discussed above. However, the classification using MAP (Section 1.6) is further modified as indicated below, and performance evaluations of the features as modified (Section 1.7) for Example IV are reported below.

1.6 Classification Using MAP (Maximum a Posteriori Estimation)

The values of P($class_N$) and P($class_S$) change as a function of the overall (long term) SNR and can be obtained during training by computing the number of each class occurrence divided by the total data samples in training data for each overall SNR. If the overall SNR changes very quickly (i.e., fast varying noisy condition) we can assume P($class_N$)=P($class_S$)=0.5. In most of the cases the general noise level does not change quickly (i.e., slow varying overall SNR). In this situation we can estimate more accurate values for P($class_N$) and P($class_S$) by roughly estimating the global SNR. To estimate the global SNR we suggest a very simple classifier which classifies the long frames of the noisy speech (i.e., four seconds long) into one of the 6 classes listed in Table 4 and choose the P($class_N$) accordingly. Table 4 below shows selected values for P($class_N$) for various overall SNR classes. Note that P($class_N$)=1−P($class_N$).

Figure 27:
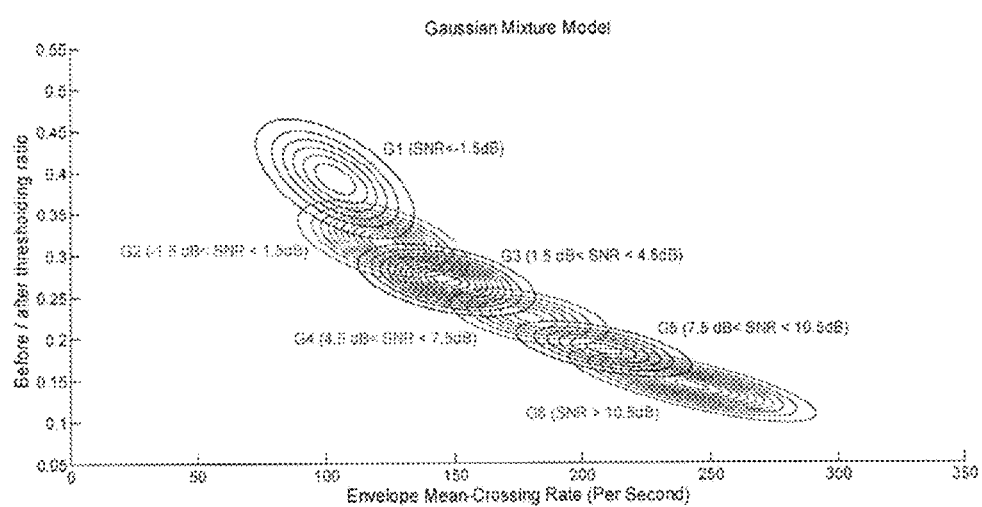
FIG. 27 shows data corresponding to a Gaussian Mixture Model (GMM) using an Expectation-Maximization (EM) method as described in Example IV.

The overall SNR classifier uses only two of the features mentioned earlier (i.e., RMS ratio and envelope mean crossing) calculated over the long frames of the noisy speech without de-correlating the features with PCA. In this example, GMM was used with a single Gaussian per class for training the overall SNR classifier (see FIG. 27). FIG. 27 shows GMM plots using EM method with only one Gaussian per class for overall SNR classifier, computed over 50,000 long frames of randomly generated noisy speech corrupted with multi-talker babble with random SNR and number of talkers (Between 5-10). As used in the example shown in FIG. 27, Long Frames Duration=4 seconds, and Sampling rate=16000 cycles per Second. Note that the independent accuracy of the overall SNR classifier is not of a concern. However, this classifier works as a component of the SEDA classifier and its accuracy will affect the accuracy of SEDA classifier. The SEDA classifier's accuracy is measured in the next section. P($class_N$) and P($class_S$) should be continuously updated based on the estimated overall SNR (The frequency of global SNR detection update depends on our assumption of how fast the noisy environment varies.). In this example, P($class_N$) and P($class_S$) were updated once every four seconds.

1.7 Performance Evaluation

Figure 28:
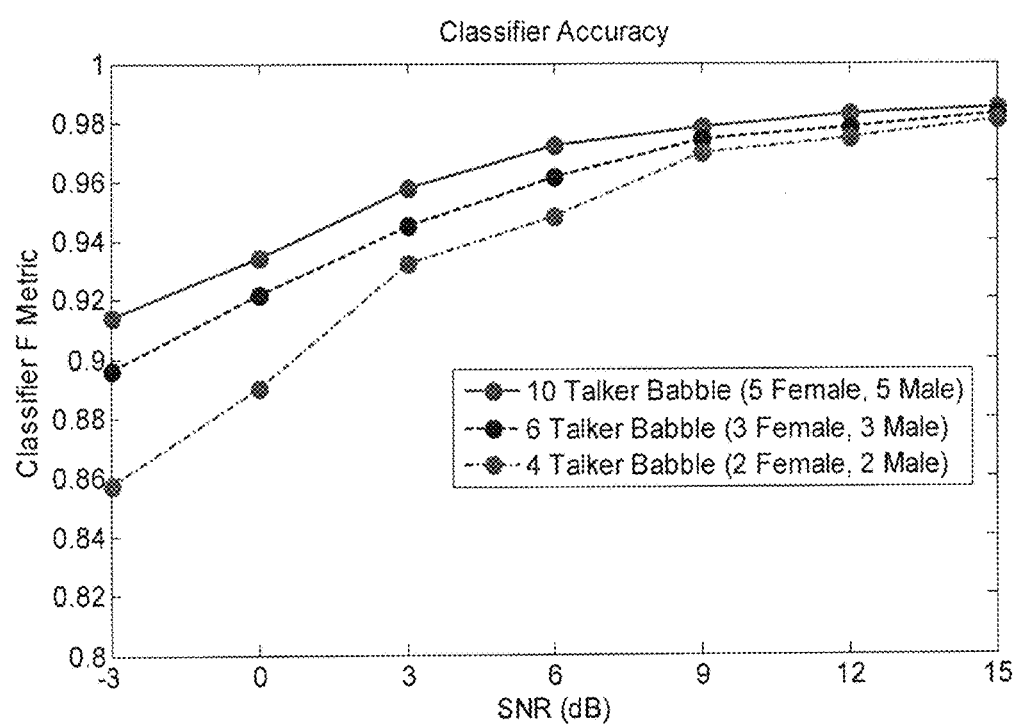
FIG. 28 shows data corresponding to an accuracy metric (F) of a SEDA-RT classifier measured over 1 hour of sample noisy speeches corrupted with multi-talker babble for each overall SNR and babble type using an exemplary two-fold cross validation method as described in Example IV.

The performance of the classifier was evaluated using two-fold cross validation. First, the classifier was trained with noisy speech samples randomly created from half of the sentence database. Then the resulting classifier was evaluated using test samples created from the second half of the sentence data base. Then we replaced the testing and training database and repeated the same process. The average values of following accuracy metrics were measured:

$$P = \frac{C}{C + f^+} \quad R_N = \frac{C}{C + f^-} \quad F = \frac{2PR}{P + R}$$

where C, $f^+$ and $f^-$ are correct, false positive and false negative detection, respectively. For this example, FIG. 28 shows accuracy metric (F) of SEDA classifier measured over 1 hours of noisy speech corrupted with multi-talker babble for each overall SNR and babble type using two-fold cross validation method. In particular, FIG. 28 shows the calculated F accuracy metric for a classifier trained with a single Gaussian for each class. The same result was achieved by testing the classifier with 10-talker babble extracted from the AzBio testing material which consists of 5 male and 5 female speakers.

2. Denoising

Sparsification using an oversampled wavelet transform is an effective way to minimize the overlapping between signal and noise coefficients. However, sparsification is an iterative process which often cannot be implemented in real-time algorithms due to its high computational requirements. Moreover, human speech cannot be efficiently sparsified in most wavelet domains unless implement additional measures are implemented (e.g., Morphological Component

TABLE 4

| Overall SNR | SNR < −1.5 dB | −1.5 dB < SNR < 1.5 dB | 1.5 dB < SNR < 4.5 dB | 4.5 dB < SNR < 7.5 dB | 7.5 dB < SNR < 10.5 dB | SNR > 10.5 dB |
|---|---|---|---|---|---|---|
| P($class_s$) | 0.8171 | 0.6599 | 0.4907 | 0.3645 | 0.2695 | 0.1941 |

Analysis (MCA)). The representation of the clean speech samples in an oversampled Tunable Q-factor Wavelet Transform (TQWT) exhibits some degree of group sparsity which does not exist in babble samples. SEDA takes advantage of this property (among others) to denoise the speech samples which are corrupted by multi-talker babble.

Figure 29A:
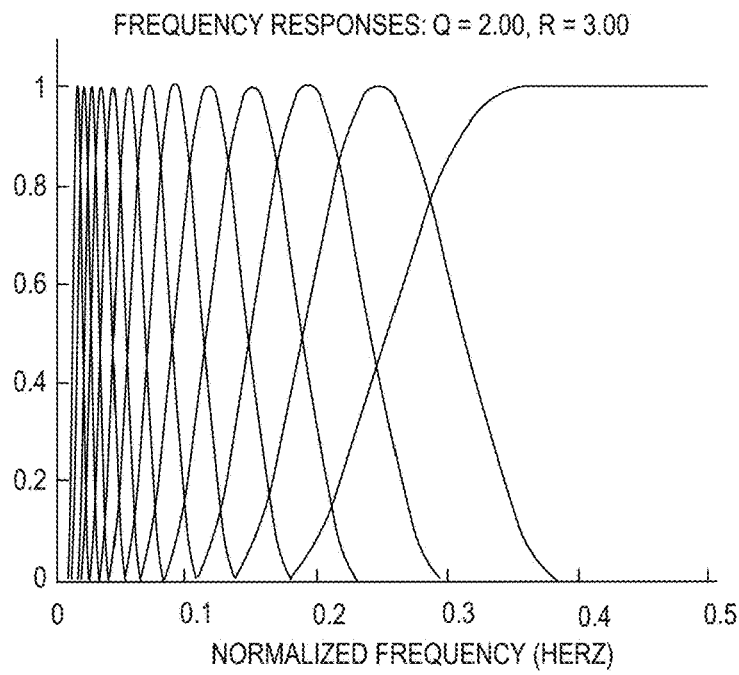
FIG. 29a shows data corresponding to frequency response of an exemplary input signal represented in a TQWT wavelet, as described in Example IV.
Figure 29B:
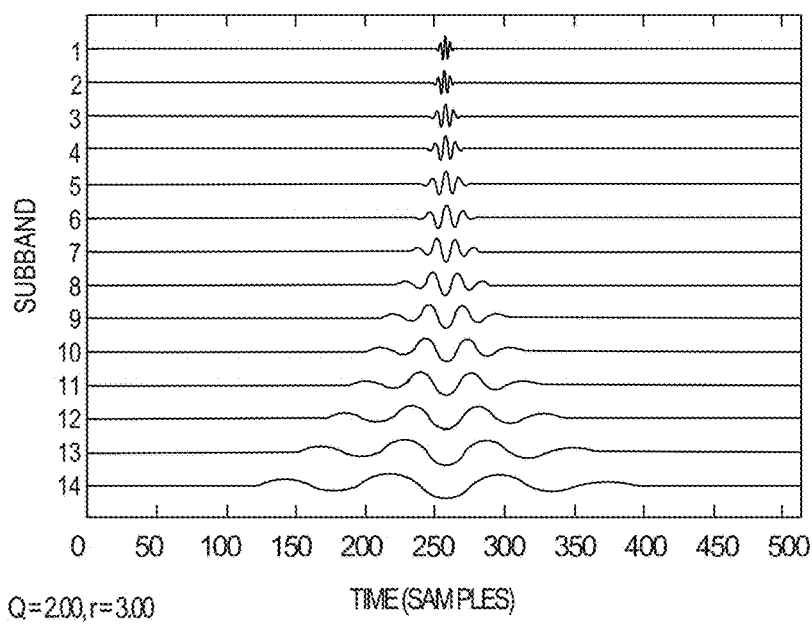
FIG. 29b shows data corresponding to sub-band wavelets of an exemplary input signal represented in a TQWT wavelet, as described in Example IV.
Figure 29C:
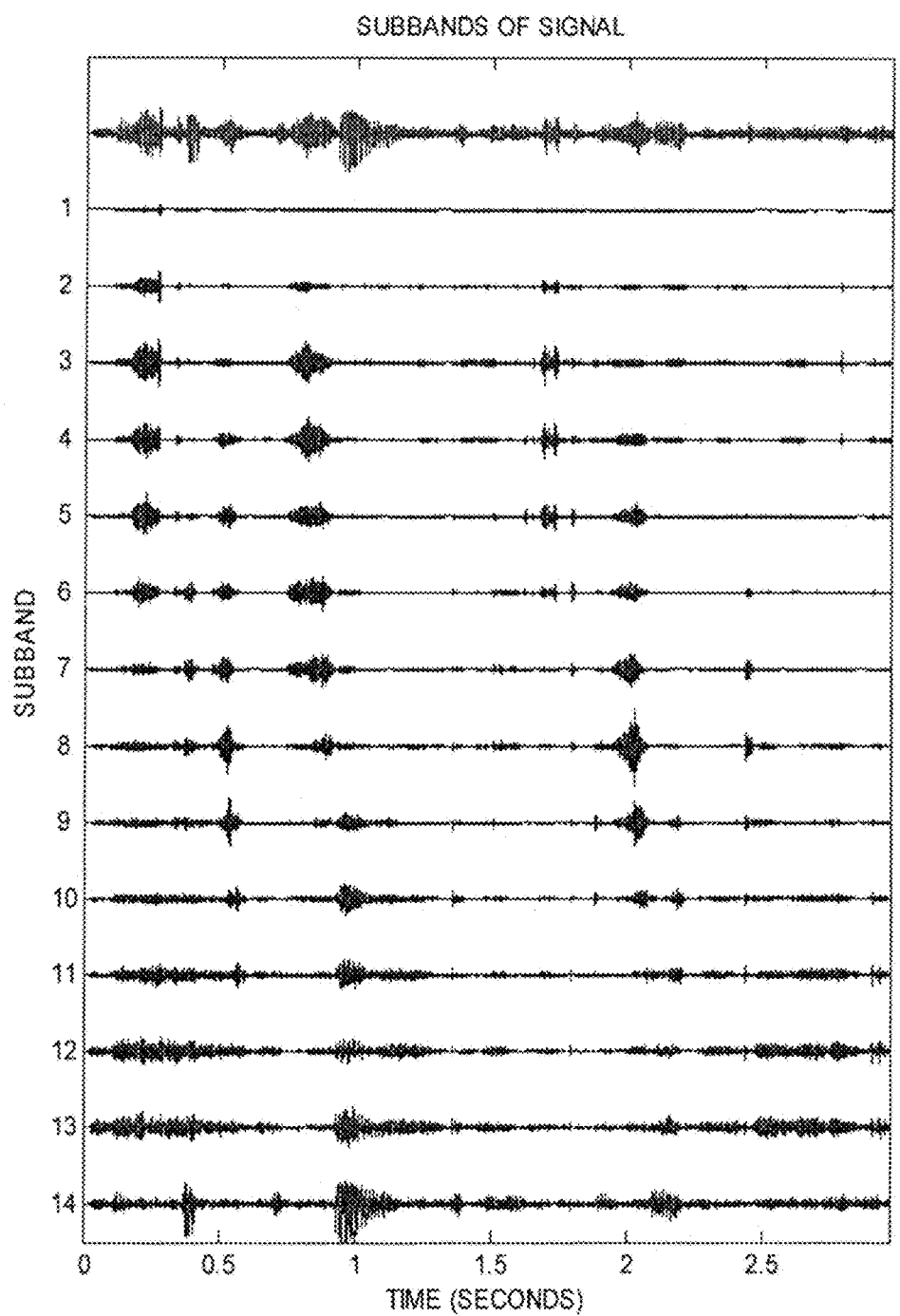
FIG. 29c shows data corresponding to sub-band coefficients of an exemplary input signal represented in a TQWT wavelet, as described in Example IV.

In this example, Q=2, r=3, J=13. FIGS. 29*a-c* show frequency response (FIG. 29*a*) sub-band wavelets (FIG. 29*b*) and sub-band coefficients (FIG. 29*c*) of a TQWT with Q=2, r=3, J=13. Note that increasing the oversampling rate of a wavelet transform will increase number of samples and consequently the required computation by the same factor. Hence using a conventional filter bank in which each output channel has the same sampling frequency as the input signal has the disadvantage of increasing the computational costs in real-time applications. TQWT provides the ability to optimize the oversampling rate. A TQWT is defined by three parameters which can be adjusted independently: Q-factor, the redundancy, and the number of levels (FIGS. 29*a-c*). The Q-factor is a measure of the oscillatory behavior of a pulse; it is defined in terms of the spectrum of the pulse as the ratio of its center frequency to its bandwidth. The redundancy is the over-sampling rate of the wavelet transform and is always greater than 1. By changing these parameters, different representations of the signal in the wavelet domain may be obtained. This property may be subsequently used in a parallel denoising technique, which is further discussed below. Another advantage of the TQWT is in its spectral properties, namely the frequency responses of its sub-bands, are consistent with the human auditory system. The distribution of the center frequencies of the sub-bands and the shape of the frequency responses of the TQWT resemble Mel-scale and Gammatone filter banks that are designed to reflect the human auditory system (FIGS. 29*a-c*).

2.1 Adaptive Group Thresholding

An adaptive group thresholding of the TQWT domain coefficients of the noisy speech may be determined based on the following strategies:

1. For each sub-band i in the TQWT domain, the threshold level may be just enough to remove most of the babble noise with minimum distortion of the target speech. Hence for a given sub-band i the noise level should be known in order to select the appropriate threshold level. If the current noisy speech frame is speech dominated, the noise level is estimated based on the average noise level in the same sub-band over the last few noise dominated frames.
2. For every frame, each TQWT sub-band is divided into multiple shorter segments (i.e., coefficient-group) where each coefficient-group consists of a few coefficients (typically 16). Hard and soft thresholding will be used alternatively for different coefficient-groups. For a real-valued signal x, hard and soft thresholding with threshold level T are defined with Hr(x) and S(rx) as follows:

$$H_T(x) = \begin{cases} 0, & |x| \le T \\ x, & |x| > T \end{cases} \quad S_T(x) = \begin{cases} x+T, & x < -T \\ 0, & -T \le x \le T \\ x-T, & x > T \end{cases} \quad (50)$$

Hard thresholding will be used for coefficient-groups with small $l_1$ norm value. This will remove many small coefficients originating from the noise source. Recall that target speech is louder than any individual background talker and has some degree of group sparsity in TQWT domain, therefore low amplitude coefficients scattered across the sub-band without forming a distinct group of coefficients, are more likely to originate from the babble source. A milder soft thresholding (with a smaller threshold level) will be used for coefficient-groups with large $l_1$ norm. This will prevent distortion when a mixture of large and small coefficients coming from target speech are concentrated in a group/cluster (see FIG. 31). Using an aggressive hard thresholding in these cases would eliminate the smaller coefficients and would lead to distortion.

3. General thresholding aggressiveness (level) for each frame is also determined based on the result of the classification. A more aggressive thresholding is used for noise-dominated frames whereas a less aggressive thresholding is used for speech-dominated frames. Details are given in following sub-sections.

2.1.1 Updating the Threshold Level

As previously mentioned, threshold levels in each sub-band depend on the average noise level over the last few noise dominated frames. To update the noise level estimation for every incoming frame an array $\bar{\mu}$ may be defined as follows:

$$\bar{\mu} = \begin{bmatrix} \mu_1 \\ \mu_2 \\ \vdots \\ \mu_{j+1} \end{bmatrix} \text{ where: } \mu_i = \frac{1}{M} \sum_{k=1}^{M} \|w_i^{(k)}\|_1 \text{ and} \quad (51)$$

$$w^{(k)} = \{w_1^{(k)}, w_2^{(k)}, \ldots, w_{j+1}^{(k)}\} = \varphi(F_n^{(k)})$$

where $\mu_i$ is the estimated noise level for sub-band i, obtained by averaging $l_1$ norm of that sub-band over the last M noise dominated frames, $F_n^{(k)}$ is the last kth noise dominated frame and $w_i^{(k)}$ is its ith sub-band in TQWT domain and J is the total number of levels in TQWT (denoted with $\Phi$). The selected value for M depends on the variation of the ambient noise level. For a steadier ambient noise level, we can choose a larger M whereas for a fast-varying noise level, we should select a smaller M. In the case of non-stationary noises including multi-talker babble, smaller M (i.e., M<5) is preferred. As the number of talkers increase, M may also be increased. In the event that a new noise dominated frame $F_n^{(M+1)}$ is detected, each element of array $\bar{\mu}$ may be updated as follows:

$$\mu_i^{new} = \frac{(M-1)\mu_i^{old} + \|w_i^{(M+1)}\|_1}{M} \quad (52)$$

Figure 30:
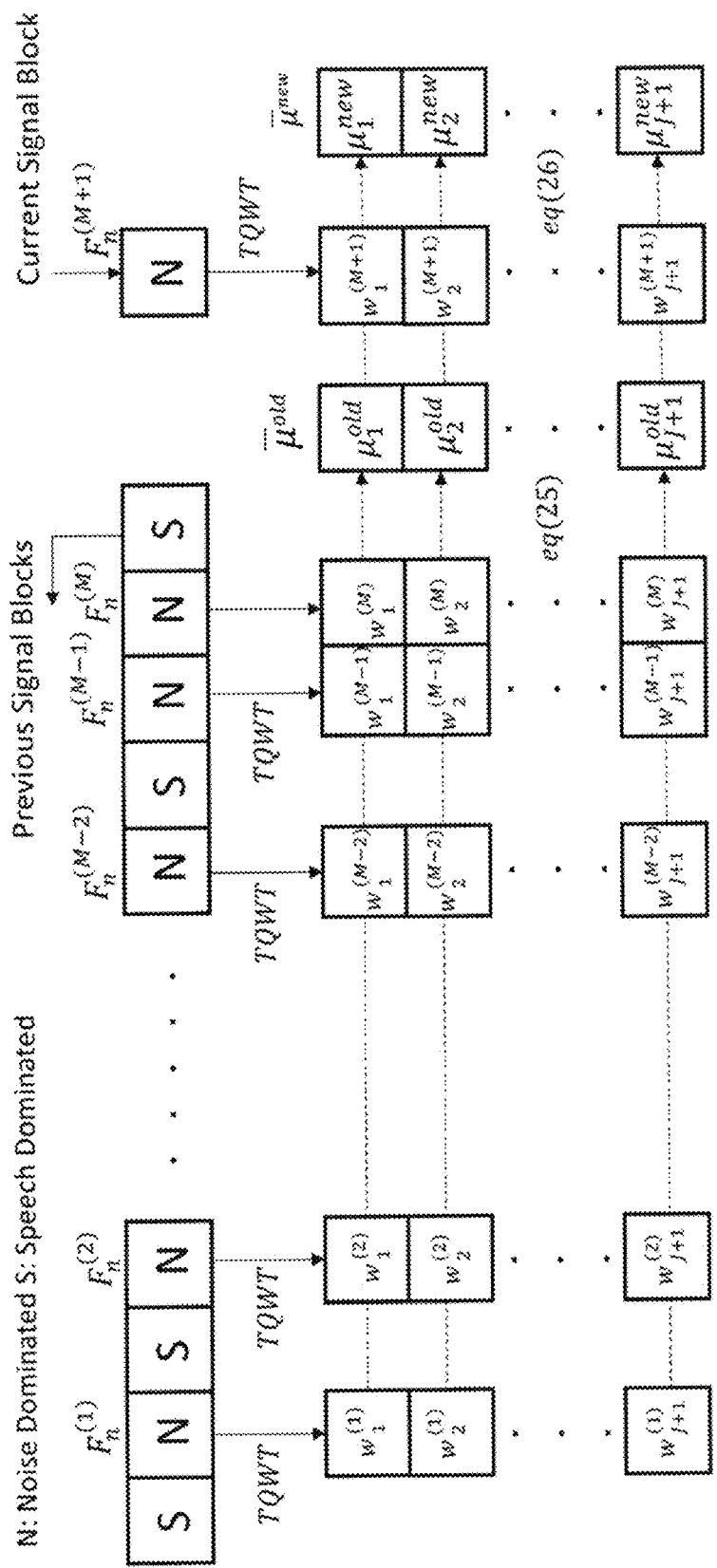
FIG. 30 shows an exemplary embodiment for a method for an average noise level updating process as described Example IV.

This updating process is shown in FIG. 30, which provides a block diagram of the average noise level updating process.

2.1.2 Thresholding

The previous steps produce an updated array of estimated noise levels for all sub-bands. Using this array, we implement the adaptive group thresholding for each sub-band as follows: Denoting by F an incoming frame of the noisy speech, we write:

$w = \Phi(F)$ where $w = \{w_1, w_2, \ldots, w_{j+1}\}$

As discussed above, each TQWT sub-band i will be divided into $n_i$ coefficient-groups as follows: $w_i = (c_1, c_2, \ldots, c_{n_i})$ where $c_1$ to $c_{n_i}$ are coefficient-groups of $w_i$. For each coefficient-group $c_k$ of sub-band $w_i$ we define $r_k^{(i)}$ as:

$$r_k^{(i)} = n_i \frac{\|c_k\|_1}{\|w_i\|_1}. \quad (53)$$

Figure 31:
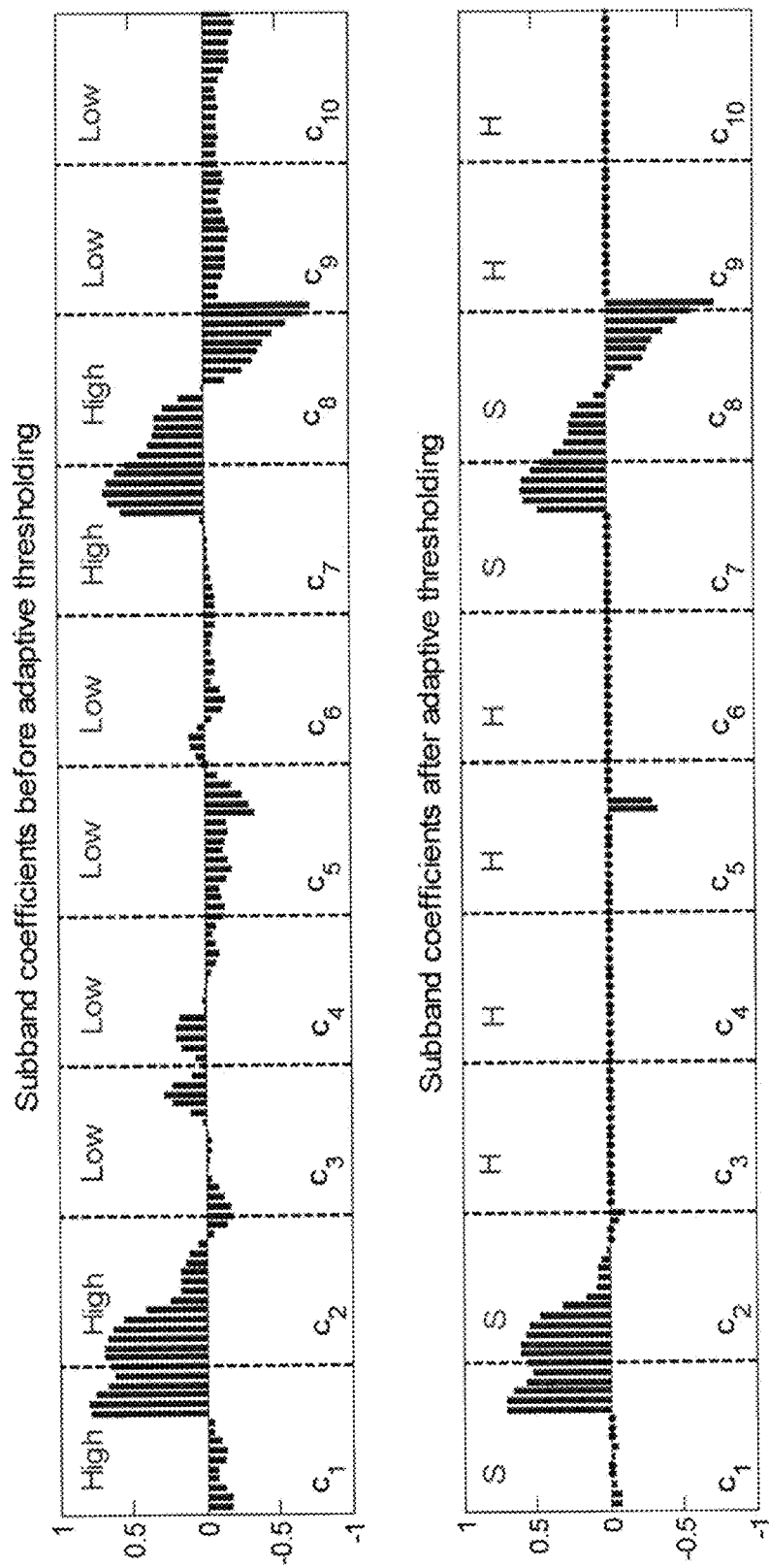
FIG. 31 shows data corresponding to an exemplary embodiment of adaptive group thresholding in a sub-band of TQWT as described in Example IV.

Using $r_k^{(i)}$ we classify each coefficient-group as either high-amplitude or low-amplitude, and apply hard and soft thresholding to low and high amplitude coefficient-groups respectively. as follows:

$$\hat{c}_k = \begin{cases} H_T(c_k), & r_k^{(i)} \le \gamma \\ S_{\epsilon T}(c_k), & r_k^{(i)} > \gamma \end{cases}, \quad T = \frac{\rho \tau \mu_i}{L_i} \quad (54)$$

where $\mu_i$ is the updated average noise level of the sub-band i over the last M noise-dominated frames, $L_i$ is the length of sub-band i, $\tau$ controls the thresholding aggressiveness based on the frame's class (e.g., $\tau=1$ for speech dominated frames and $\tau=1.5$ for noise dominated frames), $\rho$ determines our desired overall denoising aggressiveness ($1.5<\rho<3$ is the typical range), $\in$ is a reduction factor for soft thresholding which should always be smaller than 1 (e.g., $\in=0.3$) and $\gamma$ should always be greater than 1 (e.g., $\gamma=5$). FIG. 31 shows an example of adaptive group thresholding in a sub-band of TQWT: coefficient-groups numbers ($e_i$), High amplitude coefficient-groups (High), Low amplitude coefficient-groups (Low), Hard thresholding (H) and Soft thresholding (S) are shown before and after adaptive thresholding. FIG. 31 shows that soft thresholding preserves the shape of the clusters (by keeping smaller coefficients) in speech originated high amplitude coefficient-groups $c_1$, $c_2$, $c_7$ and $c_8$.

2.1.3 Parallel Denoising

Adaptive group thresholding usually inflicts some distortion to the original speech. A parallel denoising approach may be used to recover the distorted parts of the speech. Parallel denoising also changes the behavior of the residual babble noise. This property may be utilized to further de-noise the signal, as described further below.

Figure 32:
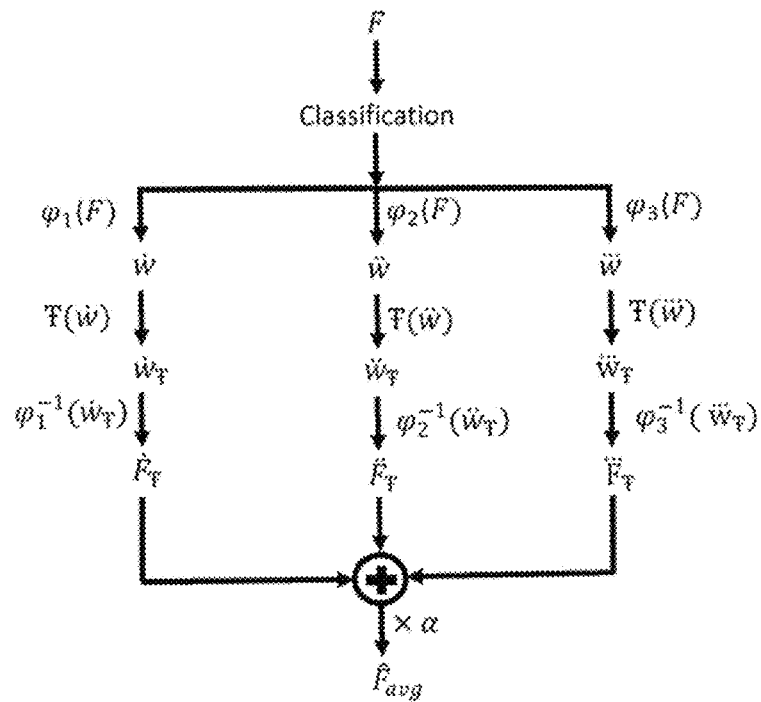
FIG. 32 shows an exemplary embodiment of a method for parallel de-noising as described Example IV.

First, three distinct representations of the signal in the wavelet domain may be created using three TQWTs with different settings. Then adaptive group thresholding may be applied to each representation and create three slightly different de-noised versions of the same signal. Three resulting de-noised signals will eventually be averaged. It is likely that, some areas which are distorted in one de-noised version will be recovered by another and this potentially reduces the overall distortion. FIG. 32 provides a diagram of the steps for parallel de-noising.

Figure 33:
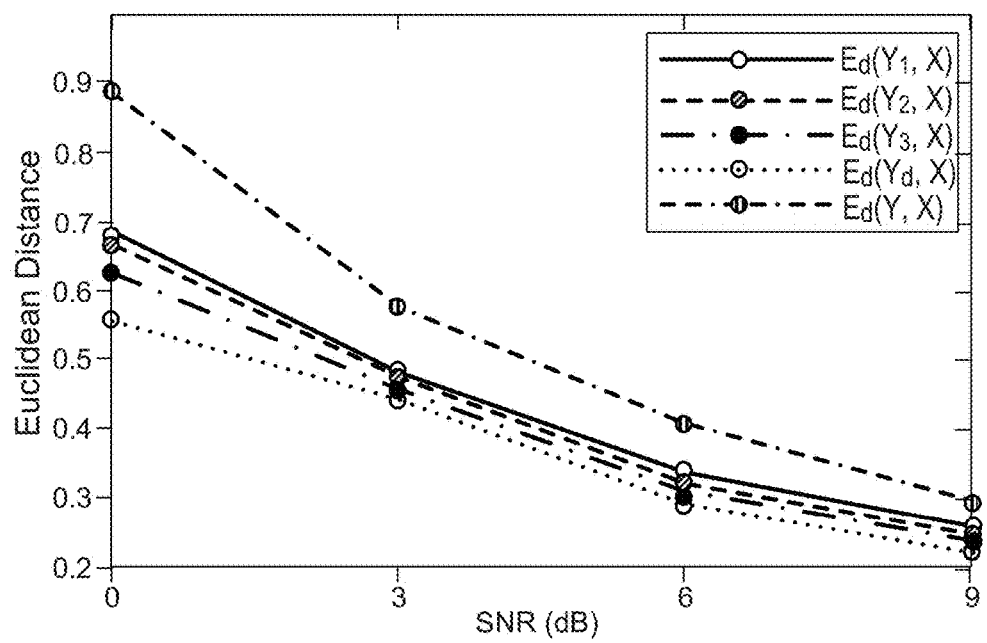
FIG. 33 shows data corresponding to normalized Euclidean distance between de-noised and clean speech for an exemplary input signal as described in the embodiment of Example IV.

To increase the denoising performance, three TQWTs should have low, medium and high Q factors respectively. This will assure three different representations in the wavelet domain. The redundancy and number of levels in each TQWT should be selected so that the signal's energy is distributed over many sub-bands. In this example, the selected values for a frame length of $2^{11}$ samples are: $Q_1=9$, $r_1=3$, $J_1=67$, $Q_2=5$, $r_2=3$, $J_2=43$, $Q_3=2$, $r_3=3$, $J_3=20$. Using three TQWTs, for an incoming noisy speech frame F: $\dot{w}=\Phi_1(F)$, $\ddot{w}=\Phi_2(F)$, $\dddot{w}=\Phi_3(F)$ where $\dot{w}$, $\ddot{w}$ and $\dddot{w}$ are three different wavelet domain representations of frame F. If the adaptive group thresholding process is denoted with $\mathcal{T}$: $\dot{w}_\mathcal{T}=\mathcal{T}(\dot{w})$, $\ddot{w}_\mathcal{T}=\mathcal{T}(\ddot{w})$ and $\dddot{w}_\mathcal{T}=\mathcal{T}(\dddot{w})$ and applying inverse TQWT to $\dot{w}_\mathcal{T}$, $\ddot{w}_\mathcal{T}$ and $\dddot{w}_\mathcal{T}$ we have: $\dot{F}_\mathcal{T}=\Phi_1^{-1}(\dot{w}_\mathcal{T})$, $\ddot{F}_\mathcal{T}=\Phi_2^{-1}(\ddot{w}_\mathcal{T})$ and $\dddot{F}_\mathcal{T}=\Phi_3^{-1}(\dddot{w}_\mathcal{T})$ where $\dot{F}_\mathcal{T}$, $\ddot{F}_\mathcal{T}$ and $\dddot{F}_\mathcal{T}$ are three different de-noised versions of F. Finally, the averaged result will be: $\hat{F}_{avg}=\alpha(\dot{F}_\mathcal{T}+\ddot{F}_\mathcal{T}+\dddot{F}_\mathcal{T})$ (55) where $\alpha$ is a gain parameter to control the output signal's energy (FIG. 32). To measure the effect of the parallel denoising on reducing the denoising distortion, normalized Euclidean distance was applied to the magnitude of the spectrograms which is defined as:

$$E_d(X_1, X_2) = \frac{\|\,|S_1| - |S_2|\,\|_2}{\|S_2\|_2} \quad (30)$$

where, $S_1$ and $S_2$ are Short Time Fourier Transforms (STFT) of audio signals $X_1$ and $X_2$ respectively. FIG. 33 shows average Euclidean distances between noisy speech and clean speech $E_d(Y,X)$, parallel de-noised speech and clean speech $E_d(Y_d,X)$ and three different de-noised versions and clean speech $E_d(Y_1,X)$, $E_d(Y_2,X)$ and $E_d(Y_3,X)$. In this example, the experiments show that parallel denoising effectively reduces the normalized Euclidean distance between de-noised and clean speech (FIG. 33).

3. Enhancement

Figure 34:
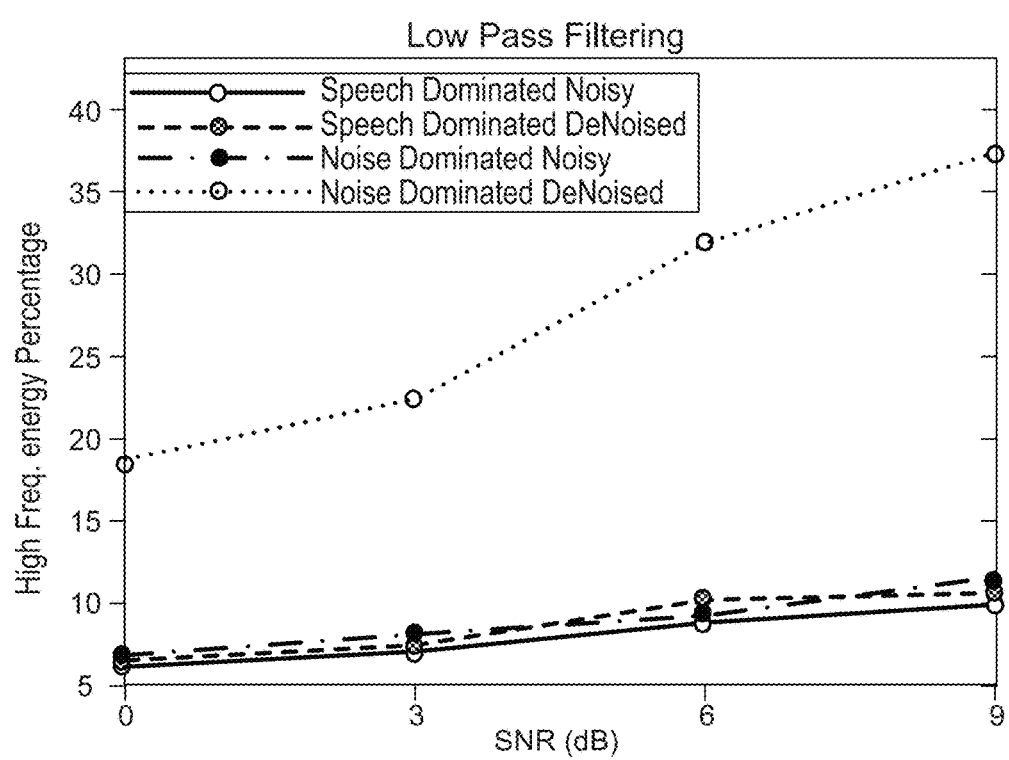
FIG. 34 shows data corresponding to high frequency energy percentage of speech and noise dominated frames before and after parallel de-noising for an exemplary input signal as described in the embodiment of Example IV.

Even though adaptive group thresholding and parallel denoising do not eliminate all the babble mixed with the target speech, they alter the babble properties. Adaptive group thresholding is adjusted based on the noise level. Hence coefficients originating from target speech are less affected by the thresholding whereas coefficients originated from babble are more likely to be attenuated or set to zero. Parallel denoising and adaptive group thresholding significantly alter the babble structure and reduce it to sporadic and isolated coefficients with high frequency content. (See impulse shape coefficients in coefficient-groups $c_5$ after thresholding in FIG. 31.) To investigate this, the high frequency content of speech and noise dominated frames were measured, after and before denoising. FIG. 34 shows high frequency energy percentage of speech and noise dominated frames before and after parallel de-noising (In this example, sampling rate=16000 cycles per second, High/low frequency border=2400 Hz). FIG. 34 shows that the energy of high frequency components remains almost constant in speech dominated frames, after and before parallel denoising whereas it drastically increases in noise dominated frames. To exploit the above-mentioned property, after parallel denoising a suitable low-pass filter may be applied only to the noise dominated frames, to remove the high frequency residual components resulting from the previous denoising steps and further enhance the speech quality. In this example, a 6th order Butterworth low pass filter with cut-off frequency of 4000 Hz may be used.

The invention described and claimed herein is not to be limited in scope by the specific embodiments herein disclosed since these embodiments are intended as illustrations of several aspects of this invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. All publications cited herein are incorporated by reference in their entirety.

What is claimed is:

1. A method for reduction of noise, comprising:
   receiving from a receiving arrangement an input audio signal frame comprising a speech signal and a noise;
   classifying the input audio signal frame into a first category or a second category, wherein the first category corresponds to the noise being stronger than the speech signal, and the second category corresponds to the speech signal being stronger than the noise;

decomposing the input audio signal frame into a plurality of sub-band components; and de-noising each sub-band component of the input audio signal frame in parallel by applying a first wavelet de-noising method including a first wavelet transform and a predetermined threshold for the sub-band component, and a second wavelet de-noising method including a second wavelet transform and the predetermined threshold for the sub-band component, wherein the predetermined threshold for each sub-band component is based on at least one previous noise-dominant signal frame received by the receiving arrangement, wherein the first and second wavelet transforms are configured to more aggressively de-noise the input audio signal frame when the input audio signal frame is classified in the first category as compared to when the input audio signal frame is classified in the second category, and wherein the classifying step comprises:

applying a principle component analysis using a plurality of features, wherein the plurality of features includes at least one of: (1) an envelope variance feature of the input audio signal frame; (2) an envelope mean crossing feature of the input audio signal frame; (3) a root mean square feature of the input audio signal frame as compared to a predetermined threshold value; and (4) an entropy feature of a histogram of the input audio signal frame; and classifying the input audio signal frame into the first category when the applying step identifies predominantly noise from the input audio signal frame, and into the second category when the principle component analysis identifies predominantly speech signal from the input audio signal frame.

2. The method of claim 1, wherein the noise comprises a multi-talker babble noise.

3. The method of claim 1, wherein the input audio signal frame is less than 100 ms in duration.

4. The method of claim 1, wherein each of the plurality of features is each weighted differently in the principle component analysis.

5. The method of claim 1, wherein the predetermined threshold value for the root mean square feature is based on a previous audio signal frame received by the receiving arrangement.

6. The method of claim 5, wherein the previous audio signal frame includes predominantly noise.

7. The method of claim 1, further comprising:

adjusting the plurality of features based on the input audio signal by an iterative method using a Gaussian mixture model for a plurality of sub-categories, wherein the first and second categories are each further divided into the plurality of sub-categories.

8. The method of claim 1, wherein the first and second wavelet transforms are Tunable Q-Factor Wavelet Transforms (TQWTs).

9. The method of claim 1, wherein the first and second wavelet transforms are selected based whether the input audio signal is classified into the first category or the second category.

10. The method of claim 1, wherein each sub-band component comprises a plurality of wavelet coefficients corresponding to an amplitude of the sub-band component of the input audio signal frame.

11. The method of claim 10, wherein the predetermined threshold for each sub-band component is selected based on an amount of noise present in the sub-band component, and an energy level represented by the plurality of wavelet coefficients.

12. The method of claim 1, further comprising:

enhancing an output signal by filtering each de-noised sub-band component with a low pass filter.

13. A non-transitory computer readable medium storing a computer program that is executable by at least one processing unit, the computer program comprising sets of instructions, when executed by the processor, causing the processor to perform steps of claim 1.

14. A method for improving intelligibility of speech, comprising:

obtaining, from a receiving arrangement, an input audio signal frame comprising a speech signal and a noise;

classifying the input audio signal into a first category or a second category, wherein the first category corresponds to the noise being stronger than the speech signal, and the second category corresponds to the speech signal being stronger than the noise;

decomposing the input audio signal frame into a plurality of sub-band components; and de-noising each sub-band component of the input audio signal frame in parallel by applying a plurality of wavelet de-noising methods, each wavelet de-noising method including a wavelet transform and a predetermined threshold for the sub-band component, wherein the predetermined threshold for each sub-band component is based on at least one previous noise-dominant signal frame received by the receiving arrangement, wherein each of the wavelet transforms is different from other wavelet transforms, and is each configured to more aggressively de-noise the input audio signal frame when the input audio signal frame is classified in the first category as compared to when the input audio signal frame is classified in the second category, wherein the classifying step comprises:

applying a principle component analysis using a plurality of features, wherein the plurality of features includes at least one of: (1) an envelope variance feature of the input audio signal frame; (2) an envelope mean crossing feature of the input audio signal frame; (3) a root mean square feature of the input audio signal frame as compared to a predetermined threshold value; and (4) an entropy feature of a histogram of the input audio signal frame; and classifying the input audio signal frame into the first category when the applying step identifies predominantly noise from the input audio signal frame, and into the second category when the principle component analysis identifies predominantly speech signal from the input audio signal frame.

15. The method of claim 14, wherein the noise comprises a multi-talker babble noise.

16. The method of claim 14, wherein the input audio signal frame is less than 100 ms in duration.

17. The method of claim 14, wherein the wavelet transforms are Tunable Q-Factor Wavelet Transforms (TQWTs).

18. A system for improving intelligibility for a user comprising:

a receiving arrangement configured to receive an input audio signal frame comprising a speech signal and a noise;

a processing arrangement configured to receive the input audio signal frame from the receiving arrangement, classify the input audio signal frame into a first category or a second category, wherein the first category corresponds to the noise being stronger than the speech signal, and the second category corresponds to the speech signal being stronger than the noise, decompose the input audio signal frame into a plurality of sub-band components, and de-noise each sub-band component of the input audio signal frame in parallel by applying a first wavelet de-noising method including a first wavelet transform and a predetermined threshold for the sub-band component, and a second wavelet de-noising method including a second wavelet transform and the predetermined threshold for the sub-band component, wherein the predetermined threshold for each sub-band component is based on at least one previous noise-dominant signal frame received by the receiving arrangement, wherein the first and second wavelet transforms are configured to more aggressively de-noise the input audio signal frame when the input audio signal frame is classified in the first category as compared to when the input audio signal frame is classified in the second category, wherein the processing arrangement is further configured to classify the input audio signal frame by:

applying a principle component analysis using a plurality of features, wherein the plurality of features includes at least one of: (1) an envelope variance feature of the input audio signal frame; (2) an envelope mean crossing feature of the input audio signal frame; (3) a root mean square feature of the input audio signal frame as compared to a predetermined threshold value; and (4) an entropy feature of a histogram of the input audio signal frame; and classifying the input audio signal frame into the first category when the applying step identifies predominantly noise from the input audio signal frame, and into the second category when the principle component analysis identifies predominantly speech signal from the input audio signal frame.

* * * * *